US011331381B2

(12) United States Patent
Foix Breto et al.

(10) Patent No.: US 11,331,381 B2
(45) Date of Patent: May 17, 2022

(54) VACCINE COMPOSITIONS FOR USE AGAINST DIGITAL DERMATITIS IN A MAMMAL

(71) Applicant: HIPRA SCIENTIFIC, S.L.U., Girona (ES)

(72) Inventors: Antoni Foix Breto, Girona (ES); Xavier Serra Hartmann, Sant Cugat del Vallès (ES); Marta Sitjà I Arnau, Girona (ES); Jaume Piñol Ribas, Barcelona (ES); Enrique Querol Murillo, Barcelona (ES)

(73) Assignee: HIPRA SCIENTIFIC, S.L.U., Girona (ES)

( * ) Notice: Subject to any disclaimer, the term of this patent is extended or adjusted under 35 U.S.C. 154(b) by 0 days.

(21) Appl. No.: 16/764,762

(22) PCT Filed: Nov. 16, 2018

(86) PCT No.: PCT/EP2018/081601
§ 371 (c)(1),
(2) Date: May 15, 2020

(87) PCT Pub. No.: WO2019/097009
PCT Pub. Date: May 23, 2019

(65) Prior Publication Data
US 2020/0360498 A1    Nov. 19, 2020

(30) Foreign Application Priority Data

Nov. 17, 2017  (EP) .................................. EP17382781

(51) Int. Cl.
| *A01N 63/00* | (2020.01) |
| *A61K 39/02* | (2006.01) |
| *A61P 31/04* | (2006.01) |
| *C12N 1/20* | (2006.01) |
| *A61K 39/00* | (2006.01) |

(52) U.S. Cl.
CPC ...... *A61K 39/0225* (2013.01); *A61K 39/0208* (2013.01); *A61P 31/04* (2018.01); *C12N 1/20* (2013.01); *A61K 2039/521* (2013.01)

(58) Field of Classification Search
CPC ................................................. A61K 39/0225
See application file for complete search history.

(56) References Cited

FOREIGN PATENT DOCUMENTS

WO         95/02186 A1    1/1995

OTHER PUBLICATIONS

Berry et al., "Etiology, Treatment and Prospects for Vaccination Against (Papillomatus) Digital Dermatitis," Proceesings of the 12th International Symposium on Lameness in Ruminants; Orlando, FL, USA, 2002.
Ertze et al., "Field Evaluation of Prophylactic and Therapeutic Effects of a Vaccine against (Papillomatus) Digital Dermatitis in Dairy Cattle on Two California Dairies," *The Bovine Practitioner* 40(2):76-82, 2006.
Evans et al., "Bovine digital dermatitis: Current concepts from laboratory to farm," *The Veterinary Journal* 211:3-13, 2016.
Evans et al., "Three unique groups of spirochetes isolated from digital dermatitis lesions in UK cattle," *Veterinary Microbiology* 130:141-150, 2008.
Fidler et al., "Evaluation of a *Serpens* species bacterin for treatment of digital dermatitis in dairy cattle," *Research in Veterinary Science* 93:1258-1260, 2012.
Keil et al., "Serological and Clinical Response of Cattle to Farm Specific Digital Dermatitis Bacterins," Proceedings of the 12th International Symposium on Lameness in Ruminants; Orlando, FL, USA, 2002.
Kennan et al., "The Type IV Fimbrial Subunit Gene (fimA) of *Dichelobacter nodosus* Is Essential for Virulence, Protease Secretion, and Natural Competence," *Journal of Bacteriology* 183(15):4451-4458, 2001.
Klitgaard et al., "Targeting the Treponemal Microbiome of Digital Dermatitis Infections by High-Resolution Phylogenetic Analyses and Comparison with Fluorescent In Situ Hybridization," *Journal of Clinical Microbiology* 51 (7):2212-2219, 2013.
Marcatili et al., "A novel approach to probe host-pathogen interactions of bovine digital dermatitis, a model of a complex polymicrobial infection," *BMC Genomics* 17:987, 2016 (13 pages).
Nielsen et al., "Potential bacterial core species associated with digital dermatitis in cattle herds identified by molecular profiling of interdigital skin samples," *Veterinary Microbiology* 186:139-149, 2016.
Berry et al., "Field Evaluation of Prophylactic and Therapeutic Effects of a Vaccine Against (Papillomatous) Digital Dermatitis of Dairy Cattle in Two California Dairies," Proceedings of the 13th International Symposium and 5th Conference on Lameness in Ruminants; Maribor, Slovenija, Feb. 11-15, 2004 (2 Pages).

*Primary Examiner* — Albert M Navarro
(74) *Attorney, Agent, or Firm* — Seed Intellectual Property Law Group LLP

(57) ABSTRACT

The present invention provides new pharmaceutical and vaccine compositions comprising *Treponema* spp. bacterins, supplemented with antigens from *Treponema* spp. or other digital dermatitis causative pathological agents such as but not limited to *D. nodosus* or *F. necrophorum*, for effectively immunizing susceptible mammals, preferably ungulates, against DD, in particular against bovine digital dermatitis. The present invention also identifies *Treponema pedis* and *Treponema phagedenis* as two of the etiologic agents of digital dermatitis (DD) in mammals, in particular ungulate digital dermatitis. The invention therefore also provides isolated cultures of *Treponema pedis* and *Treponema phagedenis* for effectively immunizing susceptible mammals, preferably ungulates, against DD, in particular against bovine digital dermatitis. In addition, the present invention provides methods of diagnosing DD by detecting infection with a series of specific *Treponema* antigens.

17 Claims, 12 Drawing Sheets
Specification includes a Sequence Listing.

A

B

A  B  C

A

B

A

B

A

B

C

A

B

C

A

B
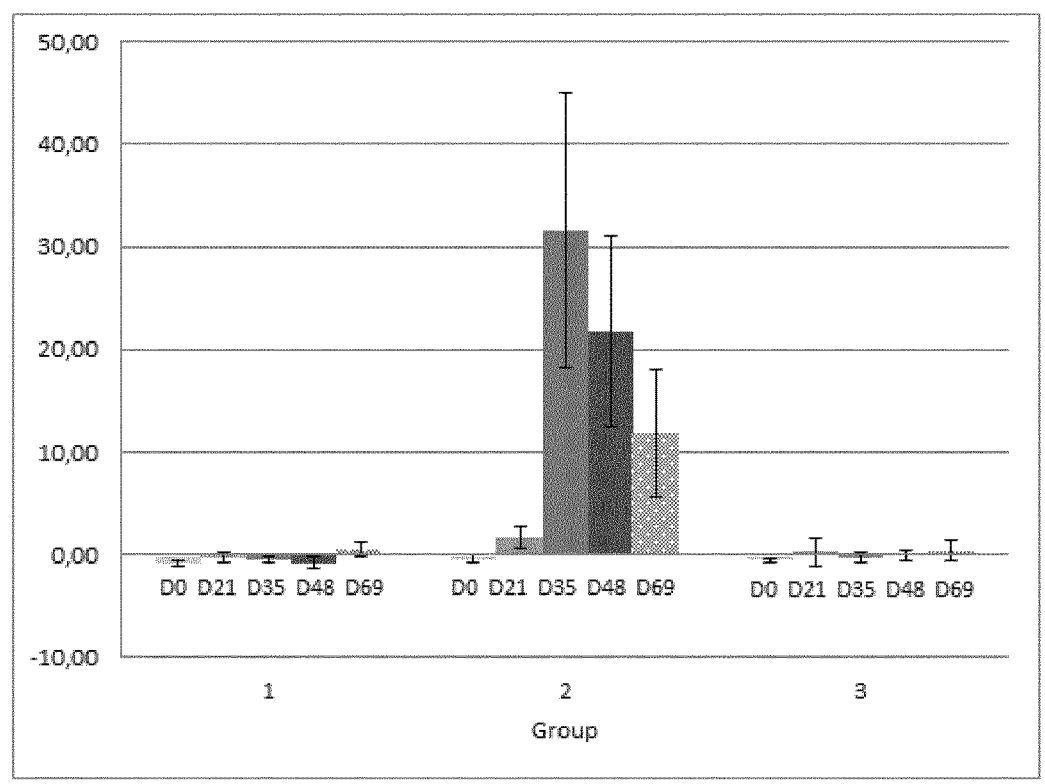
C
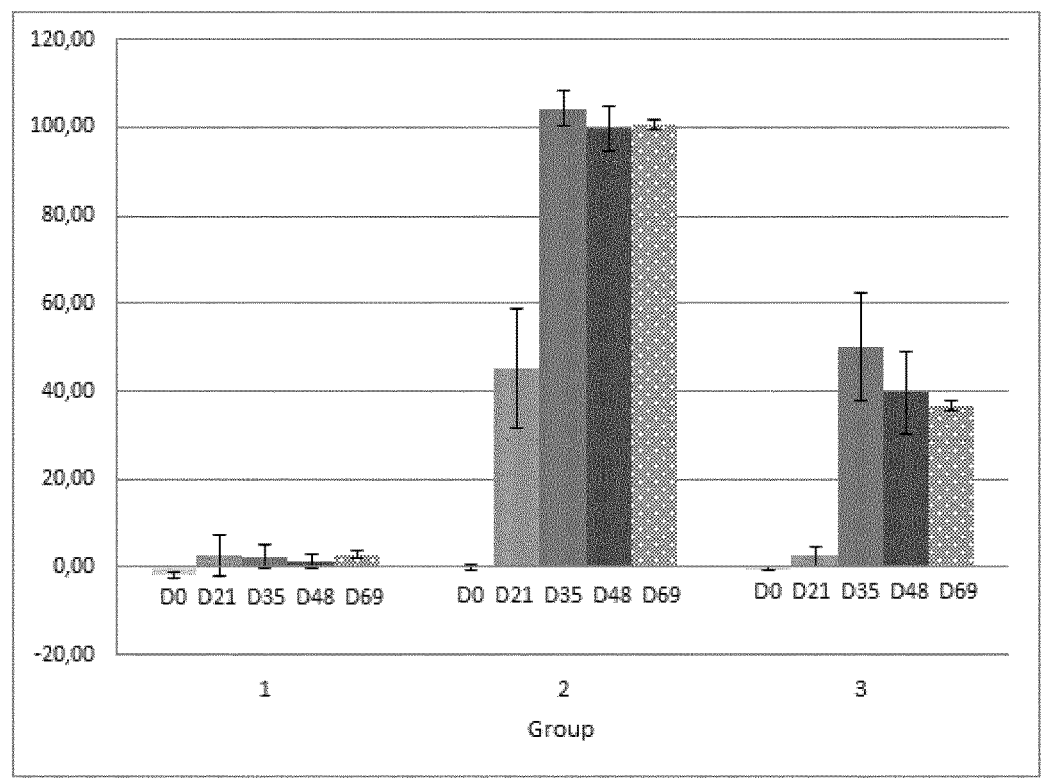

SEQUENCE LISTING

```
<160> NUMBER OF SEQ ID NOS: 15

<210> SEQ ID NO 1
<211> LENGTH: 746
<212> TYPE: PRT
<213> ORGANISM: Artificial Sequence
<220> FEATURE:
<223> OTHER INFORMATION: T. pedis "PrtP" (Dentilisin Component PrtP-like
      Protein)
<220> FEATURE:
<221> NAME/KEY: PEPTIDE
<222> LOCATION: (1)..(746)

<400> SEQUENCE: 1

Met Lys Lys Ile Leu Val Leu Ser Ala Val Leu Ala Ile Leu Ala Gly
1               5                   10                  15

Ser Cys Ser Phe Asn Ile Asp Pro Gln Asn Ile Ser Ser Asn Glu Gln
            20                  25                  30

Arg Val Gln Ser Met Glu Ala Leu Tyr Gly Asn Ser Ser Ser Val Ile
        35                  40                  45

Pro Tyr Ala Pro Lys Asp Glu Asp Thr Val Asp Gly Phe Phe Ile Val
    50                  55                  60

Lys Thr Lys Asp Gly Phe Asp Lys Thr Ala Phe Glu Glu Lys Gly Phe
65                  70                  75                  80

Thr Val Lys Gly Ala Leu Pro Leu Thr Gly Thr Gly Phe Thr Tyr Trp
                85                  90                  95

Tyr Leu Asn Lys Glu Gly Asn Asp Lys Lys Asn Leu Ser Val Ile Ser
            100                 105                 110

Ser Val Lys Gly Val Ile Ser Ala Glu Ser Asp Tyr Lys Val Glu Pro
        115                 120                 125

Pro Asp Gly Ile Lys Val Ala Lys Thr Val Asp Gly Gly Gly Leu Val
    130                 135                 140

Asp Ile Ser Arg Leu Ile Asn Gly Asp Tyr Ser Gly Asp Pro Ile Ala
145                 150                 155                 160

Asn Asn Ser Asp Tyr Gly Leu Ser Ile Thr Glu Ala Leu Lys Ala Tyr
                165                 170                 175

Lys Glu Ile Gly Tyr Gly Asp Lys Thr Val Val Ala Gly Ile Ile Ala
            180                 185                 190

Thr Gly Ile Asn Met Thr His Lys Asp Phe Lys Asp Glu Asn Gly Asn
        195                 200                 205

Ser Ile Val Leu Tyr Ala Lys Ser Cys Val Lys Ser Asn Gly Gly Thr
    210                 215                 220

Tyr Ile Gly Asn Gly Asn Pro Phe Thr Glu Ile Pro Ile Gly Glu Asn
225                 230                 235                 240

Trp Asp Lys Gly Ala Ala Gly Thr His Cys Ser Gly Thr Ile Cys Ala
                245                 250                 255
```

```
Arg Gly Asp Asn Asn Ala Gly Ile Ala Gly Val Ala Trp Lys Asn Thr
            260                 265                 270

Lys Leu Ile Ser Tyr Gln Ser Leu Asp Val Asp Gly Gly Ser Ala
            275                 280                 285

Trp Ala Val Tyr Gly Ala Leu Ala Asp Leu Thr Arg Thr Val Asn Ile
            290                 295                 300

Leu Arg Lys Pro Lys Ser Asp Arg Thr Leu Asp Glu Asn Asn Ala Leu
305                 310                 315                 320

Pro Ser Tyr Leu Lys Asn Glu Asp Phe Gln Ile Thr Gln Lys Thr Val
                325                 330                 335

Pro Val Asn Met Ser Leu Gly Gly Ser Tyr Gly Thr Glu Phe Ala Phe
            340                 345                 350

Ser Val Leu Thr Ala Ala Val Lys Asn Asn Ile Leu Pro Val Ile Ala
            355                 360                 365

Met Gly Asn Glu Gly Arg Tyr Thr Ala Ala Tyr Pro Ala Ala Phe Pro
    370                 375                 380

Gly Met Leu Ala Val Gly Ala Thr Asn Gly Lys Asp Lys Lys Val His
385                 390                 395                 400

Phe Ser Asn Lys Gly Ala Trp Ile Ser Ile Ser Ala Pro Gly Asp Gly
                405                 410                 415

Ile Lys Ser Cys Gly Ile Ser Gly Asp Asp Asp Tyr Glu Thr Met Ser
                420                 425                 430

Gly Thr Ala Met Ala Thr Pro Phe Val Thr Gly Val Ile Ser Tyr Leu
            435                 440                 445

Leu Ser Phe Asn Asn Ala His Asn Leu Thr Pro Tyr Gln Ile Lys Ser
    450                 455                 460

Leu Leu Glu Lys Thr Ala Asp Lys Val Asp Gly Ala Val Ser Phe Thr
465                 470                 475                 480

Glu Gly Tyr Gly His Gly Arg Val Asn Val Tyr Asn Ala Ala Lys Ala
                485                 490                 495

Ile Arg Glu Asn Ser Ile Pro Gln Val Asn Glu Ile Tyr Ser Glu Gly
            500                 505                 510

Ser Val Tyr Val Glu Val Lys Asn Asn Glu Val Ile Ala Ser Lys
            515                 520                 525

Ile Ser Leu Val Asp Glu Glu Thr Lys Val Pro Leu Ala Tyr Val Ala
    530                 535                 540

Gly Leu Gly Asn Asn Pro Val Glu Phe Lys Gly Leu Val Lys Gly
545                 550                 555                 560

Lys Ser Tyr Ser Val Tyr Ala Ser Leu Leu Lys Tyr Ala Lys Lys Glu
                565                 570                 575

Thr Phe Thr Ala Asp Gly Ser Asp Lys Thr Val Thr Ile Gln Phe Asn
            580                 585                 590

Lys Asn Leu Ala Trp Val Ser Thr Val Pro Ser Leu His Tyr Asn Gly
            595                 600                 605

Gly Asn Glu Gln Pro Asp Thr Lys Ile Ile Val Phe Lys Ala Asp Ser
            610                 615                 620

Ser Gly Asn Leu Ser Arg Ser Pro Ser Pro Ile Leu Ile Tyr Asp Lys
625                 630                 635                 640

Asp Tyr Leu Asp Thr Ala Tyr Phe Glu Tyr Glu Ser Gly Ala Glu Tyr
                645                 650                 655

Tyr Ala Glu Ile Thr Gly Leu Lys Asp Glu Gln Gly Ile Phe Arg Gly
            660                 665                 670
```

```
Gly Asn Tyr Val Val Lys Ile Gly Leu Thr Pro Leu Asp Leu Asn Gly
            675                 680                 685

Glu Asp Ile Ile Asp Gly Ser Arg Val Ala Ser Asp Asn Asp Thr His
690                 695                 700

Glu Asp Asp Glu Pro Asp Lys Ala Lys Leu Lys Gly Asn Ala Trp
705                 710                 715                 720

Glu Lys Lys Tyr Ala Cys Asn Leu Ala Ala His Gly Thr Asn Asn Glu
            725                 730                 735

Asp Ile Asp Phe Phe Tyr Ile Lys Met Pro
            740                 745

<210> SEQ ID NO 2
<211> LENGTH: 346
<212> TYPE: PRT
<213> ORGANISM: Artificial Sequence
<220> FEATURE:
<223> OTHER INFORMATION: PrtP mature protein (PrtPM), T.pedis
<220> FEATURE:
<221> NAME/KEY: PEPTIDE
<222> LOCATION: (1)..(346)

<400> SEQUENCE: 2

Gly Asp Pro Ile Ala Asn Asn Ser Asp Tyr Gly Leu Ser Ile Thr Glu
1               5                   10                  15

Ala Leu Lys Ala Tyr Lys Glu Ile Gly Tyr Gly Asp Lys Thr Val Val
            20                  25                  30

Ala Gly Ile Ile Ala Thr Gly Ile Asn Met Thr His Lys Asp Phe Lys
        35                  40                  45

Asp Glu Asn Gly Asn Ser Ile Val Leu Tyr Ala Lys Ser Cys Val Lys
50                  55                  60

Ser Asn Gly Gly Thr Tyr Ile Gly Asn Gly Asn Pro Phe Thr Glu Ile
65                  70                  75                  80

Pro Ile Gly Glu Asn Trp Asp Lys Gly Ala Ala Gly Thr His Cys Ser
            85                  90                  95

Gly Thr Ile Cys Ala Arg Gly Asp Asn Asn Ala Gly Ile Ala Gly Val
            100                 105                 110

Ala Trp Lys Asn Thr Lys Leu Ile Ser Tyr Gln Ser Leu Asp Val Asp
            115                 120                 125

Gly Gly Gly Ser Ala Trp Ala Val Tyr Gly Ala Leu Ala Asp Leu Thr
        130                 135                 140

Arg Thr Val Asn Ile Leu Arg Lys Pro Lys Ser Asp Arg Thr Leu Asp
145                 150                 155                 160

Glu Asn Asn Ala Leu Pro Ser Tyr Leu Lys Asn Glu Asp Phe Gln Ile
            165                 170                 175

Thr Gln Lys Thr Val Pro Val Asn Met Ser Leu Gly Gly Ser Tyr Gly
            180                 185                 190

Thr Glu Phe Ala Phe Ser Val Leu Thr Ala Ala Val Lys Asn Asn Ile
        195                 200                 205

Leu Pro Val Ile Ala Met Gly Asn Glu Gly Arg Tyr Thr Ala Ala Tyr
        210                 215                 220

Pro Ala Ala Phe Pro Gly Met Leu Ala Val Gly Ala Thr Asn Gly Lys
225                 230                 235                 240

Asp Lys Lys Val His Phe Ser Asn Lys Gly Ala Trp Ile Ser Ile Ser
            245                 250                 255

Ala Pro Gly Asp Gly Ile Lys Ser Cys Gly Ile Ser Gly Asp Asp Asp
            260                 265                 270
```

```
Tyr Glu Thr Met Ser Gly Thr Ala Met Ala Thr Pro Phe Val Thr Gly
            275                 280                 285

Val Ile Ser Tyr Leu Leu Ser Phe Asn Asn Ala His Asn Leu Thr Pro
        290                 295                 300

Tyr Gln Ile Lys Ser Leu Leu Glu Lys Thr Ala Asp Lys Val Asp Gly
305                 310                 315                 320

Ala Val Ser Phe Thr Glu Gly Tyr Gly His Gly Arg Val Asn Val Tyr
                325                 330                 335

Asn Ala Ala Lys Ala Ile Arg Glu Asn Ser
            340                 345

<210> SEQ ID NO 3
<211> LENGTH: 261
<212> TYPE: PRT
<213> ORGANISM: Artificial Sequence
<220> FEATURE:
<223> OTHER INFORMATION: TlyC, T. pedis
<220> FEATURE:
<221> NAME/KEY: PEPTIDE
<222> LOCATION: (1)..(261)

<400> SEQUENCE: 3

Met Gly Leu Phe Asp Lys Phe Lys Lys Pro Asn Val Ser Gln Ile
1               5                   10                  15

Leu Lys Asn Gly Leu Asn Asp Glu Lys Arg Asp Met Ile Arg Gly Ile
            20                  25                  30

Val Asp Leu Ser Asp Thr Ala Val Lys Glu Val Met Ile Pro Arg Ile
        35                  40                  45

Asp Val Asp Phe Leu Ser Leu Asp Thr Pro Gly Asn Glu Ile Leu Asp
    50                  55                  60

Lys Ile Ser Glu Ser Gly His Ser Arg Phe Pro Val Tyr Glu Asp Ser
65                  70                  75                  80

Ile Asp Asn Val Ile Gly Ile Leu Tyr Val Lys Asp Ile Leu Lys Leu
                85                  90                  95

Leu Pro Lys Asn Glu Lys Ile Asp Leu Lys Lys Val Arg Lys Ala
            100                 105                 110

Phe Phe Val Pro Glu Ser Lys Arg Ile Asp Asp Leu Leu Arg Glu Phe
        115                 120                 125

Lys Arg Arg His Leu His Ile Ala Ile Ala Val Asp Glu Tyr Gly Gly
130                 135                 140

Thr Ser Gly Ile Val Cys Met Glu Asp Ile Ile Glu Glu Ile Val Gly
145                 150                 155                 160

Asp Ile Gln Asp Glu Phe Asp Asn Glu Gly Glu Asp Ile Thr Lys Ile
                165                 170                 175

Gly Glu Gly Val Trp Leu Cys Asp Ala Arg Ile Asp Leu Asp Asp Leu
            180                 185                 190

Lys Glu Ala Ile Asp Ala Glu Asp Leu Pro Ala Asp Glu Phe Glu Thr
        195                 200                 205

Leu Gly Gly Phe Val Phe Asp Leu Phe Gly Lys Ile Pro Val Lys Tyr
    210                 215                 220

Glu Lys Ala Val Trp Gln Asn Tyr Asp Phe Ile Val Gln Asp Met Asp
225                 230                 235                 240

Gly His Lys Val Lys Thr Val Lys Ile Ile Leu Asn Lys Glu Ala Leu
                245                 250                 255

Lys Pro Glu Ala Glu
            260
```

<210> SEQ ID NO 4
<211> LENGTH: 566
<212> TYPE: PRT
<213> ORGANISM: Artificial Sequence
<220> FEATURE:
<223> OTHER INFORMATION: MSP, T. pedis
<220> FEATURE:
<221> NAME/KEY: PEPTIDE
<222> LOCATION: (1)..(566)

<400> SEQUENCE: 4

```
Met Lys Lys Ile Leu Ser Ile Leu Ile Ala Leu Val Leu Val Gly Gly
1               5                   10                  15

Ala Val Phe Ala Gln Asp Ala Pro Glu Met Pro Ala Pro Val Phe Lys
            20                  25                  30

Gly Ser Ala Thr Leu Ser Trp Gly Ile Asp Leu Gly Tyr Gly Thr Asp
        35                  40                  45

Lys Tyr Gly Ser Ala Leu Ile Ser His Gly Phe Leu Asn Glu Ala Thr
    50                  55                  60

Ala Ser Val Ser Leu Pro Phe Val Lys Ser Gly Ser Lys Gly Glu
65                  70                  75                  80

Gly Asp Val Tyr Ala Leu Ile Asn Leu Asp Gly Val Lys Leu Gly Leu
                85                  90                  95

Glu Ala Asp Leu Lys Glu Ala Lys Ala Thr Gly Lys Ile Asp Lys Val
            100                 105                 110

Glu Ala Lys Ile Val Phe Tyr Gly Ala Tyr Ile Thr Val Tyr Asn Ala
        115                 120                 125

Pro Glu Met Lys Thr Lys Tyr Ala Ala Asp Ala Thr Ser Leu Ile Asn
    130                 135                 140

Asp Asp Asn Phe Gly Ile Phe Asn Ser Gly Phe Gly Gly Tyr Gly Thr
145                 150                 155                 160

Lys Ile Gly Tyr Ala Asn Pro Asp Leu Met Asp Leu Asp Val Gly Ile
                165                 170                 175

Lys Phe Thr Ser Asn Gly Ser Trp Lys Asp Arg Asp Gly Ser Leu Gly
            180                 185                 190

Ala Glu Tyr Val Lys Thr Val Thr Val Lys Ala Asn Arg Val Asn Gly
        195                 200                 205

Thr Gly Thr Val His Leu Glu Asp Gly Gln Glu Leu Arg Asp Met Ser
    210                 215                 220

Gly Lys Val Val Glu Arg Gly Pro Gly Trp Lys Arg Val Pro Ser Gly
225                 230                 235                 240

Gln Tyr Met Ile Tyr Arg Ser Ala Tyr Tyr Arg Tyr Arg Met Asn Gly
                245                 250                 255

His Tyr Gly Leu Gly Ile Asp Phe His Met Ala Pro Val Asp Lys Tyr
            260                 265                 270

Leu Thr Val Asp Ala Asn Phe Asn Met Thr Phe Asp Thr Ala Gly Ser
        275                 280                 285

Tyr Arg Thr Asp Val Glu Ser Asn Phe Asp Met Arg Val Met Asn
    290                 295                 300

Val Gly Ala Met Ile Lys Ser Glu Pro Ile Asp Gly Leu Met Phe Lys
305                 310                 315                 320

Leu Gly Phe Asp Gly Gly His Ala Lys Lys Ala Ser Asp Ala Ser
                325                 330                 335

Ala Pro Leu Phe Ala Trp Ala Leu Gly Phe Gly Thr Glu Tyr Lys Asp
            340                 345                 350
```

```
Ser Arg Ala Gly Thr Ile Asn Ala Gly Leu Tyr Val Ser Asp Gly
            355                 360                 365

Thr Pro Tyr Gly Asn Ala Gly Ile Phe Asp Pro Tyr Lys Leu Asn Phe
370                 375                 380

Val Pro Asp Gly Lys Gly Gly Phe Lys Glu Lys Arg Pro Asp Gly
385                 390                 395                 400

Thr Arg Pro Gly Arg Gly Ile Thr Asp Ile Ala Phe Thr Val Gly Tyr
                405                 410                 415

Ser Gly Leu Pro Ala Val Glu Gly Leu Asp Leu His Ala Arg Leu Asn
            420                 425                 430

Val Phe Gly Leu Leu Ser Lys Ile Ser Lys Glu Glu Arg Ala Met Gly
            435                 440                 445

Glu Leu Ile Pro Leu Gly Leu Asn Val Gly Ala Gly Tyr Lys Ala Met
450                 455                 460

Leu Thr Asp Ser Ile Trp Ile Lys Pro Tyr Ala Asp Leu Trp Gly Glu
465                 470                 475                 480

Thr Asn Ser Asp Ile Tyr Ser Asp Asp Thr Pro Lys Ser Lys Gln Lys
                485                 490                 495

Leu Tyr Phe Gly Leu Ala Tyr Lys Val Gly Leu Ser Val Ser Pro Met
            500                 505                 510

Glu Arg Leu Thr Ile Asp Leu Asn Trp Ser His Gly Lys Ala Phe Asn
            515                 520                 525

Pro Asp Val Leu Met Gly Thr Gly Ser Met Phe Gly Leu Gly Gln Trp
            530                 535                 540

Arg Ser Thr Pro Phe Gln His Lys Ala Asp Asn Gly Arg Phe Val Val
545                 550                 555                 560

Ser Ala Lys Ile Thr Tyr
                565

<210> SEQ ID NO 5
<211> LENGTH: 434
<212> TYPE: PRT
<213> ORGANISM: Artificial Sequence
<220> FEATURE:
<223> OTHER INFORMATION: OrfC, T. pedis
<220> FEATURE:
<221> NAME/KEY: PEPTIDE
<222> LOCATION: (1)..(434)

<400> SEQUENCE: 5

Met Gln Lys Ile Lys Lys Leu Ser Phe Val Phe Leu Phe Thr
1               5                   10                  15

Phe Ser Val Phe Ala Glu Phe Asn Phe Asp Leu Ile Val Gln Pro Phe
                20                  25                  30

Thr Gly Thr Glu Phe Phe Val Asp Gly Lys Thr Val Lys Pro Leu Val
            35                  40                  45

Leu Glu Lys Asp Asn Thr Leu Ala Lys Val Arg Leu Ile Leu Lys Asp
50                  55                  60

Ser Ala Ser Ala Ile Glu Val Lys Asn Lys Gly Phe Arg Thr Val Asn
65                  70                  75                  80

Leu Thr Asp Glu Leu Ile Arg Leu Lys Asn Asp Val Gly Lys Thr Ala
                85                  90                  95

Asp Leu Lys Ala Pro Phe Ser Ile Lys Ala Leu Ala Ile Leu Ser Arg
            100                 105                 110

Lys Glu Ser Lys Phe Asp Thr Lys Ala Phe Phe Pro Thr Gly Arg Gln
        115                 120                 125
```

```
Pro Lys Ser Val Thr Phe Val Asn Ser Asp Thr Val Ala Val Ala Leu
    130                 135                 140

Leu Asp Gly Asn Gly Ala Asp Ile Ile Asn Ile Glu Thr Gly Glu Lys
145                 150                 155                 160

Lys Arg Ile Ser Pro Pro Lys Glu Tyr Ala Glu Lys Leu Gly Phe Val
                165                 170                 175

Glu Ala Leu Val Leu Lys Asn Lys Asn Glu Leu Trp Ile Ser Gln Met
            180                 185                 190

Pro Thr Ala Leu Ile His Val Phe Asn Leu Thr Thr Phe Glu Tyr Lys
        195                 200                 205

Thr Ala Val Lys Thr Ser Gly Lys Trp Ser Lys Val Met Ala Tyr Asn
    210                 215                 220

Pro Leu Thr Asp Arg Val Tyr Leu Ser Asn Trp Gln Thr Phe Asp Ile
225                 230                 235                 240

Ser Val Ile Asn Thr Glu Thr Tyr Ser Glu Glu Lys Lys Ile Lys Thr
                245                 250                 255

Lys Ala Val Pro Arg Gly Met Ala Phe Ser Glu Asp Gly Lys Phe Ile
            260                 265                 270

Tyr Cys Ala Gln Phe Glu Asp Ala Ala Gly Asn Ser Asn Cys Arg Leu
        275                 280                 285

Val Lys Lys Glu Leu Asp Thr Phe Lys Thr Val Ser Glu Ser Gly Met
    290                 295                 300

Lys Gly Ala Lys Arg His Ile Val Thr Asp Tyr Lys Gln Gly Arg Leu
305                 310                 315                 320

Tyr Val Ser Asp Met Leu Asn Ala Val Ile Glu Val Tyr Ser Leu Lys
                325                 330                 335

Asp Glu Ser Leu Ile Lys Thr Val Lys Val Phe Ser His Pro Asn Thr
            340                 345                 350

Ile Gln Leu Ser Pro Asp Gly Lys Phe Leu Tyr Val Ser Cys Arg Gly
        355                 360                 365

Pro Asn Asn Pro Asp Lys Gly Tyr Leu Tyr Lys Gly Tyr Val Met Gly
    370                 375                 380

Arg Leu Asp Ile Ile Asp Thr Glu Thr Leu Thr Arg Ile Glu Ser Val
385                 390                 395                 400

Glu Ala Gly Asn Gln Pro Thr Gly Leu Asp Ile Ser Pro Asp Gly Lys
                405                 410                 415

Thr Ile Val Leu Ser Asp Phe Leu Asp Asn Arg Ile Arg Val Phe Lys
            420                 425                 430

Lys Asn

<210> SEQ ID NO 6
<211> LENGTH: 622
<212> TYPE: PRT
<213> ORGANISM: Artificial Sequence
<220> FEATURE:
<223> OTHER INFORMATION: PrtP, T. vincentii
<220> FEATURE:
<221> NAME/KEY: PEPTIDE
<222> LOCATION: (1)..(622)

<400> SEQUENCE: 6

Met Ile Lys Gln Lys Lys Phe Arg Phe Thr Leu Phe Phe Ile Thr Ser
1               5                   10                  15

Ala Leu Ala Ala Val Phe Ala Gly Cys Ala Met Gly Phe Val Asn Asn
            20                  25                  30

Ser Ala Lys Ser Asp Gly Thr Gly Ser Val His Gly Thr Ala Asp Ser
```

```
                35                  40                  45
Asn Thr Val Phe Asn Ser Lys Trp Ile Ile Ser Gln Gln Glu Arg His
 50                  55                  60
Asp Lys Gly Thr Val Val Arg Glu Gly Tyr Ser Ile Val Lys Thr Val
65                   70                  75                   80
Asp Ser Phe Asn Pro Asp Ser Phe Thr Ala Leu Asn Gly Ser Val Ala
             85                  90                  95
Ala Thr Gln Asp Leu His Asp Gly Tyr Leu Tyr Phe Leu Ile Lys Thr
            100                 105                 110
Glu Ser Asp Ala Ala Gln Phe Arg Thr Ala Val Arg Thr Leu Glu Gly
        115                 120                 125
Val Leu Tyr Ala Gln Pro Asp Tyr His Tyr Asp Ala Pro Ala Ala Met
        130                 135                 140
Val Asp Asn Thr Ala Arg Pro Pro Val Arg Asn Arg Gly Ala Ala Gly
145                 150                 155                 160
Lys Gly Thr Leu Gly Thr Ala Asp Gly Asn Leu Asp Asn Asp Pro Lys
                165                 170                 175
Ala Ala Leu Ala Asp Trp Gly Leu Thr Ala Thr Gly Ala Leu Glu Ala
            180                 185                 190
Phe Lys Arg Tyr Asp Ala Lys Tyr Pro Val Leu Ala Ala Ile Ile Asp
        195                 200                 205
Thr Gly Val Asn Ser Leu His Glu Asp Phe Tyr Asp Lys Asn Asn Lys
        210                 215                 220
Ser Ile Ile Leu Tyr Ala Lys Ser Ser Leu His Arg Gly Asp Val Thr
225                 230                 235                 240
Gln Tyr Thr Asn Pro Ile Pro Ile Ser Leu Asp Glu Asn Trp Asp Asn
                245                 250                 255
His Gly His Gly Thr His Cys Ser Gly Thr Ile Ala Ala Val Gly Asn
                260                 265                 270
Asn Gly Ile Gly Ile Cys Gly Val Ser His Ala Asn Thr Lys Leu Ile
            275                 280                 285
Thr Tyr Arg Gly Leu Asp Ala Ser Gly Gly Asp Thr Tyr Ala Thr Tyr
        290                 295                 300
Ser Cys Leu Gly Asp Leu Ala Glu Ile Ile Thr Glu Leu Arg Lys Glu
305                 310                 315                 320
Pro Gly Ser Arg Asn Ser Ala Val Phe Ala Gly Leu Pro Pro Asp Val
                325                 330                 335
Ile Asn Tyr Pro Gln Leu Arg Gln Lys Thr Val Pro Val Asn Leu Ser
            340                 345                 350
Leu Gly Gly Pro Ala Gly His Pro Tyr Glu Val Glu Met Met Asn Lys
        355                 360                 365
Ala Leu Ala Ala Gly Val Leu Pro Val Ile Ala Met Gly Asn Asp Gly
        370                 375                 380
Lys Thr Leu Ala Glu Tyr Pro Ala Ala Leu Gln Gly Ile Leu Ala Val
385                 390                 395                 400
Gly Ala Thr Thr Met Asp Asp Thr Arg Ala Ala Phe Ser Asn Gly Gly
                405                 410                 415
Thr Trp Met Ser Val Cys Ala Pro Gly Glu Ser Ile Tyr Ser Cys Gly
                420                 425                 430
Asn Gly Gly Gln Asn Trp Ala Asn Ser His Ser Pro Asp Val Lys Ser
            435                 440                 445
Ser Tyr Arg Trp Met Ser Gly Thr Ser Met Ala Thr Pro Phe Val Thr
        450                 455                 460
```

```
Gly Val Val Thr Tyr Leu Leu Ser Ile Asn Pro Asp Leu Ser Pro Tyr
465                 470                 475                 480

Gln Ile Lys Ala Leu Leu Glu Asn Thr Ala Asp Lys Ile Asp Arg Gly
                485                 490                 495

Ser Pro Tyr Gly Gln Tyr Asp Ser Arg Gly Phe Ser Lys Trp Tyr Gly
            500                 505                 510

Tyr Gly Arg Val Asn Val Leu Lys Ala Thr Glu Ala Leu Val Thr Gly
            515                 520                 525

Ser Asn Ile Pro Ala Glu Gly Ser Val Tyr Ser Glu Lys Ala Val Met
530                 535                 540

Ile Thr Leu Lys Lys Ala Gly Ala Ala Gln Lys Lys Thr Pro Val Trp
545                 550                 555                 560

Leu Tyr Glu Lys Ala Thr Gly Ile Cys Ala Ala Val Gly Leu Thr Asp
                565                 570                 575

Glu Thr Asn Gly Ile Val Arg Phe Tyr Gly Leu Arg Thr Gly Leu Glu
            580                 585                 590

Tyr Glu Ile Gly Val Asn Asp Ala Gly Thr Tyr Lys Thr Tyr Ile Ile
            595                 600                 605

Thr Ala Thr Asn Asp Ser Asp Ile Asp Tyr Thr Phe Leu Leu
            610                 615                 620

<210> SEQ ID NO 7
<211> LENGTH: 358
<212> TYPE: PRT
<213> ORGANISM: Artificial Sequence
<220> FEATURE:
<223> OTHER INFORMATION: PrtP mature protein (PrtPM), T. vincentii
<220> FEATURE:
<221> NAME/KEY: PEPTIDE
<222> LOCATION: (1)..(358)

<400> SEQUENCE: 7

Asn Asp Pro Lys Ala Ala Leu Ala Asp Trp Gly Leu Thr Ala Thr Gly
1               5                   10                  15

Ala Leu Glu Ala Phe Lys Arg Tyr Asp Ala Lys Tyr Pro Val Leu Ala
                20                  25                  30

Ala Ile Ile Asp Thr Gly Val Asn Ser Leu His Glu Asp Phe Tyr Asp
            35                  40                  45

Lys Asn Asn Lys Ser Ile Ile Leu Tyr Ala Lys Ser Ser Leu His Arg
50                  55                  60

Gly Asp Val Thr Gln Tyr Thr Asn Pro Ile Pro Ile Ser Leu Asp Glu
65                  70                  75                  80

Asn Trp Asp Asn His Gly His Gly Thr His Cys Ser Gly Thr Ile Ala
                85                  90                  95

Ala Val Gly Asn Asn Gly Ile Gly Ile Cys Gly Val Ser His Ala Asn
            100                 105                 110

Thr Lys Leu Ile Thr Tyr Arg Gly Leu Asp Ala Ser Gly Gly Asp Thr
        115                 120                 125

Tyr Ala Thr Tyr Ser Cys Leu Gly Asp Leu Ala Glu Ile Ile Thr Glu
130                 135                 140

Leu Arg Lys Glu Pro Gly Ser Arg Asn Ser Ala Val Phe Ala Gly Leu
145                 150                 155                 160

Pro Pro Asp Val Ile Asn Tyr Pro Gln Leu Arg Gln Lys Thr Val Pro
                165                 170                 175

Val Asn Leu Ser Leu Gly Gly Pro Ala Gly His Pro Tyr Glu Val Glu
            180                 185                 190
```

```
Met Met Asn Lys Ala Leu Ala Ala Gly Val Leu Pro Val Ile Ala Met
        195                 200                 205

Gly Asn Asp Gly Lys Thr Leu Ala Glu Tyr Pro Ala Ala Leu Gln Gly
    210                 215                 220

Ile Leu Ala Val Gly Ala Thr Thr Met Asp Asp Thr Arg Ala Ala Phe
225                 230                 235                 240

Ser Asn Gly Gly Thr Trp Met Ser Val Cys Ala Pro Gly Glu Ser Ile
                245                 250                 255

Tyr Ser Cys Gly Asn Gly Gly Gln Asn Trp Ala Asn Ser His Ser Pro
                260                 265                 270

Asp Val Lys Ser Ser Tyr Arg Trp Met Ser Gly Thr Ser Met Ala Thr
            275                 280                 285

Pro Phe Val Thr Gly Val Val Thr Tyr Leu Leu Ser Ile Asn Pro Asp
        290                 295                 300

Leu Ser Pro Tyr Gln Ile Lys Ala Leu Leu Glu Asn Thr Ala Asp Lys
305                 310                 315                 320

Ile Asp Arg Gly Ser Pro Tyr Gly Gln Tyr Asp Ser Arg Gly Phe Ser
                325                 330                 335

Lys Trp Tyr Gly Tyr Gly Arg Val Asn Val Leu Lys Ala Thr Glu Ala
                340                 345                 350

Leu Val Thr Gly Ser Asn
            355
```

<210> SEQ ID NO 8
<211> LENGTH: 216
<212> TYPE: PRT
<213> ORGANISM: Artificial Sequence
<220> FEATURE:
<223> OTHER INFORMATION: Hemolysin III, T. phagedenis
<220> FEATURE:
<221> NAME/KEY: PEPTIDE
<222> LOCATION: (1)..(216)

<400> SEQUENCE: 8

```
Met Thr Asn Lys Ile Lys Arg Arg Tyr Thr Val Gly Glu Glu Ile Ala
1               5                   10                  15

Asn Ala Ile Thr His Gly Val Gly Val Gly Leu Ser Ile Ala Ala Leu
            20                  25                  30

Val Leu Leu Ile Val Arg Ala Asn Arg Tyr Ala Pro Pro Glu Leu Lys
        35                  40                  45

Ala Gly Tyr Ile Val Gly Phe Ser Ile Phe Gly Ala Ser Leu Ile Ile
    50                  55                  60

Leu Tyr Leu Phe Ser Thr Leu Tyr His Ala Leu Pro Leu Gly Ala Lys
65                  70                  75                  80

Lys Val Phe Gln Ile Phe Asp His Cys Ser Ile Tyr Ile Leu Ile Ala
                85                  90                  95

Gly Thr Tyr Thr Ala Phe Cys Leu Thr Ala Leu His Gly Ala Ile Gly
            100                 105                 110

Trp Thr Ile Phe Gly Ile Ile Trp Gly Phe Ala Ile Ala Gly Ile Val
        115                 120                 125

Leu Tyr Ala Ile Phe Gln Asn Lys Phe Pro Ile Phe Ser Leu Ile Thr
    130                 135                 140

Tyr Ile Val Met Gly Trp Ile Ile Phe Ala Ala Arg Pro Leu Lys
145                 150                 155                 160

Ser Gln Leu Pro Ser Ile Ser Phe Leu Phe Leu Ile Leu Gly Gly Ile
                165                 170                 175
```

```
Val Tyr Thr Ala Gly Cys Ile Phe Phe Ala Leu Lys Lys Ile Arg Trp
            180                 185                 190

Met His Thr Ile Trp His Phe Phe Val Leu Gly Gly Ser Ile Leu His
            195                 200                 205

Phe Phe Ser Met Tyr Tyr Ser Leu
            210                 215

<210> SEQ ID NO 9
<211> LENGTH: 601
<212> TYPE: PRT
<213> ORGANISM: Artificial Sequence
<220> FEATURE:
<223> OTHER INFORMATION: Apr2, D. nodosus
<220> FEATURE:
<221> NAME/KEY: PEPTIDE
<222> LOCATION: (1)..(601)

<400> SEQUENCE: 9

Met Lys Arg Phe Ile Met Asn Lys Met Ala Leu Val Val Cys Ala Ala
1               5                   10                  15

Leu Val Gly Gln Val Ala Ser Ala Glu Thr Met Val Asn Tyr Ala Ser
            20                  25                  30

Ala Lys Ala Ile Gly Lys Gln Pro Ala Gly Ser Val Arg Phe Ile Val
        35                  40                  45

Lys Tyr Lys Asp Asn Ser Gln Ser Ser Lys Asp Leu Lys Asn Arg Ser
50                  55                  60

Thr Thr Lys Val Met Ala Asn Gly Met Gln Val Ala Gly Phe Asn Ala
65                  70                  75                  80

Gln Phe Val Arg Met Thr Gly Ala Gly Ala Gly Ile Phe Ser Val Pro
                85                  90                  95

Asp Leu Lys Thr Thr Lys Glu Ala His Leu Val Met Asp Thr Ile Ala
            100                 105                 110

Ser Asn Pro Asp Val Glu Phe Glu Val Asp Arg Ile Ala Arg Pro
            115                 120                 125

Thr Ala Ala Pro Asn Asp Gln His Tyr Arg Glu Gln Trp His Tyr Phe
    130                 135                 140

Asp Arg Tyr Gly Val Lys Ala Asp Lys Val Trp Asp Met Gly Phe Thr
145                 150                 155                 160

Gly Gln Asn Val Val Ala Val Asp Thr Gly Ile Leu His His
                165                 170                 175

Arg Asp Leu Asn Ala Asn Val Leu Pro Gly Tyr Asp Phe Ile Ser Asn
            180                 185                 190

Ser Gln Ile Ser Leu Asp Gly Asp Gly Arg Asp Ala Asp Pro Phe Asp
        195                 200                 205

Glu Gly Asp Trp Phe Asp Asn Trp Ala Cys Gly Gly Arg Pro Asp Pro
    210                 215                 220

Arg Lys Glu Arg Ser Asp Ser Ser Trp His Gly Ser His Val Ala Gly
225                 230                 235                 240

Thr Ile Ala Ala Val Thr Asn Asn Arg Ile Gly Val Ala Gly Val Ala
                245                 250                 255

Tyr Gly Ala Lys Val Val Pro Val Arg Ala Leu Gly Arg Cys Gly Gly
            260                 265                 270

Tyr Asp Ser Asp Ile Ser Asp Gly Leu Tyr Trp Ala Ala Gly Gly Arg
        275                 280                 285

Ile Ala Gly Ile Pro Glu Asn Arg Asn Pro Ala Lys Val Ile Asn Met
    290                 295                 300
```

Ser Leu Gly Ser Asp Gly Gln Cys Ser Tyr Asn Ala Gln Thr Met Ile
305                 310                 315                 320

Asp Arg Ala Thr Arg Leu Gly Ala Leu Val Val Ala Ala Gly Asn
            325                 330                 335

Glu Asn Gln Asn Ala Ser Asn Thr Trp Pro Thr Ser Cys Asn Asn Val
            340                 345                 350

Leu Ser Val Gly Ala Thr Thr Ser Arg Gly Ile Arg Ala Ser Phe Ser
            355                 360                 365

Asn Tyr Gly Val Asp Val Asp Leu Ala Ala Pro Gly Gln Asp Ile Leu
        370                 375                 380

Ser Thr Val Asp Ser Gly Thr Arg Arg Pro Val Ser Asp Ala Tyr Ser
385                 390                 395                 400

Phe Met Ala Gly Thr Ser Met Ala Thr Pro His Val Ser Gly Val Ala
                405                 410                 415

Ala Leu Val Ile Ser Ala Ala Asn Ser Val Asn Lys Asn Leu Thr Pro
            420                 425                 430

Ala Glu Leu Lys Asp Val Leu Val Ser Thr Thr Ser Pro Phe Asn Gly
        435                 440                 445

Arg Leu Asp Arg Ala Leu Gly Ser Gly Ile Val Asp Ala Glu Ala Ala
450                 455                 460

Val Asn Ser Val Leu Gly Asn Glu Gly Asn Asn Gly Arg Asp Asp Arg
465                 470                 475                 480

Arg Asp Asn Val Ala Pro Val Glu Asn Ala Arg Asn Tyr Ala Asn Asn
                485                 490                 495

Ser Ile Lys Phe Ile Arg Asp Tyr Arg Leu Thr Ser Ser Val Ile Glu
            500                 505                 510

Val Glu Gly Arg Ser Gly Ala Ala Asn Gly Lys Ile Asn Leu Ala Leu
        515                 520                 525

Asp Ile Arg His Gly Asn Arg Ser Gln Leu Ser Ile Gln Leu Thr Ser
530                 535                 540

Pro Ala Gly His Val Tyr His Ile Asn His Asp Gly Ala Arg Arg Pro
545                 550                 555                 560

Asn Leu Ser Gly Thr Val Glu Ile Pro Val Gln Asn Glu Gln Ile Asn
                565                 570                 575

Gly Ala Trp Val Leu Gln Val Gly Asp His Gly Arg Gly Ala Thr Gly
            580                 585                 590

Tyr Ile Lys Ser Trp Ser Leu Thr Leu
        595                 600

<210> SEQ ID NO 10
<211> LENGTH: 335
<212> TYPE: PRT
<213> ORGANISM: Artificial Sequence
<220> FEATURE:
<223> OTHER INFORMATION: Apr2 benign mature protein (Apr2BM), D. nodosus
<220> FEATURE:
<221> NAME/KEY: PEPTIDE
<222> LOCATION: (1)..(335)

<400> SEQUENCE: 10

Ala Ala Pro Asn Asp Gln His Tyr Arg Glu Trp His Tyr Phe Asp
1               5                   10                  15

Arg Tyr Gly Val Lys Ala Asp Lys Val Trp Asp Met Gly Phe Thr Gly
            20                  25                  30

Gln Asn Val Val Val Ala Val Val Ala Thr Gly Ile Leu His His Arg
        35                  40                  45

Asp Leu Asn Ala Asn Val Leu Pro Gly Tyr Asp Phe Ile Ser Asn Ser
    50                  55                  60

Gln Ile Ser Leu Asp Gly Asp Gly Arg Asp Ala Asp Pro Phe Asp Glu
65                  70                  75                  80

Gly Asp Trp Phe Asp Asn Trp Ala Cys Gly Gly Arg Pro Asp Pro Arg
                85                  90                  95

Lys Glu Arg Ser Asp Ser Ser Trp Ala Gly Ser His Val Ala Gly Thr
            100                 105                 110

Ile Ala Ala Val Thr Asn Asn Arg Ile Gly Val Ala Gly Val Ala Tyr
        115                 120                 125

Gly Ala Lys Val Val Pro Val Arg Ala Leu Gly Arg Cys Gly Gly Tyr
    130                 135                 140

Asp Ser Asp Ile Ser Asp Gly Leu Tyr Trp Ala Ala Gly Gly Arg Ile
145                 150                 155                 160

Ala Gly Ile Pro Glu Asn Arg Asn Pro Ala Lys Val Ile Asn Met Ser
                165                 170                 175

Leu Gly Ser Asp Gly Gln Cys Ser Tyr Asn Ala Gln Thr Met Ile Asp
            180                 185                 190

Arg Ala Thr Arg Leu Gly Ala Leu Val Val Ala Ala Gly Asn Glu
        195                 200                 205

Asn Gln Asn Ala Ser Asn Thr Trp Pro Thr Ser Cys Asn Asn Val Leu
    210                 215                 220

Ser Val Gly Ala Thr Thr Ser Arg Gly Ile Arg Ala Ser Phe Ser Asn
225                 230                 235                 240

Tyr Gly Val Asp Val Asp Leu Ala Ala Pro Gly Gln Asp Ile Leu Ser
                245                 250                 255

Thr Val Asp Ser Gly Thr Arg Arg Pro Val Ser Asp Ala Tyr Ser Phe
            260                 265                 270

Met Ala Gly Thr Ala Met Ala Thr Pro His Val Ser Gly Val Ala Ala
        275                 280                 285

Leu Val Ile Ser Ala Ala Asn Ser Val Asn Lys Asn Leu Thr Pro Ala
    290                 295                 300

Glu Leu Lys Asp Val Leu Val Ser Thr Thr Ser Pro Phe Asn Gly Arg
305                 310                 315                 320

Leu Asp Arg Ala Leu Gly Ser Gly Ile Val Asp Ala Glu Ala Ala
                325                 330                 335

<210> SEQ ID NO 11
<211> LENGTH: 603
<212> TYPE: PRT
<213> ORGANISM: Artificial Sequence
<220> FEATURE:
<223> OTHER INFORMATION: Bpr, D. nodosus
<220> FEATURE:
<221> NAME/KEY: PEPTIDE
<222> LOCATION: (1)..(603)

<400> SEQUENCE: 11

Met Asn Leu Ser Asn Ile Ser Ala Val Lys Val Leu Thr Leu Val Val
1               5                   10                  15

Ser Ala Ala Ile Ala Gly Gln Val Cys Ala Ala Glu Ser Ile Val Asn
            20                  25                  30

Tyr Glu Ser Ala Asn Ala Ile Ser Lys Gln Pro Glu Gly Ser Val Arg
        35                  40                  45

Phe Ile Val Lys Tyr Lys Asp Gly Thr Pro Ser Ser Gln Gly Leu Lys
    50                  55                  60

```
Thr Arg Ser Thr Thr Lys Val Met Ala Ser Gly Met Gln Val Ala Gly
 65                  70                  75                  80

Phe Glu Ala Gln Phe Val Arg Thr Thr Gly Leu Gly Ala Gly Ile Phe
                 85                  90                  95

Ala Val Pro Glu Leu Lys Thr Thr Lys Glu Ala His Leu Val Met Asp
            100                 105                 110

Thr Ile Ala Ser Asn Pro Asp Val Glu Phe Val Glu Val Asp Arg Leu
        115                 120                 125

Ala Tyr Pro Lys Ala Ala Pro Asn Asp Pro Ser Tyr Arg Gln Gln Trp
    130                 135                 140

His Tyr Phe Ser Asn Tyr Gly Val Lys Ala Asp Lys Val Trp Asp Arg
145                 150                 155                 160

Gly Phe Thr Gly Gln Gly Val Val Val Ser Val Val Asp Thr Gly Ile
                165                 170                 175

Leu Asp His Val Asp Leu Asn Gly Asn Met Leu Pro Gly Tyr Asp Phe
            180                 185                 190

Ile Ser Ser Ala Pro Lys Ala Arg Asp Gly Asp Gln Arg Asp Asn Asn
        195                 200                 205

Pro Ala Asp Glu Gly Asp Trp Phe Asp Asn Trp Asp Cys Gly Gly Tyr
    210                 215                 220

Pro Asp Pro Arg Arg Glu Lys Arg Phe Ser Thr Trp His Gly Ser His
225                 230                 235                 240

Val Ala Gly Thr Ile Ala Ala Val Thr Asn Asn Gly Val Gly Val Ala
                245                 250                 255

Gly Val Ala Tyr Gly Ala Lys Val Ile Pro Val Arg Val Leu Gly Lys
            260                 265                 270

Cys Gly Gly Tyr Asp Ser Asp Ile Thr Asp Gly Met Tyr Trp Ser Ala
        275                 280                 285

Gly Gly His Ile Asp Gly Val Pro Asp Asn Gln Asn Pro Ala Gln Val
    290                 295                 300

Ile Asn Met Ser Leu Gly Gly Asp Gly Asp Cys Ser Gln Ser Ser Gln
305                 310                 315                 320

Arg Ile Ile Asp Lys Thr Thr Asn Leu Gly Ala Leu Ile Val Ile Ala
                325                 330                 335

Ala Gly Asn Glu Asn Gln Asp Ala Ser Arg Thr Trp Pro Ser Ser Cys
            340                 345                 350

Asn Asn Val Leu Ser Val Gly Ala Thr Thr Pro Lys Gly Lys Arg Ala
        355                 360                 365

Pro Phe Ser Asn Tyr Gly Ala Arg Val His Leu Ala Ala Pro Gly Thr
    370                 375                 380

Asn Ile Leu Ser Thr Ile Asp Val Gly Gln Ala Gly Pro Val Arg Ser
385                 390                 395                 400

Ser Tyr Gly Met Lys Ala Gly Thr Ser Met Ala Ala Pro His Val Ser
                405                 410                 415

Gly Val Ala Ala Leu Val Ile Ser Ala Ala Asn Ser Ile Gly Lys Thr
            420                 425                 430

Leu Thr Pro Ser Glu Leu Ser Asp Ile Leu Val Arg Thr Thr Ser Arg
        435                 440                 445

Phe Asn Gly Arg Leu Asp Arg Gly Leu Gly Ser Gly Ile Val Asp Ala
    450                 455                 460

Asn Ala Ala Val Asn Ala Val Leu Gly Asp Gln Asn Arg Ala Gln Pro
465                 470                 475                 480
```

```
Arg Pro Pro Val Asn Gln Pro Ile Asn Ser Gly Asn Lys Val Tyr Arg
                485                 490                 495

Ser Asp Arg Arg Val Ala Ile Arg Asp Leu Arg Ser Val Thr Ser Gly
            500                 505                 510

Ile Arg Val Asn Asp Gln Ala Arg Val Gly Ser Ala Asn Ile Thr Leu
            515                 520                 525

Thr Leu Asp Ile Arg His Gly Asp Arg Ser Gln Leu Ala Val Glu Leu
            530                 535                 540

Ile Ala Pro Ser Gly Arg Val Tyr Pro Ile Tyr His Asp Gly Lys Arg
545                 550                 555                 560

Gln Pro Asn Ile Val Gly Pro Ala Thr Phe Ser Val Lys Asn Glu Arg
                565                 570                 575

Leu Gln Gly Thr Trp Thr Leu Lys Val Thr Asp Lys Ala Arg Gly Val
            580                 585                 590

Thr Gly Ser Ile Asp Ser Trp Ser Leu Thr Phe
            595                 600
```

```
<210> SEQ ID NO 12
<211> LENGTH: 335
<212> TYPE: PRT
<213> ORGANISM: Artificial Sequence
<220> FEATURE:
<223> OTHER INFORMATION: Bpr mature protein (BprM), D. nodosus
<220> FEATURE:
<221> NAME/KEY: PEPTIDE
<222> LOCATION: (1)..(335)

<400> SEQUENCE: 12

Ala Ala Pro Asn Asp Pro Ser Tyr Arg Gln Gln Trp His Tyr Phe Ser
1               5                   10                  15

Asn Tyr Gly Val Lys Ala Asp Lys Val Trp Asp Arg Gly Phe Thr Gly
            20                  25                  30

Gln Gly Val Val Ser Val Val Ala Thr Gly Ile Leu Asp His Val
            35                  40                  45

Asp Leu Asn Gly Asn Met Leu Pro Gly Tyr Asp Phe Ile Ser Ser Ala
        50                  55                  60

Pro Lys Ala Arg Asp Gly Asp Gln Arg Asp Asn Asn Pro Ala Asp Glu
65                  70                  75                  80

Gly Asp Trp Phe Asp Asn Trp Asp Cys Gly Gly Tyr Pro Asp Pro Arg
                85                  90                  95

Arg Glu Lys Arg Phe Ser Thr Trp Ala Gly Ser His Val Ala Gly Thr
            100                 105                 110

Ile Ala Ala Val Thr Asn Asn Gly Val Gly Val Ala Gly Val Ala Tyr
            115                 120                 125

Gly Ala Lys Val Ile Pro Val Arg Val Leu Gly Lys Cys Gly Gly Tyr
130                 135                 140

Asp Ser Asp Ile Thr Asp Gly Met Tyr Trp Ser Ala Gly Gly His Ile
145                 150                 155                 160

Asp Gly Val Pro Asp Asn Gln Asn Pro Ala Gln Val Ile Asn Met Ser
                165                 170                 175

Leu Gly Gly Asp Gly Asp Cys Ser Gln Ser Ser Gln Arg Ile Ile Asp
            180                 185                 190

Lys Thr Thr Asn Leu Gly Ala Leu Ile Val Ile Ala Ala Gly Asn Glu
            195                 200                 205

Asn Gln Asp Ala Ser Arg Thr Trp Pro Ser Ser Cys Asn Asn Val Leu
        210                 215                 220
```

```
Ser Val Gly Ala Thr Thr Pro Lys Gly Lys Arg Ala Pro Phe Ser Asn
225                 230                 235                 240

Tyr Gly Ala Arg Val His Leu Ala Ala Pro Gly Thr Asn Ile Leu Ser
                245                 250                 255

Thr Ile Asp Val Gly Gln Ala Gly Pro Val Arg Ser Ser Tyr Gly Met
            260                 265                 270

Lys Ala Gly Thr Ala Met Ala Ala Pro His Val Ser Gly Val Ala Ala
        275                 280                 285

Leu Val Ile Ser Ala Ala Asn Ser Ile Gly Lys Thr Leu Thr Pro Ser
290                 295                 300

Glu Leu Ser Asp Ile Leu Val Arg Thr Thr Ser Arg Phe Asn Gly Arg
305                 310                 315                 320

Leu Asp Arg Gly Leu Gly Ser Gly Ile Val Asp Ala Asn Ala Ala
                325                 330                 335

<210> SEQ ID NO 13
<211> LENGTH: 595
<212> TYPE: PRT
<213> ORGANISM: Artificial Sequence
<220> FEATURE:
<223> OTHER INFORMATION: Apr5, D. nodosus
<220> FEATURE:
<221> NAME/KEY: PEPTIDE
<222> LOCATION: (1)..(595)

<400> SEQUENCE: 13

Met Lys Gln Ser Gly Ile Asn Gly Val Lys Thr Leu Thr Leu Val Val
1               5                   10                  15

Cys Ala Ala Leu Ala Ser Gln Ala Tyr Ala Ala Val Asn Tyr Glu Ser
            20                  25                  30

Ala Asn Tyr Ile Gly Ser Gln Pro Glu Gly Ser Val Arg Phe Ile Ile
        35                  40                  45

Lys Tyr Lys Asp Lys Ser Gln Ser Gln Met Met Thr Asn Arg Ser
    50                  55                  60

Thr Thr Ser Val Met Asn Asn Asn Ile Thr Ile Ala Gly Phe Asn
65                  70                  75                  80

Ala Gln Phe Val Arg Thr Met Thr Ile Gly Ala Gly Ile Phe Ala Val
                85                  90                  95

Pro Asp Leu Lys Thr Thr Lys Glu Ala His Leu Val Met Asp Thr Ile
            100                 105                 110

Ala Ser Asn Pro Asp Val Glu Tyr Val Glu Val Asp Arg Trp Leu Arg
        115                 120                 125

Pro Phe Ala Ala Pro Asn Asp Pro Phe Tyr Asn Asp Gln Trp His Tyr
    130                 135                 140

Tyr Ser Glu Tyr Gly Val Lys Ala Asp Lys Val Trp Asp Arg Gly Ile
145                 150                 155                 160

Thr Gly Lys Gly Val Thr Val Ala Val Val Asp Thr Gly Ile Val Asn
                165                 170                 175

His Pro Asp Leu Asn Ala Asn Val Ile Pro Gly Ser Gly Tyr Asp Phe
            180                 185                 190

Ile Gln Glu Ala Glu Ile Ala Gln Asp Gly Asp Gly Arg Asp Ser Asn
        195                 200                 205

Pro Ala Asp Ala Gly Asp Trp His Ser Asn Trp Ala Cys Gly Lys Tyr
    210                 215                 220

Pro Asp Pro Arg Tyr Glu Lys Arg Asn Ser Ser Trp His Gly Ser His
225                 230                 235                 240
```

```
Val Ala Gly Thr Ile Ala Ala Val Thr Asn Arg Ile Gly Val Ser
            245                 250                 255

Gly Val Ala Tyr Asp Ala Lys Ile Val Pro Val Arg Val Leu Gly Arg
        260                 265                 270

Cys Gly Gly Tyr Asn Ser Asp Ile Asn Glu Gly Met Tyr Trp Ala Ala
        275                 280                 285

Gly Gly His Ile Asp Gly Val Pro Asp Asn Lys His Pro Ala Gln Val
        290                 295                 300

Ile Asn Met Ser Leu Gly Pro Gly Val Cys Gly Ser Thr Glu Gln
305                 310                 315                 320

Thr Leu Ile Asn Arg Ala Thr Gln Leu Gly Ala Thr Ile Ile Val Ala
                325                 330                 335

Ala Gly Asn Asp Asn Ile Asp Ala Tyr Gly Val Thr Pro Ala Ser Cys
                340                 345                 350

Asp Asn Ile Leu Thr Val Gly Ala Thr Thr Ser Asn Gly Thr Arg Ala
                355                 360                 365

Tyr Phe Ser Asn His Gly Ser Val Val Asp Ile Ser Ala Pro Gly Ala
370                 375                 380

Gly Ile Thr Ser Thr Val Asp Ser Gly Ala Arg Tyr Pro Ser Gly Pro
385                 390                 395                 400

Ser Tyr Ser Leu Met Asp Gly Thr Ser Met Ala Thr Pro His Val Ala
                405                 410                 415

Gly Val Ala Ala Leu Val Ile Ser Ala Ala Asn Ser Val Asn Lys Glu
                420                 425                 430

Met Thr Pro Ala Gln Val Arg Asp Val Leu Val Arg Thr Val Ser Ser
                435                 440                 445

Phe Asn Gly Thr Pro Asp Arg Arg Ile Gly Ala Gly Ile Val Asp Ala
450                 455                 460

Asp Ala Val Asn Ala Val Leu Asp Gly Asn Val Val Glu Arg Pro
465                 470                 475                 480

Ile Asp Glu Leu Lys Pro Gln Ala Glu Tyr Arg Asn Pro Gln Ile Lys
                485                 490                 495

Leu Ile Arg Asp Tyr Gln Met Met Phe Ser Glu Ile Lys Val Asn Gly
                500                 505                 510

Arg Pro Gly Asn Thr Lys Phe Ala Val Val Lys Ala Asp Ile Arg His
                515                 520                 525

Thr Asp Pro Ser Gln Leu Lys Leu Arg Leu Val Ser Pro Lys Gly Tyr
530                 535                 540

Glu Tyr Ala Val His Tyr Asp Asn Ile Lys Asn Lys Ser Ser Glu Leu
545                 550                 555                 560

Ile Thr Phe Pro Arg Asp Glu Gln Met Asn Gly Tyr Trp Arg Leu Lys
                565                 570                 575

Ile Val Asp Thr Lys Arg Gly Val Thr Gly Tyr Thr Arg Gly Trp Ser
                580                 585                 590

Val Ala Phe
        595

<210> SEQ ID NO 14
<211> LENGTH: 337
<212> TYPE: PRT
<213> ORGANISM: Artificial Sequence
<220> FEATURE:
<223> OTHER INFORMATION: Apr5 mature protein (Apr5M), D. nodosus
<220> FEATURE:
<221> NAME/KEY: PEPTIDE
<222> LOCAT

<400> SEQUENCE: 14

```
Ala Ala Pro Asn Asp Pro Phe Tyr Asn Asp Gln Trp His Tyr Tyr Ser
1               5                   10                  15
Glu Tyr Gly Val Lys Ala Asp Lys Val Trp Asp Arg Gly Ile Thr Gly
            20                  25                  30
Lys Gly Val Thr Val Ala Val Val Ala Thr Gly Ile Val Asn His Pro
        35                  40                  45
Asp Leu Asn Ala Asn Val Ile Pro Gly Ser Gly Tyr Asp Phe Ile Gln
    50                  55                  60
Glu Ala Glu Ile Ala Gln Asp Gly Asp Gly Arg Asp Ser Asn Pro Ala
65                  70                  75                  80
Asp Ala Gly Asp Trp His Ser Asn Trp Ala Cys Gly Lys Tyr Pro Asp
                85                  90                  95
Pro Arg Tyr Glu Lys Arg Asn Ser Ser Trp Ala Gly Ser His Val Ala
            100                 105                 110
Gly Thr Ile Ala Ala Val Thr Asn Asn Arg Ile Gly Val Ser Gly Val
        115                 120                 125
Ala Tyr Asp Ala Lys Ile Val Pro Val Arg Val Leu Gly Arg Cys Gly
130                 135                 140
Gly Tyr Asn Ser Asp Ile Asn Glu Gly Met Tyr Trp Ala Ala Gly Gly
145                 150                 155                 160
His Ile Asp Gly Val Pro Asp Asn Lys His Pro Ala Gln Val Ile Asn
                165                 170                 175
Met Ser Leu Gly Gly Pro Gly Val Cys Gly Ser Thr Glu Gln Thr Leu
            180                 185                 190
Ile Asn Arg Ala Thr Gln Leu Gly Ala Thr Ile Ile Val Ala Ala Gly
        195                 200                 205
Asn Asp Asn Ile Asp Ala Tyr Gly Val Thr Pro Ala Ser Cys Asp Asn
    210                 215                 220
Ile Leu Thr Val Gly Ala Thr Thr Ser Asn Gly Thr Arg Ala Tyr Phe
225                 230                 235                 240
Ser Asn His Gly Ser Val Val Asp Ile Ser Ala Pro Gly Ala Gly Ile
                245                 250                 255
Thr Ser Thr Val Asp Ser Gly Ala Arg Tyr Pro Ser Gly Pro Ser Tyr
            260                 265                 270
Ser Leu Met Asp Gly Thr Ala Met Ala Thr Pro His Val Ala Gly Val
        275                 280                 285
Ala Ala Leu Val Ile Ser Ala Ala Asn Ser Val Asn Lys Glu Met Thr
    290                 295                 300
Pro Ala Gln Val Arg Asp Val Leu Val Arg Thr Val Ser Ser Phe Asn
305                 310                 315                 320
Gly Thr Pro Asp Arg Arg Ile Gly Ala Gly Ile Val Asp Ala Asp Ala
                325                 330                 335
Ala
```

<210> SEQ ID NO 15
<211> LENGTH: 573
<212> TYPE: PRT
<213> ORGANISM: Artificial Sequence
<220> FEATURE:
<223> OTHER INFORMATION: Major Outer Sheath Protein (MSP), T. phagedenis
<220> FEATURE:
<221> NAME/KEY: PEPTIDE
<222> LOCATION: (1)..(573)

<400> SEQUENCE: 15

```
Met Lys Lys Tyr Leu Ile Ala Phe Ser Ile Phe Ala Phe Ala Leu Gly
1               5                   10                  15

Ile Ala Phe Ala Gln Glu Ala Glu Ala Ala Glu Pro Ala Gln Lys Ala
                20                  25                  30

Ala Ala Ala Glu Pro Ala Gln Lys Ala Ala Ala Ala Glu Pro Ala Lys
            35                  40                  45

Glu Pro Glu Val Tyr Ala Leu Thr Ser Gly Ala Lys Ala Ser Ile Glu
        50                  55                  60

Gly Ser Thr Lys Leu Glu Trp Gly Ile Asp Leu Gly Ala Gly Lys Val
65                  70                  75                  80

Thr Lys Asp Ser Ile Ala His Gly Phe Lys Asn Ser Gly Ser Trp Lys
                85                  90                  95

Val Ser Phe Pro Leu Phe Glu Lys Lys Ser Phe Thr Ser Lys Ala Asp
            100                 105                 110

Thr Pro Val Tyr Ala Glu Val Ile Ile Lys Asp Val Glu Leu Gly Ile
        115                 120                 125

Gln Ser Lys Asn Lys Ser Lys Lys Glu Lys Asp Phe Ala Phe Thr Gly
130                 135                 140

Lys Val Asp Glu Ile Val Gly Thr Leu Tyr Phe Tyr Asp Ala Tyr Leu
145                 150                 155                 160

Lys Ile Tyr Lys Lys Pro Gly Phe Lys Val Asn Tyr Ala Gln Ile Trp
                165                 170                 175

Asp Pro Leu Lys Ala Asp Asp Trp Asp Lys Ser Gly Tyr Lys Phe Glu
            180                 185                 190

Pro Gly Phe Asp Ile Ala Gly Gly Thr Thr Leu Gly Tyr Lys Lys Asp
        195                 200                 205

Asn Ile Gly Asn Ser Gly Leu Asp Leu Asp Ala Gly Val Lys Phe Gly
210                 215                 220

Ser Asn Gly Asn Trp Glu Thr Glu Gly Lys Ser Asp Tyr Glu Gly Ser
225                 230                 235                 240

Pro Gln Tyr Ala Leu Ile Thr Gly Pro Ala Thr Leu Ala Lys Gly Ser
                245                 250                 255

Thr Tyr Val Glu Leu Glu Pro Val Tyr Gly Lys Glu Ala Glu Glu Lys
            260                 265                 270

Ala Ser Tyr Ile Met Leu Asp Asn Gln Arg Phe Lys Ile Thr Ser Asn
        275                 280                 285

Phe Lys Lys Val Ser Pro Asp Lys Asp Leu Glu Val Lys Glu Gly Lys
290                 295                 300

Tyr Tyr Ala Lys Ile Asp Gly Leu Thr Lys Lys Asp Thr Pro Ala Thr
305                 310                 315                 320

Lys Asn Arg Tyr Gly Met Gly Phe Tyr Thr Ser Val Ala Tyr Lys Pro
                325                 330                 335

Gly Asp Leu Lys Tyr Ile Gly Phe Asn Phe Asp Ile Asn Thr Thr Phe
            340                 345                 350

Cys Ser His Lys Asp Trp Glu Asn Asn Thr Glu Lys Gly Asn Tyr Phe
        355                 360                 365

Asn Val Ser Phe Gly Thr Lys Ile Thr Ser Glu Pro Val Lys Asp Leu
370                 375                 380

Ser Leu Val Leu Ala Phe Asp Gly Glu Pro Phe Val Asn Gly Glu Lys
385                 390                 395                 400

Lys Phe Ala Trp Asp Met Leu Phe Asp Thr Thr Tyr Lys Trp Val Gly
                405                 410                 415
```

-continued

```
Ala Gly Val Tyr Val Gly Asn Glu Asn Thr Phe Tyr Lys Ser Asn Lys
            420                 425                 430

Asp Lys Val Asp Met Ser Ile Tyr Ala Lys Phe Glu Thr Lys Gly Asp
        435                 440                 445

Lys Lys Lys Ala Asn Phe Leu Val Glu Asn Leu Asn Ala Gly Ala Ala
        450                 455                 460

Ile Tyr Val His His Leu Leu Ser Lys Pro Val Ser Pro Lys Thr Val
465                 470                 475                 480

Pro Ile Gly Leu Lys Val Tyr Ala Asp Tyr Lys Tyr Asp Ile Asn Asp
                485                 490                 495

Ser Met Trp Leu Lys Pro Tyr Ala Ser Phe Tyr Gly Glu Thr Asn His
                500                 505                 510

Ala Glu Pro Lys Phe Gly Val Tyr Tyr Asn Val Gly Leu Thr Phe Ser
            515                 520                 525

Pro Leu Glu Arg Leu Glu Leu Thr Ala Asp Trp Glu Gln Gly Lys Val
        530                 535                 540

Val Lys Asn Lys His Glu Gly Phe Ile Glu Lys Ser Ala Gly Lys Glu
545                 550                 555                 560

His Asn Gly Arg Phe Lys Leu Gly Cys Lys Val Ser Phe
                565                 570
```

VACCINE COMPOSITIONS FOR USE AGAINST DIGITAL DERMATITIS IN A MAMMAL

STATEMENT REGARDING SEQUENCE LISTING

The Sequence Listing associated with this application is provided in text format in lieu of a paper copy, and is hereby incorporated by reference into the specification. The name of the text file containing the Sequence Listing is SEQUENCE_LISTING_450120_401USPC.txt. The text file is 60.3 KB, was created on May 15, 2020, and is being submitted electronically via EFS-Web.

FIELD OF THE INVENTION

This invention relates to the diagnosis and prevention or treatment of ungulate diseases where treponeme spirochetes bacteria are involved, in particular for the prophylactic treatment of digital dermatitis in a mammal, more particularly for bovine digital dermatitis. In addition, the present invention is directed to developing immunogenic compositions, diagnostic, therapeutic and making and administering a vaccine against digital dermatitis in a mammal.

BACKGROUND OF THE INVENTION

Digital dermatitis (DD) is a bacterial disease that primarily affects the skin on the heels of cattle. Infection causes inflammation and skin damage, leading to pain and discomfort. It is a major cause of lameness in cattle and most commonly seen in intensive dairy cows. Hence it is a significant problem for the dairy industry in many countries, causing reduced animal welfare and economic loss. DD has been identified as an emerging issue in beef cattle in the UK and the bacteria believed to cause DD have been identified in similar lesions in sheep (known as Contagious Ovine Digital Dermatitis), dairy goats and even wild North American Elk. In addition to this, these DD associated bacteria have been detected in three types of severe bovine foot lesions which have emerged during the last 15 years; toe necrosis, non-healing white line disease and non-healing sole ulcer. These developments highlight the growing importance of DD for domestic and wild animals, and for farmers and veterinarians.

Despite the economic and welfare importance of this disease, many questions remain regarding its etiology, transmission, prevention and treatment. There are a number of reasons why the disease is proving difficult to deal with; firstly, the infection appears to be poly-microbial, with a variety of bacteria, particularly of the genus *Treponema*, isolated from lesions. In addition, most of bacteria involved in DD initially proved difficult to grow in culture, experimental infection models have been difficult to develop, and the mechanisms of disease transmission have thus remained rather mysterious as well as the high recurrence rate in antibiotic cured cases. Recent advances in laboratory methods have provided some progress in the identification of the most important pathogenic bacteria, and in the detection of these bacteria in the animals and in the environment of farms with endemic DD.

A wide range of infection levels has been found on infected farms, prompting investigations into both farm/herd level risk factors and animal level risk factors (for example parity and stage of lactation) for DD occurrence. Both the farm level and animal level risk factors can provide useful information when trying to minimize DD infection levels and understand when risks of infection are highest. An interesting, but less investigated, aspect of DD is that there appears to be individual variation between animals in susceptibility to the disease. In this sense, several scientific publications forming part of the prior art all found that some animals within a herd were infected repeatedly while others of the same breed and parity and kept under the same conditions were never infected. If the reasons for this individual variation in susceptibility could be identified, they could add to our understanding of the disease and contribute to the search for effective prevention and treatment methods.

Determination of treponeme types or species associated with DD lesions has been based on DNA sequence analysis and classification. Evans et al., (Evans N. J., Brown J. M., Demirkan I., Murray R. D., Vink W. D., Blowey R. W., Hart C. A., Carter S. D. Three unique groups of spirochetes isolated from digital dermatitis lesions in UK cattle. Vet. Microbiol. 2008; 130:141-150), established the three most common phylotypes, *T. vincentii/T. medium*-like, *T. phagedenis*-like and *T. denticola/T. putidum*-like, clustered on 16S rDNA homology and flaB2 homology. Phylotypes (PT) are defined as clusters of treponemes in which the 16S rDNA sequence differs by ~2% from known species and which are ≥99% similar to other members of their cluster (Klitgaard K., Foix Breto A., Boye M., Jensen T. K. Targeting the treponemal microbiome of digital dermatitis infections by high-resolution phylogenetic analyses and comparison with fluorescent in situ hybridization. J. Clin. Microbiol. 2013; 51:2212-2219). Others have expanded the number of phylotypes up to seven including *T. brennaborense, T. maltophilum*-like (including *T. maltophilum* and *T. lecithinolyticum*), *T. refringens/T. calligyrum*-like, with *T. pedis* clustering with *T. denticola/T. putidum*.

Many bacteria of different genera other than *Treponema* spp., such as *Fusobacterium necrophorum, Dichelobacter nodosus, Prevotella* spp. and *Porphyromonas* spp. have also been isolated from DD lesions.

*Dichelobacter nodosus*, formerly known as *Bacteroides*, is a pathogenic, anaerobic, non-spore-forming Gram-negative bacteria. It has been detected in a number of DD lesions from different geographic locations. The findings of *D. nodosus* in lesions suggest that *D. nodosus* has a role in the pathogenesis of DD. It is also recognized as the primary agent involved in footrot in sheep.

*Fusobacterium necrophorum* is also a cause for lameness in cattle, sheep and other ruminants. It is an anaerobic bacteria. It has been mainly detected in the superficial keratinolyzed layers of the epidermis. It is suggested to be a secondary invader in DD lesions and footrot.

Several virulence factors have been described for pathogens involved in DD. For example, Nielsen M. W. et al., 2016 detected *Treponema* spp. virulence factors such as adhesins, surface antigens and proteins involved in motility. Other *Treponema* spp. virulence factors described are peptidases, proteases and haemolysins. Same type of virulence factors are described for other DD-associated pathogens, such as *D. nodosus* (Kennan, R. M., Dhungyel, O. P., Whittington, R. J., Egerton, J. R., & Rood, J. I. The Type IV Fimbrial Subunit Gene (fimA) of *Dichelobacter nodosus* Is Essential for Virulence, Protease Secretion, and Natural Competence. *Journal of bacteriology*, 2001, 183.15: 4451-4458).

Treatments for DD include systemic and topical antibiotics. In herds where a high proportion of animals are infected with DD individual treatment is very time-consuming, so many farmers use instead footbaths to treat the entire herd. Unfortunately, elimination of DD is rarely seen, so repeated application of treatments is required to prevent recurrence of infection. An antibody response is produced by dairy cows when they are infected with DD, however this response does not seem sufficient to prevent further infections, as some animals are infected repeatedly. One reason suggested for the difficulties encountered when trying to treat DD and prevent recurrence is the fact that a number of the treponemes thought to be involved in DD have been shown to have encysted as well as spiral forms. It is possible that these encysted forms of the bacteria could persist deep within the lesions and cause a recurrence of clinical disease at a later date, though more research is required to determine the significance of the encysted form of the bacteria and its response to DD treatments.

There have been a number of efforts over the last years to develop a vaccine against DD, however none of these vaccines are currently available. In this sense, Berry et al. (Berry S L, Ertze R A, Read D H, Hird D W. Field evaluation of prophylactic and therapeutic effects of a vaccine against (papillomatous) digital dermatitis of dairy cattle in 2 California dairies. Proc 16th Intl Symp Lameness in Ruminants, Slovenia, 2004) reported a study in two dairy herds in Nebraska where a different *Treponema* bacterin marketed as TrepShield® (Novartis Animal Health) was tested. The study concluded that the *Treponema* bacterin did not provide significant phophylactic or therapeutic effects in vaccinated animals. The vaccine (TrepShield®) has since been withdrawn.

Fiddler et al. (Fidler A. P., Alley M. L., Smith G. W. Evaluation of a *Serpens* species bacterin for treatment of digital dermatitis in dairy cattle. Res. Vet. Sci. 2012; 93:1258-1260. doi: 10.1016/j.rvsc.2012.07.002) reported the findings of a study which evaluated a vaccine containing *Serpens* sp. bacterin, developed by a commercial company. They found that, although the dairy cows involved in the trial did develop an immune response to the bacterin, there was no reduction in the prevalence or severity of DD infections among vaccinated cows when compared to controls. They therefore concluded that the vaccine did not show any clinical efficacy in terms of DD prevention.

In contrast and for the first time, the present invention provides new vaccine compositions comprising *Treponema* spp. bacterins, preferably supplemented with antigens from *Treponema* spp. or other digital dermatitis causative pathological agents such as *D. nodosus* or *F. necrophorum*, that effectively immunize susceptible mammals, preferably ungulates, against DD, in particular against bovine digital dermatitis.

BRIEF DESCRIPTION OF THE INVENTION

The present invention provides new vaccine compositions comprising *Treponema* spp. bacterins, preferably but not limited to *Treponema pedis* bacterins, optionally supplemented with antigens from *Treponema* spp. or other digital dermatitis causative pathological agents such as but not limited to *D. nodosus* or *F. necrophorum*, for effectively immunizing susceptible mammals, preferably ungulates, against DD, in particular against bovine digital dermatitis.

The present invention also identifies *Treponema pedis* as one of the etiologic agents of digital dermatitis (DD) in mammals, in particular ungulate digital dermatitis. The invention therefore also provides isolated cultures of *Treponema pedis* for effectively immunizing susceptible mammals, preferably ungulates, against DD, in particular against bovine digital dermatitis. In addition, the present invention provides methods of diagnosing DD by detecting infection with a series of specific *Treponema* antigens.

Thus in one aspect, the invention provides a biological, preferably a biologically pure, culture of *Treponema* spp. bacterins, preferably *Treponema pedis* bacterins, preferably supplemented with antigens from *Treponema* spp. or other digital dermatitis causative pathological agents such as *D. nodosus* or *F. necrophorum*, for effectively immunizing susceptible mammals, preferably ungulates, against DD, in particular against bovine digital dermatitis.

In another aspect, the invention provides a, preferably biologically pure culture of, preferably ungulate, *Treponema pedis* bacterins.

In another aspect, the invention provides a pharmaceutical composition comprising an immunogenically effective amount of *Treponema* spp. bacterins, preferably *Treponema pedis* bacterins, optionally supplemented with antigens, preferably recombinant antigens, from *Treponema* spp. or other digital dermatitis causative pathological agents such as *D. nodosus* or *F. necrophorum*, for effectively immunizing susceptible mammals, preferably ungulates, against DD, in particular against bovine digital dermatitis. Preferably, said antigens are *Treponema* antigens selected from the list consisting of MSP (Major Outer Sheath Protein), PrtP (Serine-protease Complex PrtP-like Protein), TlyC (Hemolysin C), OrfC (Surface Antigen OrfC Lipoprotein), and Hemolysin III. It is noted that all of these antigens can be obtained from *Treponema* spp. such as but not limited to *T. pedis, T. phagedenis*, or *T. vincentii*. Additional antigens useful in the present invention can be selected from other digital dermatitis causative pathological agents such as *D. nodosus* or *F. necrophorum*. All of these antigens can be used in combination in the pharmaceutical composition of the invention and are preferably recombinantly produced.

More preferably but not limited to, said proteins, polypeptides or antigens useful in the present invention are selected from virulence factors such as adhesins, peptidases, proteases, surface antigens, proteins involved in motility and haemolysins. Even more preferably said proteins, polypeptides or antigens useful in the present invention are selected from any of the following list:
MSP (Major Outer Sheath Protein);
PrtP (Serine-protease Complex PrtP-like Protein) and PrtPM (PrtP Mature Protein);
TylC (Hemolysin C);
OrfC (Surface Antigen OrfC Lipoprotein);
Haemolysin III;
Apr2 (Acidic Extracellular Subtilisin-like Protease Apr2) and Apr2BM (Apr2 Benign Mature Protein);
Apr5 (Acidic Extracellular Subtilisin-like Protease Apr5) and Apr5M (Apr5 Mature Protein);
Bpr (Basic Extracellular Subtilisin-like Protease Bpr) and BprM (Bpr Mature Protein);
PrcB (Serine-protease Complex PrcB-like protein);
PrcA (Serine-protease Complex PrcA-like protein);
Cys peptidase;
Hemolysin erythrocyte lysis protein 2;
Surface antigen BspA;
Filament protein;
Flagellar hook protein;
Prolyl endopeptidase;
Oligopeptidase;
Oligopeptidase B; and
Oligopeptidase F.

Still more preferably, said antigens are antigens from *Treponema pedis* selected from the list consisting of MSP, PrtP, preferably PrtPM, TlyC, and OrfC; and/or antigens MSP and Haemolysin III from *Treponema phagedenis*; and/or antigens PrtP, preferably PrtPM, from *Treponema vincentii*; and/or antigens Apr2, preferably Apr2BM, Apr5, preferably Apr5M, and Bpr, preferably BprM, from *Dichelobacter nodosus*, or any combination thereof, wherein optionally said antigens are recombinantly produced.

In addition, said pharmaceutical composition might further comprise an immunogenically effective amount of a bacterin selected from the group consisting of: *Treponema medium, Treponema vincentii, Treponema phagedenis, Treponema refringens, Treponema brennaborense, Treponema calligyrum,* and *Treponema maltophilum.*

In another aspect, the invention provides a method for inducing an immune response against the etiologic agents of digital dermatitis (DD) in mammals, in particular ungulate digital dermatitis. This method includes the step of administering to a mammal, preferably to an ungulate animal, the pharmaceutical composition as defined in the above paragraphs.

In one embodiment, the pharmaceutical composition further includes an antigen from an organism that causes ungulate footrot selected from the group consisting of *Fusobacterium necrophorum, Porphyromonas levii,* and *Dichelobacter nodosus*. In another embodiment, the pharmaceutical composition further comprises additional antigens such as a bovine respiratory syncytial virus antigen, a bovine herpes virus antigen, a leptospiral antigen, a bovine diarrhea virus antigen, a bovine parainfluenza virus antigen, a vesicular stomatitis virus antigen, a malignant catarrhal fever virus antigen, a blue tongue virus antigen, a pseudorabies virus antigen, a rabies virus antigen, a rinderpest virus antigen, a *Fusobacterium necrophorum* antigen, a *Dichelobacter nodosus* antigen, *Guggenheimella* antigen, *Porphyromonas* antigen, *Bacteroides* antigen, *Prevotella* antigen, Peptostreptococcus antigen, *Campylobacter* antigen, *Mycoplasma* antigen, *Corynebacterium/Actinomyces* antigen, *Cryptosporidium* antigen, Rotavirus antigen, Coronavirus antigen or a *Clostridium* spp. antigen.

In a still further aspect the *Treponema* spp. bacterins of the pharmaceutical composition are in the form of a suspension of killed or attenuated bacteria. Preferably, the *Treponema* bacterin is *T. pedis* bacterin in the form of a suspension of killed or attenuated bacteria. Preferably, the *T. pedis* bacterin is in the form of a killed bacteria suspension.

In another embodiment, the pharmaceutical composition of the invention further comprises a pharmaceutically acceptable carrier.

In another embodiment, the pharmaceutical composition of the invention is a vaccine.

In another embodiment, the pharmaceutical composition or the vaccine of the invention is administered parenterally.

In another embodiment the pharmaceutical composition or the vaccine of the invention is for use in a method of treatment or prevention of digital dermatitis; preferably, bovine digital dermatitis, contagious ovine digital dermatitis and/or footrot; more preferably, bovine digital dermatitis.

In another aspect, the invention provides a vaccination kit characterized in that it comprises a container comprising the pharmaceutical composition or the vaccine of the invention.

In another aspect, the invention provides a vaccination kit characterized in that it comprises an informative manual or leaflet which contains the information on administering said pharmaceutical composition or vaccine of the invention.

In another aspect, the invention provides a method for detecting the presence of antibodies specifically immunoreactive with a *Treponema* antigen, or with other digital dermatitis causative pathological agents such as *D. nodosus* or *F. necrophorum,* in a biological sample, the method comprising contacting the sample with an antigen selected from *Treponema* spp. antigens: MSP (Major Outer Sheath Protein), PrtP (Serine-protease Complex PrtP-like Protein), TlyC (Hemolysin C), OrfC (Surface Antigen OrfC Lipoprotein), or Hemolysin III. It is noted that all of these antigens can be obtained from *Treponema* spp. such as but not limited to *T. pedis, T. phagedenis,* or *T. vincentii*; and/or with antigens selected from other digital dermatitis causative pathological agents such as *D. nodosus* or *F. necrophorum,* thereby forming an antigen/antibody complex; and detecting the presence or absence of the complex. More preferably but not limited said proteins, polypeptides or antigens useful in the present methodology are selected from virulence factors such as adhesins, peptidases, proteases, surface antigens, proteins involved in motility and haemolysins. Even more preferably said antigens useful in the present methodology are selected from the following list:

MSP (Major Outer Sheath Protein);
PrtP (Serine-protease Complex PrtP-like Protein) and PrtPM (PrtP Mature Protein);
TylC (Hemolysin C);
OrfC (Surface Antigen OrfC Lipoprotein);
Haemolysin III;
Apr2 (Acidic Extracellular Subtilisin-like Protease Apr2) and Apr2BM (Apr2 Benign Mature Protein);
Apr5 (Acidic Extracellular Subtilisin-like Protease Apr5) and Apr5M (Apr5 Mature Protein);
Bpr (Basic Extracellular Subtilisin-like Protease Bpr) and BprM (Bpr Mature Protein);
PrcB (Serine-protease Complex PrcB-like protein);
PrcA (Serine-protease Complex PrcA-like protein);
Cys peptidase;
Hemolysin erythrocyte lysis protein 2;
Surface antigen BspA;
Filament protein;
Flagellar hook protein;
Prolyl endopeptidase;
Oligopeptidase;
Oligopeptidase B; and
Oligopeptidase F.

Still more preferably, said antigens are antigens from *Treponema pedis* selected from the list consisting of MSP, PrtP, preferably PrtPM, TlyC, and OrfC; and/or antigens MSP and Haemolysin III from *Treponema phagedenis*; and/or antigens PrtP, preferably PrtPM, from *Treponema vincentii*; and/or antigens Apr2, preferably Apr2BM, Apr5, preferably Apr5M, and Bpr, preferably BprM, from *Dichelobacter nodosus*, or any combination thereof; all of these antigens are particularly useful for forming an antigen/antibody complex; and thus for detecting the presence or absence of the complex.

In one embodiment, the biological sample is bovine serum. In another embodiment, the antigen is immobilized on a solid surface. In another embodiment, the complex is detected using a labeled anti-bovine antibody.

In another aspect, the invention provides a method of detecting the presence of ungulate *Treponema* in a biological sample or the presence of other ungulate digital dermatitis causative pathological agents such as *D. nodosus* or *F. necrophorum*. This method includes the steps of contacting the sample with an antibody specifically immunoreactive with an antigen selected from any of the above identified antigens, thereby forming an antigen/antibody complex; and detecting the presence or absence of the complex. Said method of detecting the presence of ungulate *Treponema* in a biological sample is useful for diagnosis or prognosis purposes, such as for diagnosis DD, particularly for diagnosing bovine digital dermatitis.

In another embodiment, the antibody is a monoclonal antibody. In another embodiment, the antibody is immobilized on a solid surface. In another embodiment, the complex is detected using a second labeled antibody. In another embodiment, the biological sample is ungulate foot tissue.

DETAILED DESCRIPTION OF THE INVENTION

Figure 1:
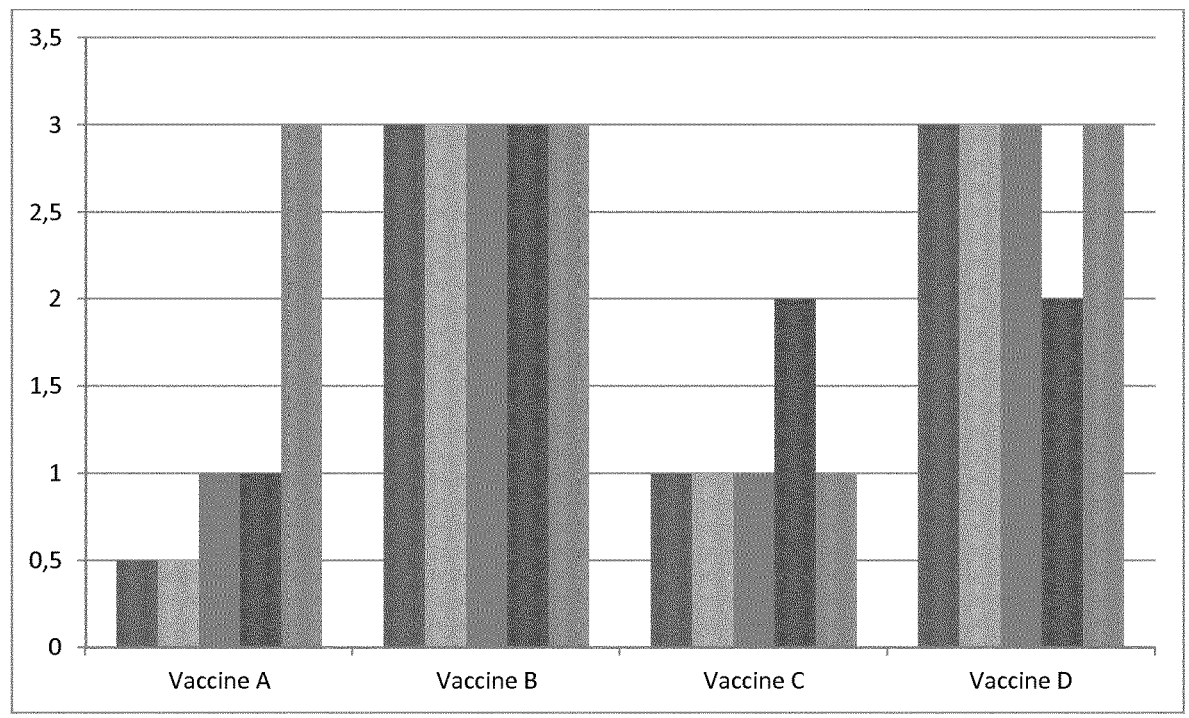
FIG. 1. Inhibition assay and indirect ELISA against *T. pedis* of sera obtained from cattle at day 47 post-vaccination (5 animals per group). A) Inhibition assay of *T. pedis* in a microplate (d47 pv) at dil. 1/32. Quantity of spiral forms (from 0 to 3) is shown as the ordinates for different tested vaccines, as the abscissas; B). Indirect ELISA against *T. pedis* at d47 post-vaccination. Optical density (OD) at 405 nm is shown, as the ordinates, for different tested vaccines, as the abscissas. Each vaccine is illustrated in example 1. Vaccine A (*Treponema pedis* bacterin+4 recombinant proteins); Vaccine B (4 recombinant proteins alone without *Treponema* bacterins); vaccine C (*Treponema pedis* bacterin alone), Vaccine D (placebo).
Figure 1:
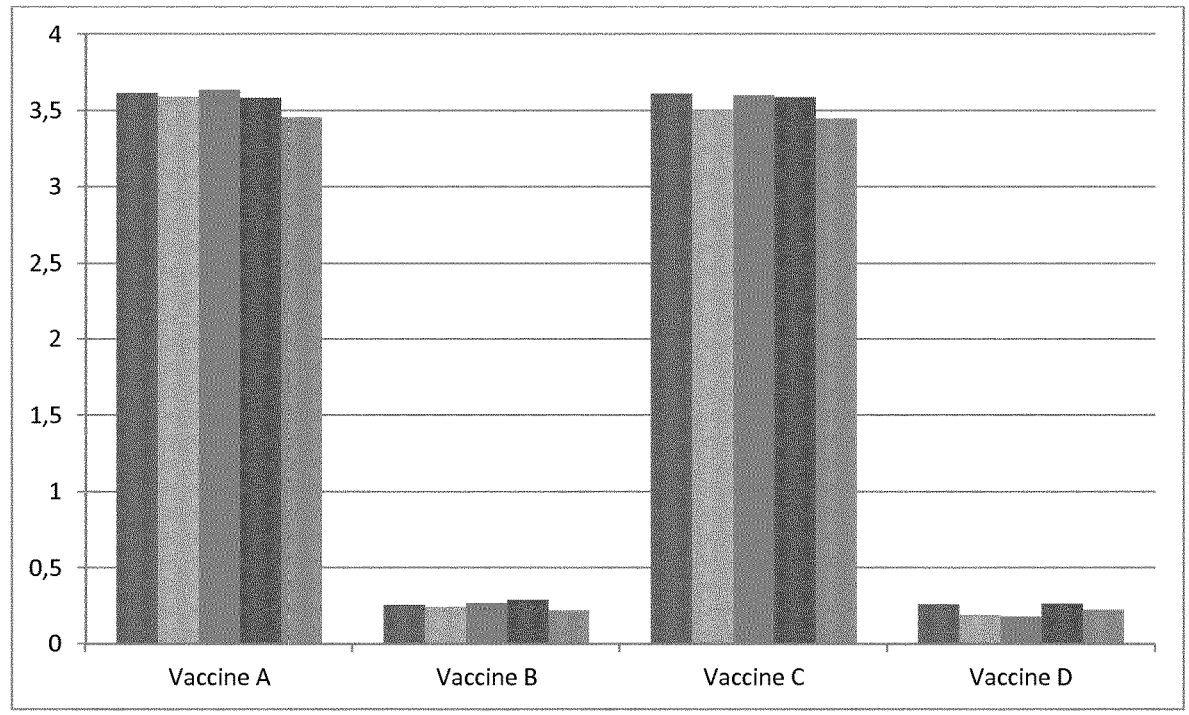

The present invention provides digital dermatitis, preferably bovine digital dermatitis, pharmaceutical or vaccine compositions having as active ingredients at least *Treponema* spp. bacterins; preferably an immunogenically effective amount of a bacterin selected from the group consisting of: *Treponema pedis*, *Treponema medium*, *Treponema vincentii*, *Treponema phagedenis*, *Treponema refringens*, *Treponema brennaborense*, *Treponema calligyrum*, and/or *Treponema maltophilum*. More preferably, an immunogenically effective amount of a bacterin selected from *Treponema pedis* and *Treponema phagedenis*. In addition, the present invention provides isolated antigens, preferably recombinant antigens, from *Treponema* spp. or other digital dermatitis causative pathological agents such as *D. nodosus* or *F. necrophorum*, in a variety of applications, including the production of nucleic acids and proteins for diagnostic assays for digital dermatitis and the preparation of immunogenic proteins and compositions for use in digital dermatitis vaccine compositions, wherein in these compositions said antigens are used in combination with an immunogenically effective amount of a *Treponema* spp. bacterin, preferably with an immunogenically effective amount of a *Treponema pedis* bacterins, or preferably with an immunogenically effective amount of a bacterin selected from the group consisting of: *Treponema medium*, *Treponema vincentii*, *Treponema phagedenis*, *Treponema refringens*, *Treponema brennaborense*, *Treponema calligyrum*, and *Treponema maltophilum*. In addition, in preferred embodiments of the present invention said isolated antigens are selected from virulence factors such as adhesins, peptidases, proteases, surface antigens, proteins involved in motility and haemolysisn. More preferably said isolated antigens are selected from the following list: MSP (Major Outer Sheath Protein), PrtP (Serine-protease Complex PrtP-like Protein) and PrtPM (PrtP Mature Protein), TylC (Hemolysin C), OrfC (Surface Antigen OrfC Lipoprotein), Haemolysin III, Apr2 (Acidic Extracellular Subtilisin-like Protease Apr2) and Apr2BM (Apr2 Benign Mature Protein), Apr5 (Acidic Extracellular Subtilisin-like Protease Apr5) and Apr5M (Apr5 Mature Protein), Bpr (Basic Extracellular Subtilisin-like Protease Bpr) and BprM (Bpr Mature Protein), PrcB (Serine-protease Complex PrcB-like protein), PrcA (Serine-protease Complex PrcA-like protein), Cys peptidase, Hemolysin erythrocyte lysis protein 2, Surface antigen BspA, Filament protein, Flagellar hook protein, Prolyl endopeptidase, Oligopeptidase, Oligopeptidase B, and Oligopeptidase F. Still more preferably said isolated antigens are selected from the list consisting of: MSP, PrtP, preferably PrtPM, TlyC, and OrfC from *Treponema pedis*; and/or antigens MSP and Haemolysin III from *Treponema phagedenis*; and/or antigens PrtP, preferably PrtPM, from *Treponema vincentii*; and/or antigens Apr2, preferably Apr2BM, Apr5, preferably Apr5M, and Bpr, preferably BprM, from *Dichelobacter nodosus*. As already stated, said antigens can be used in a variety of applications, including the production of nucleic acids and proteins for diagnostic assays for digital dermatitis and the preparation of immunogenic proteins and compositions for use in digital dermatitis vaccine compositions optionally comprising bacteria pertaining to the *Treponema* spp.

Definitions

As used herein, the following terms have the meanings ascribed to them unless specified otherwise.

"*Treponema*", "Ungulate *Treponema*" and "bovine *Treponema*" refer to flexible, spiral-shaped spirochete bacteria of the *Treponema* genus identified in or isolated from ungulate and bovine biological samples, in particular from hoof and foot tissue. The definition also relates to isolates of *Treponema*-like species from other origins such as ruminants, porcine, ovine, and/or human that are useful for preventing and/or treating digital dermatitis.

"Ungulate" refers to hooved animals such as cows, horses, sheep, and goats.

"Bovine" refers to cattle (bulls, cows, calves). Typically, the spirochetes of the *Treponema* genus can be isolated from foot or hoof tissue of hooved animals infected with DD (digital dermatitis).

"Bacterin" refers to a preparation of inactivated whole or partial bacteria cells suitable for use as a vaccine.

"*Treponema pedis*" was first described in bovine digital dermatitis lesions in Holstein-Friesian cows and was first deposited as *Treponema pedis* Evans et al. 2009, DSM No.: 18691, Type strain T3552B. In the present invention, the term "*Treponema pedis*" refers to any strains that belong to the species *T. pedis*, in particular to bacterial strains having a sequence identity over the whole 16S rRNA gene EF061268 (genebank accession number) of at least 90%, preferably of at least 99%. Other *Treponema* sources are also comprised in the definition. Therefore, any particular *Treponema* strain having a sequence identity over the whole 16S rRNA genes are also encompassed in the present invention. Some examples of *T. pedis* strains are T3552B, G819CB, T18B, T354A. Any *T. pedis* strain is suitable to be used in the present invention. Preferably, the strain used is *T. pedis* deposited by HIPRA SCIENTIFIC S.L.U. (Avda. La Selva, 135-Amer, Girona, Spain) in the Leibnitz-Institut DSMZ-Deutsche Sammlung von Mikroorganismen und Zellkulturen GmbH (Inhoffenstraße 7 B 38124 Braunschweig, Germany) under accession number DSM 32663 on Oct. 10, 2017.

"*Treponema medium*" refers to a bacterial species as defined in Umemoto T, Nakazawa F, Hoshino E, Okada K, Fukunaga M, Namikawa I. *Treponema medium* sp. nov., isolated from human subgingival dental plaque. Int J Syst Bacteriol. 1997 January; 47(1):67-72. The definition also encompasses isolates from *Treponema medium*-like species from other sources such as ruminant, porcine, ovine, human, etc. Some examples of *T. medium* strains are: T18A, T19, T35B1, 3C14, B-8307. Any *T. medium* strain is suitable to be used in the present invention.

"*Treponema phagedenis*" is described in Standards in Genomic Sciences 2015; https://doi.org/10.1186/s40793-015-0059-0, Mushtaq et al. 2015. In the present invention, the term "*Treponema phagedenis*" refers to any strains that belong to the species *T. phagedenis*, in particular to bacterial strains having a sequence identity over the whole 16S rRNA gene of *Treponema phagedenis*' strain V1 of at least 90%, at least 95%, at least 98%, preferably of at least 99%. Some examples of *T. phagedenis* strains are V1, V2, T413, T551B, T603, B-7330. Any *T. phagedenis* strain is suitable to be used in the invention. Preferably, the strain used is *T. phagedenis* deposited by HIPRA SCIENTIFIC S.L.U. (Avda. La Selva, 135-Amer, Girona, Spain) in the Leibnitz-Institut DSMZ-Deutsche Sammlung von Mikroorganismen und Zellkulturen GmbH (Inhoffenstraße 7 B 38124 Braunschweig, Germany) under accession number DSM 32950 on Nov. 7, 2018.

A *Treponema*, or other digital dermatitis causative pathological agents, "protein" or "polypeptide" or "antigen" refers to a polymer of amino acid residues and are not limited to a minimum length of the product. Peptides, oligopeptides, dimers, multimers are included in the definition. It includes allelic variations normally found in the natural population and changes introduced by recombinant techniques. Those of skill recognize that proteins can be modified in a variety of ways including the addition, deletion and substitution of amino acids. Specific *treponema*, or other digital dermatitis causative pathological agents, proteins, polypeptides or antigens useful in the present invention without any limitation are:

*T. pedis* "PrtP" (Serine-protease Complex PrtP-like Protein) and "PrtPM" (PrtP Mature Protein) proteins refers to a protein having at least 50%, at least 60%, at least 70%, at least 80%, at least 90%, at least 95%, at least 98%, preferably at least 99% sequence identity to SEQ ID NO: 1 or 2 respectively, or immunogenic fragments thereof.

```
SEQ ID NO 1 (PrtP, T. pedis):
MKKILVLSAVLAILAGSCSFNIDPQNISSNEQRVQSMEALYGNSSS

VIPYAPKDEDTVDGFFIVKTKDGFDKTAFEEKGFTVKGALPLTGTG

FTYWYLNKEGNDKKNLSVISSVKGVISAESDYKVEPPDGIKVAKTV

DGGGLVDISRLINGDYSGDPIANNSDYGLSITEALKAYKEIGYGDK

TVVAGIIATGINMTHKDFKDENGNSIVLYAKSCVKSNGGTYIGNGN

PFTEIPIGENWDKGAAGTHCSGTICARGDNNAGIAGVAWKNTKLIS

YQSLDVDGGGSAWAVYGALADLTRTVNILRKPKSDRTLDENNALPS

YLKNEDFQITQKTVPVNMSLGGSYGTEFAFSVLTAAVKNNILPVIA

MGNEGRYTAAYPAAFPGMLAVGATNGKDKKVHFSNKGAWISISAPG

DGIKSCGISGDDDYETMSGTAMATPFVTGVISYLLSFNNAHNLTPY

QIKSLLEKTADKVDGAVSFTEGYGHGRVNVYNAAKAIRENSIPQVN

EIYSEGSVYVEVKNNNEVIASKISLVDEETKVPLAYVAGLGNNPVV

EFKGLVKGKSYSVYASLLKYAKKETFTADGSDKTVTIQFNKNLAWV

STVPSLHYNGGNEQPDTKIIVFKADSSGNLSRSPSPILIYDKDYLD

TAYFEYESGAEYYAEITGLKDEQGIFRGGNYVVKIGLTPLDLNGED

IIDGSRVASDNDTHEDDDEPDKAKLKGNAWEKKYACNLAAHGTNNE

DIDFFYIKMP

SEQ ID NO 2 (PrtP mature protein (PrtPM),
T.pedis):
GDPIANNSDYGLSITEALKAYKEIGYGDKTVVAGIIATGINMTHKD

FKDENGNSIVLYAKSCVKSNGGTYIGNGNPFTEIPIGENWDKGAAG
```

THCSGTICARGDNNAGIAGVAWKNTKLISYQSLDVDGGGSAWAVYG

ALADLTRTVNILRKPKSDRTLDENNALPSYLKNEDFQITQKTVPVN

MSLGGSYGTEFAFSVLTAAVKNNILPVIAMGNEGRYTAAYPAAFPG

MLAVGATNGKDKKVHFSNKGAWISISAPGDGIKSCGISGDDDYETM

SGTAMATPFVTGVISYLLSFNNAHNLTPYQIKSLLEKTADKVDGAV

SFTEGYGHGRVNVYNAAKAIRENS

*T. pedis* "TlyC" (Hemolysin C) protein refers to a protein having at least 50%, at least 60%, at least 70%, at least 80%, at least 90%, at least 95%, at least 98%, preferably at least 99% sequence identity to SEQ ID NO: 3, or immunogenic fragments thereof.

```
SEQ ID NO 3 (TlyC, T. pedis):
MGLFDKFKKKPNVSQILKNGLNDEKRDMIRGIVDLSDTAVKEVMIP
```

RIDVDFLSLDTPGNEILDKISESGHSRFPVYEDSIDNVIGILYVKD

ILKLLPKNEKIDLKKVVRKAFFVPESKRIDDLLREFKRRHLHIAIA

VDEYGGTSGIVCMEDIIEEIVGDIQDEFDNEGEDITKIGEGVWLCD

ARIDLDDLKEAIDAEDLPADEFETLGGFVFDLFGKIPVKYEKAVWQ

NYDFIVQDMDGHKVKTVKIILNKEALKPEAE

*T. pedis* "MSP" (Major Outer Sheath Protein) refers to a protein having at least 50%, at least 60%, at least 70%, at least 80%, at least 90%, at least 95%, at least 98%, preferably at least 99% sequence identity to SEQ ID NO: 4, or immunogenic fragments thereof.

```
SEQ ID NO 4 (MSP, T. pedis):
MKKILSILIALVLVGGAVFAQDAPEMPAPVFKGSATLSWGIDLGYG
```

TDKYGSALISHGFLNEATASVSLPFVKSGSKKGEGDVYALINLDGV

KLGLEADLKEAKATGKIDKVEAKIVFYGAYITVYNAPEMKTKYAAD

ATSLINDDNFGIFNSGFGGYGTKIGYANPDLMDLDVGIKFTSNGSW

KDRDGSLGAEYVKTVTVKANRVNGTGTVHLEDGQELRDMSGKVVER

GPGWKRVPSGQYMIYRSAYYRYRMNGHYGLGIDFHMAPVDKYLTVD

ANFNMTFDTAGSYRTDVESNFDDMRVMNVGAMIKSEPIDGLMFKLG

FDGGHAFKKASDASAPLFAWALGFGTEYKDSRAGTINAGLYVSSDG

TPYGNAGIFDPYKLNFVPDGKGGFKEEKRPDGTRPGRGITDIAFTV

GYSGLPAVEGLDLHARLNVFGLLSKISKEERAMGELIPLGLNVGAG

YKAMLTDSIWIKPYADLWGETNSDIYSDDTPKSKQKLYFGLAYKVG

LSVSPMERLTIDLNWSHGKAFNPDVLMGTGSMFGLGQWRSTPFQHK

ADNGRFVVSAKITY

*T. pedis* "OrfC" (Surface Antigen OrfC Lipoprotein) refers to a protein having at least 50%, at least 60%, at least 70%, at least 80%, at least 90%, at least 95%, at least 98%, preferably at least 99% sequence identity to SEQ ID NO: 5, or immunogenic fragments thereof.

```
SEQ ID NO 5 (OrfC, T. pedis):
MQKIKKKLSFVFFLFTFSVPAEFNFDLIVQPFTGTEFFVDGKTVKP
```

LVLEKDNTLAKVRLILKDSASAIEVKNKGFRTVNLTDELIRLKNDV

GKTADLKAPFSIKALAILSRKESKFDTKAFFPTGRQPKSVTFVNSD

TVAVALLDGNGADIINIETGEKKRISPPKEYAEKLGFVEALVLKNK

NELWISQMPTALIHVFNLTTFEYKTAVKTSGKWSKVMAYNPLTDRV

YLSNWQTFDISVINTETYSEEKKIKTKAVPRGMAFSEDGKFIYCAQ

FEDAAGNSNCRLVKKELDTFKTVSESGMKGAKRHIVTDYKQGRLYV

SDMLNAVIEVYSLKDESLIKTVKVFSHPNTIQLSPDGKFLYVSCRG

PNNPDKGYLYKGYVMGRLDIIDTETLTRIESVEAGNQPTGLDISPD

GKTIVLSDFLDNRIRVFKKN

*T. vincentii* "PrtP" (Serine-protease Complex PrtP-like Protein) refers to a protein having at least 50%, at least 60%, at least 70%, at least 80%, at least 90%, at least 95%, at least 98%, preferably at least 99% sequence identity to SEQ ID NO: 6, or immunogenic fragments thereof.

```
SEQ ID NO 6 (PrtP, T. vincentii):
MIKQKKFRFTLFFITSALAAVFAGCAMGFVNNSAKSDGTGSVHGTA
```

DSNTVFNSKWIISQQERHDKGTVVREGYSIVKTVDSFNPDSFTALN

GSVAATQDLHDGYLYFLIKTESDAAQFRTAVRTLEGVLYAQPDYHY

DAPAAMVDNTARPPVRNRGAAGKGTLGTADGNLDNDPKAALADWGL

TATGALEAFKRYDAKYPVLAAIIDTGVNSLHEDFYDKNNKSIILYA

KSSLHRGDVTQYTNPIPISLDENWDNHGHGTHCSGTIAAVGNNGIG

ICGVSHANTKLITYRGLDASGGDTYATYSCLGDLAEIITELRKEPG

SRNSAVFAGLPPDVINYPQLRQKTVPVNLSLGGPAGHPYEVEMMNK

ALAAGVLPVIAMGNDGKTLAEYPAALQGILAVGATTMDDTRAAFSN

GGTWMSVCAPGESIYSCGNGGQNWANSHSPDVKSSYRWMSGTSMAT

PFVTGVVTYLLSINPDLSPYQIKALLENTADKIDRGSPYGQYDSRG

FSKWYGYGRVNVLKATEALVTGSNIPAEGSVYSEKAVMITLKKAGA

AQKKTPVWLYEKATGICAAVGLTDETNGIVRFYGLRTGLEYEIGVN

DAGTYKTYIITATNDSDIDYTFLL

*T. vincentii* "PrtPM" (PrtP Mature Protein) refers to a protein having at least 50%, at least 60%, at least 70%, at least 80%, at least 90%, at least 95%, at least 98%, preferably at least 99% sequence identity to SEQ ID NO: 7, or immunogenic fragments thereof.

```
SEQ ID NO 7 (PrtP mature protein (PrtPM),
T. vincentii):
NDPKAALADWGLTATGALEAFKRYDAKYPVLAAIIDTGVNSLHEDF
```

YDKNNKSIILYAKSSLHRGDVTQYTNPIPISLDENWDNHGHGTHCS

GTIAAVGNNGIGICGVSHANTKLITYRGLDASGGDTYATYSCLGDL

AEIITELRKEPGSRNSAVFAGLPPDVINYPQLRQKTVPVNLSLGGP

AGHPYEVEMMNKALAAGVLPVIAMGNDGKTLAEYPAALQGILAVGA

TTMDDTRAAFSNGGTWMSVCAPGESIYSCGNGGQNWANSHSPDVKS

SYRWMSGTSMATPFVTGVVTYLLSINPDLSPYQIKALLENTADKID

RGSPYGQYDSRGFSKWYGYGRVNVLKATEALVTGSN

*T. phagedenis* "Hemolysin III" refers to a protein having at least 50%, at least 60%, at least 70%, at least 80%, at least 90%, at least 95%, at least 98%, preferably at least 99% sequence identity to SEQ ID NO: 8, or immunogenic fragments thereof.

```
SEQ ID NO 8 (Hemolysin III, T. phagedenis):
MTNKIKRRYTVGEEIANAITHGVGVGLSIAALVLLIVRANRYAPPE

LKAGYIVGFSIFGASLIILYLFSTLYHALPLGAKKVFQIFDHCSIY

ILIAGTYTAFCLTALHGAIGWTIFGIIWGFAIAGIVLYAIFQNKFP

IFSLITYIVMGWIIIFAARPLKSQLPSISFLFLILGGIVYTAGCIF

FALKKIRWMHTIWHFFVLGGSILHFFSMYYSL
```

*D. nodosus* "Apr2" (Acidic Extracellular Subtilisin-like Protease Apr2) refers to a protein having at least 50%, at least 60%, at least 70%, at least 80%, at least 90%, at least 95%, at least 98%, preferably at least 99% sequence identity to SEQ ID NO: 9, or immunogenic fragments thereof.

```
SEQ ID NO 9 (Apr2, D. nodosus):
MKRFIMNKMALVVCAALVGQVASAETMVNYASAKAIGKQPAGSVRF

IVKYKDNSQSSKDLKNRSTTKVMANGMQVAGFNAQFVRMTGAGAGI

FSVPDLKTTKEAHLVMDTIASNPDVEFVEVDRIARPTAAPNDQHYR

EQWHYFDRYGVKADKVWDMGFTGQNVVVAVVDTGILHHRDLNANVL

PGYDFISNSQISLDGDGRDADPFDEGDWFDNWACGGRPDPRKERSD

SSWHGSHVAGTIAAVTNNRIGVAGVAYGAKVVPVRALGRCGGYDSD

ISDGLYWAAGGRIAGIPENRNPAKVINMSLGSDGQCSYNAQTMIDR

ATRLGALVVVAAGNENQNASNTWPTSCNNVLSVGATTSRGIRASFS

NYGVDVDLAAPGQDILSTVDSGTRRPVSDAYSFMAGTSMATPHVSG

VAALVISAANSVNKNLTPAELKDVLVSTTSPFNGRLDRALGSGIVD

AEAAVNSVLGNEGNNGRDDRRDNVAPVENARNYANNSIKFIRDYRL

TSSVIEVEGRSGAANGKINLALDIRHGNRSQLSIQLTSPAGHVYHI

NHDGARRPNLSGTVEIPVQNEQINGAWVLQVGDHGRGATGYIKSWS

LTL
```

*D. nodosus* "Apr2BM" (Apr2 Benign Mature Protein) refers to a protein having at least 50%, at least 60%, at least 70%, at least 80%, at least 90%, at least 95%, at least 98%, preferably at least 99% sequence identity to SEQ ID NO: 10, or immunogenic fragments thereof.

```
SEQ ID NO 10 (Apr2 benign mature protein
(Apr2BM), D. nodosus):
AAPNDQHYREQWHYFDRYGVKADKVWDMGFTGQNVVVAVVATGILH

HRDLNANVLPGYDFISNSQISLDGDGRDADPFDEGDWFDNWACGGR

PDPRKERSDSSWAGSHVAGTIAAVTNNRIGVAGVAYGAKVVPVRAL

GRCGGYDSDISDGLYWAAGGRIAGIPENRNPAKVINMSLGSDGQCS

YNAQTMIDRATRLGALVVVAAGNENQNASNTWPTSCNNVLSVGATT

SRGIRASFSNYGVDVDLAAPGQDILSTVDSGTRRPVSDAYSFMAGT
```

-continued
```
AMATPHVSGVAALVISAANSVNKNLTPAELKDVLVSTTSPFNGRLD

RALGSGIVDAEAA
```

*D. nodosus* "Bpr" (Basic Extracellular Subtilisin-like protease Bpr) refers to a protein having at least 50%, at least 60%, at least 70%, at least 80%, at least 90%, at least 95%, at least 98%, preferably at least 99% sequence identity to SEQ ID NO: 11, or immunogenic fragments thereof.

```
SEQ ID NO 11 (Bpr, D. nodosus):
MNLSNISAVKVLTLVVSAAIAGQVCAAESIVNYESANAISKQPEGS

VRFIVKYKDGTPSSQGLKTRSTTKVMASGMQVAGFEAQFVRTTGLG

AGIFAVPELKTTKEAHLVMDTIASNPDVEFVEVDRLAYPKAAPNDP

SYRQQWHYFSNYGVKADKVWDRGFTGQGVVVSVVDTGILDHVDLNG

NMLPGYDFISSAPKARDGDQRDNNPADEGDWFDNWDCGGYPDPRRE

KRFSTWHGSHVAGTIAAVTNNGVGVAGVAYGAKVIPVRVLGKCGGY

DSDITDGMYWSAGGHIDGVPDNQNPAQVINMSLGGDGDCSQSSQRI

IDKTTNLGALIVIAAGNENQDASRTWPSSCNNVLSVGATTPKGKRA

PFSNYGARVHLAAPGTNILSTIDVGQAGPVRSSYGMKAGTSMAAPH

VSGVAALVISAANSIGKTLTPSELSDILVRTTSRFNGRLDRGLGSG

IVDANAAVNAVLGDQNRAQPRPPVNQPINSGNKVYRSDRRVAIRDL

RSVTSGIRVNDQARVGSANITLTLDIRHGDRSQLAVELIAPSGRVY

PIYHDGKRQPNIVGPATFSVKNERLQGTWTLKVTDKARGVTGSIDS

WSLTF
```

*D. nodosus* "BprM" (Bpr Mature Protein) refers to a protein having at least 50%, at least 60%, at least 70%, at least 80%, at least 90%, at least 95%, at least 98%, preferably at least 99% sequence identity to SEQ ID NO: 12, or immunogenic fragments thereof.

```
SEQ ID NO 12 (Bpr mature protein (BprM),
D. nodosus):
AAPNDPSYRQQWHYFSNYGVKADKVWDRGFTGQGVVVSVVATGILD

HVDLNGNMLPGYDFISSAPKARDGDQRDNNPADEGDWFDNWDCGGY

PDPRREKRFSTWAGSHVAGTIAAVTNNGVGVAGVAYGAKVIPVRVL

GKCGGYDSDITDGMYWSAGGHIDGVPDNQNPAQVINMSLGGDGDCS

QSSQRIIDKTTNLGALIVIAAGNENQDASRTWPSSCNNVLSVGATT

PKGKRAPFSNYGARVHLAAPGTNILSTIDVGQAGPVRSSYGMKAGT

AMAAPHVSGVAALVISAANSIGKTLTPSELSDILVRTTSRFNGRLD

RGLGSGIVDANAA
```

*D. nodosus* "Apr5" (Acidic Extracellular Subtilisin-like Protease Apr5) refers to a protein having at least 50%, at least 60%, at least 70%, at least 80%, at least 90%, at least 95%, at least 98%, preferably at least 99% sequence identity to SEQ ID NO: 13, or immunogenic fragments thereof.

```
SEQ ID NO 13 (Apr5, D. nodosus):
MKQSGINGVKTLTLVVCAALASQAYAAVNYESANYIGSQPEGSVRF

IIKYKDKSQSQQMMTNRSTTSVMNNNNITIAGFNAQFVRTMTIGAG
```

-continued

```
IFAVPDLKTTKEAHLVMDTIASNPDVEYVEVDRWLRPFAAPNDPFY

NDQWHYYSEYGVKADKVWDRGITGKGVTVAVVDTGIVNHPDLNANV

IPGSGYDFIQEAEIAQDGDGRDSNPADAGDWHSNWACGKYPDPRYE

KRNSSWHGSHVAGTIAAVTNNRIGVSGVAYDAKIVPVRVLGRCGGY

NSDINEGMYWAAGGHIDGVPDNKHPAQVINMSLGGPGVCGSTEQTL

INRATQLGATIIVAAGNDNIDAYGVTPASCDNILTVGATTSNGTRA

YFSNHGSVVDISAPGAGITSTVDSGARYPSGPSYSLMDGTSMATPH

VAGVAALVISAANSVNKEMTPAQVRDVLVRTVSSFNGTPDRRIGAG

IVDADAAVNAVLDGNVVERPIDELKPQAEYRNPQIKLIRDYQMMFS

EIKVNGRPGNTKFAVVKADIRHTDPSQLKLRLVSPKGYEYAVHYDN

IKNKSSELITFPRDEQMNGYWRLKIVDTKRGVTGYTRGWSVAF
```

D. nodosus "Apr5M" (Apr5 Mature Protein) refers to a protein having at least 50%, at least 60%, at least 70%, at least 80%, at least 90%, at least 95%, at least 98%, preferably at least 99% sequence identity to SEQ ID NO: 14, or immunogenic fragments thereof.

SEQ ID NO 14 (Apr5 mature protein (Apr5M), *D. nodosus*):

AAPNDPFYNDQWHYYSEYGVKADKVWDRGITGKGVTVAVVATGIVN

HPDLNANVIPGSGYDFIQEAEIAQDGDGRDSNPADAGDWHSNWACG

KYPDPRYEKRNSSWAGSHVAGTIAAVTNNRIGVSGVAYDAKIVPVR

VLGRCGGYNSDINEGMYWAAGGHIDGVPDNKHPAQVINMSLGGPGV

CGSTEQTLINRATQLGATIIVAAGNDNIDAYGVTPASCDNILTVGA

TTSNGTRAYFSNHGSVVDISAPGAGITSTVDSGARYPSGPSYSLMD

GTAMATPHVAGVAALVISAANSVNKEMTPAQVRDVLVRTVSSFNGT

PDRRIGAGIVDADAA

SEQ ID NO 15 (Major Outer Sheath Protein (MSP), *T. phagedenis*):

MKKYLIAFSIFAFALGIAFAQEAEAAEPAQKAAAAEPAQKAAAAEP

AKEPEVYALTSGAKASIEGSTKLEWGIDLGAGKVTKDSIAHGFKNS

GSWKVSFPLFEKKSFTSKADTPVYAEVIIKDVELGIQSKNKSKKEK

DFAFTGKVDEIVGTLYFYDAYLKIYKKPGFKVNYAQIWDPLKADDW

DKSGYKFEPGFDIAGGTTLGYKKDNIGNSGLDLDAGVKFGSNGNWE

TEGKSDYEGSPQYALITGPATLAKGSTYVELEPVYGKEAEEKASYI

MLDNQRFKITSNFKKVSPDKDLEVKEGKYYAKIDGLTKKDTPATKN

RYGMGFYTSVAYKPGDLKYIGFNFDINTTFCSHKDWENNTEKGNYF

NVSFGTKITSEPVKDLSLVLAFDGEPFVNGEKKFAWDMLFDTTYKW

VGAGVYVGNENTFYKSNKDKVDMSIYAKFETKGDKKKANFLVENLN

AGAAIYVHHLLSKPVSPKTVPIGLKVYADYKYDINDSMWLKPYASF

YGETNHAEPKFGVYYNVGLTFSPLERLELTADWEQGKVVKNKHEGF

IEKSAGKEHNGRFKLGCKVSF

MSP (Major Outer Sheath Protein) *T. phagedenis* refers to a protein having at least 50%, at least 60%, at least 70%, at least 80%, at least 90%, at least 95%, at least 98%, preferably at least 99% sequence identity to SEQ ID NO: 15, or immunogenic fragments thereof.

Other candidate proteins, polypeptides or antigens useful in the present invention are selected from known virulence factors such as adhesins, peptidases, proteases, surface antigens, proteins involved in motility and haemolysins. Preferably selected from the following list:

PcrB (Serine-protease Complex PrcB-like protein);
PcrA (Serine-protease Complex PrcA-like protein);
Cys peptidase;
Hemolysin erythrocyte lysis protein 2;
Surface antigen BspA;
Filament protein;
Flagellar hook protein;
Prolyl endopeptidase;
Oligopeptidase;
Oligopeptidase B; and
Oligopeptidase F.

*Treponema*, or other digital dermatitis causative pathological agents, "nucleic acids" and "polynucleotides," as used herein, may be DNA or RNA. One of skill will recognize that for use in the expression of *Treponema* proteins or as diagnostic probes, polynucleotide sequences need not be identical and may be substantially identical to sequences disclosed here. In particular, where the inserted polynucleotide sequence is transcribed and translated to produce a functional polypeptide, one of skill will recognize that because of codon degeneracy a number of polynucleotide sequences will encode the same polypeptide.

"Biological sample" refers to any sample obtained from a living or dead organism. Examples of biological samples include biological fluids and tissue specimens. Examples of tissue specimens also include hoof and foot tissue. Such biological samples can be prepared for analysis using in situ techniques.

A "biologically pure culture" or "biological pure culture" refers to a continuous in vitro culture of ungulate *Treponema* which is substantially free of other organisms. A culture is substantially free of other organisms if standard harvesting procedures (as described below) result in a preparation which comprises at least about 90%, preferably 99% or more of the organism, e.g., *Treponema*.

"Percentage of sequence identity" for polynucleotides and polypeptides is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by computerized implementations of known algorithms (BLAST in the resources of the National Center for Biotechnology Information, CLUSTAL in the resources of the European Bioinformatics Institute, GAP, BESTFIT, FASTA, and TFASTA in the Wisconsin Genetics Software Package, Genetics Computer Group (GCG), 575 Science Dr., Madison, Wis.), or by inspection.

Substantial identity of polynucleotide sequences means that a polynucleotide comprises a sequence that has at least 75% sequence identity, preferably at least 80%, more preferably at least 90% and most preferably at least 95%. Typically, two polypeptides are considered to be substantially identical if at least 40%, preferably at least 60%, more preferably at least 90%, and most preferably at least 95% are identical or conservative substitutions. Sequences preferably compared to a reference sequence using GAP using default parameters.

Another indication that polynucleotide sequences are substantially identical is if two molecules hybridize to each other under stringent conditions. Stringent conditions are sequence dependent and will be different in different circumstances. Generally, stringent conditions are selected to be about 5 DEG C. lower than the thermal melting point (Tm) for the specific sequence at a defined ionic strength and pH. The Tm is the temperature (under defined ionic strength and pH) at which 50% of the target sequence hybridizes to a perfectly matched probe. Typically stringent conditions for a Southern blot protocol involve washing at room temperature with a 5.times.SSC, 0.1% SDS wash.

The phrase "specifically or selectively hybridizing to," refers to hybridization between a probe and a target sequence in which the probe binds substantially only to the target sequence, forming a hybridization complex, when the target is in a heterogeneous mixture of polynucleotides and other compounds. Such hybridization is determinative of the presence of the target sequence. Although the probe may bind other unrelated sequences, at least 90%, preferably 95% or more of the hybridization complexes formed are with the target sequence.

"Antibody" refers to an immunoglobulin molecule able to bind to a specific epitope on an antigen. Antibodies can be a polyclonal mixture or monoclonal. Antibodies can be intact immunoglobulins derived from natural sources or from recombinant sources and can be immunoreactive portions of intact immunoglobulins. Antibodies may exist in a variety of forms including, for example, Fv, Fab, and F(ab)2, as well as in single chains. Single-chain antibodies, in which genes for a heavy chain and a light chain are combined into a single coding sequence, may also be used.

"Immunogenic" or "immunological composition" refers to material which elicits an immunological response in the host of a cellular or antibody-mediated immune response type to the composition upon administration to a vertebrate, including humans. The immunogenic composition comprises molecules with antigenic properties, such as killed or attenuated bacteria or virus, among others and also immunogenic polypeptides. An immunogenic polypeptide is generally referred to as antigenic. A molecule is "antigenic" when it is capable of specifically interacting with an antigen recognition molecule of the immune system, such as an immunoglobulin (antibody) or T cell antigen receptor. An antigenic polypeptide contains an epitope of at least about five, and particularly at least about 10, at least 15, at least 20 or at least 50 amino acids. An antigenic portion of a polypeptide, also referred to as an epitope, can be that portion that is immunodominant for antibody or T cell receptor recognition, or it can be a portion used to generate an antibody to the molecule by conjugating the antigenic portion to a carrier polypeptide for immunization. The immunogenic composition relates according to this description, to the active molecule, composition comprising said molecule, or composition comprising more than one antigenic molecule to which a particular immune reaction is desired. Examples of immunogenic compositions include the supernatants of microorganism cultures, including bacteria, protozoa and viruses. Said supernatants contain those antigenic molecules of interest for initiating an immune response against thereto and that have been released (exotoxins) or delivered to the culture media where microorganisms grew and after the microorganism cells or particles (viruses) have been separated. The supernatants are also termed herewith as cell-free preparations.

"Antigen" refers to a molecule against which a subject can initiate an immune response, e.g. a humoral and/or cellular immune response. Depending on the intended function of the composition, one or more antigens may be included.

"Immunologically effective amount," or "immunologically effective dose" means the administration of that amount or dose of antigen, either in a single dose or as part of a series, that elicits, or is able to elicit, an immune response that reduces the incidence of or lessens the severity of infection or incident of disease in an animal for either the treatment or prevention of disease. The immunologically effective amount or effective dose is also able for inducing the production of antibody for either the treatment or prevention of disease. This amount will vary depending upon a variety of factors, including the physical condition of the subject, and can be readily determined by someone of skill in the art.

"Vaccine" as used herein, means an immunogenic composition of the invention accompanied by adequate excipients and/or carriers, that when administered to an animal, elicits, or is able to elicit, directly or indirectly, an immune response in the animal. Particularly, the vaccines of the present invention elicit an immunological response in the host of a cellular or antibody-mediated type upon administration to the subject that it is protective. The term "combination vaccine" means that the vaccine contains various antigens in a single preparation, protecting against two or more diseases or against one disease caused by two or more microorganisms. Thus the vaccine includes as "active principle" an "immunogenic composition", according to the invention.

"Medicament" as used herein is synonymous of a pharmaceutical or veterinary drug (also referred to as medicine, medication, or simply drug) use to cure, treat or prevent disease in animals, including humans, as widely accepted. Drugs are classified in various ways. One key distinction is between traditional small-molecule drugs, usually derived from chemical synthesis, and biopharmaceuticals, which include recombinant proteins, vaccines, blood products used therapeutically (such as IVIG), gene therapy, monoclonal antibodies and cell therapy (for instance, stem-cell therapies). In the present invention medicament preferably is a veterinary medicament, and even more preferably is a vaccine for veterinary use.

The phrase "specifically immunoreactive with", when referring to a protein or peptide, refers to a binding reaction between the protein and an antibody which is determinative of the presence of the protein in the presence of a heterogeneous population of proteins and other compounds. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein and are described in detail below.

The phrase "substantially pure" or "isolated" when referring to a *Treponema* peptide or protein, means a chemical composition which is free of other subcellular components of the *Treponema* organism. Typically, a monomeric protein is substantially pure when at least about 85% or more of a sample exhibits a single polypeptide backbone. Minor variants or chemical modifications may typically share the same polypeptide sequence. Depending on the purification procedure, purities of 85%, and preferably over 95% pure are possible. Protein purity or homogeneity may be indicated by a number of means well known in the art, such as polyacrylamide gel electrophoresis of a protein sample, followed by visualizing a single polypeptide band on a polyacrylamide gel upon silver or Coomasie staining. For certain purposes high resolution will be needed and HPLC, FPLC or a similar means for purification utilized.

A "label" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, dioxigenin, or haptens and proteins for which antisera or monoclonal antibodies are available.

The term "recombinant" when used with reference to a cell, or nucleic acid, or vector, indicates that the cell, or nucleic acid, or vector, has been modified by the introduction of a heterologous nucleic acid or the alteration of a native nucleic acid, or that the cell is derived from a cell so modified. Thus, for example, recombinant cells express genes that are not found within the native (non-recombinant) form of the cell or express native genes that are otherwise abnormally expressed, under expressed or not expressed at all.

"Pharmaceutically acceptable" means a material that is not biologically or otherwise undesirable, i.e., the material can be administered to an individual along with a *Treponema* antigen without causing any undesirable biological effects or interacting in a deleterious manner with any of the other components of the pharmaceutical composition.

"Preventing", "to prevent" or "prevention", include without limitation, decreasing, reducing or ameliorating the risk of a symptom, disorder, condition, or disease, and protecting an animal from a symptom, disorder, condition, or disease. A prevention may be applied or administered prophylactically.

"Treating", "to treat" or "treatment", include without limitation, restraining, slowing, stopping, reducing, ameliorating, or reversing the progression or severity of an existing symptom, clinical sign, disorder, condition, or disease. A treatment may be applied or administered therapeutically.

"Subject" means an individual. In one aspect, a subject is a mammal such as a primate, including humans. In another aspect, the mammal is a non-human primate such as marmosets, monkeys, chimpanzees, gorillas, orangutans and gibbons among others. The term "subject" also includes domesticated animals such as cats, dogs, etc.; livestock such as for example cattle, horses, pigs, sheep, goats, etc.; laboratory animals for example ferret, chinchilla, mouse, rabbit, rat, gerbil, guinea pig, etc.; and avian species such as chicken, turkeys, ducks, pheasants, pigeons, doves, parrots, cockatoos, geese, etc. Subjects can also include, but are not limited to fish (for example, zebrafish, goldfish, tilapia, salmon and trout), amphibians and reptiles. As used herein, a "subject" is the same as a "patient" or "affected subject", and the terms can be used interchangeably.

Description

The present invention provides new pharmaceutical and/or vaccine compositions comprising *Treponema* spp. bacterins, optionally supplemented with antigens from *Treponema* spp. or other digital dermatitis causative pathological agents such as *D. nodosus* or *F. necrophorum*. Said vaccine compositions are preferably for effectively immunizing susceptible mammals, preferably ungulates, against DD, in particular against bovine digital dermatitis, and wherein said *Treponema* spp. bacterins are preferably selected from *T. pedis, T. phagedenis, T. vincentii, T. medium, T. refringens, T. calligyrum, T. maltophilum* and/or *T. brennaborense*, preferably from *T. pedis* or *T. phagedenis*.

In addition, the present invention provides isolated antigens, preferably recombinant antigens, from *Treponema* spp. or other digital dermatitis causative pathological agents such as *D. nodosus* or *F. necrophorum*, in a variety of applications, including the production of nucleic acids and proteins for diagnostic assays for digital dermatitis and the preparation of immunogenic proteins and compositions for use in digital dermatitis vaccine compositions, wherein in these compositions said antigens are used in combination with an immunogenically effective amount of a *Treponema* spp. bacterin, preferably with an immunogenically effective amount of a *Treponema pedis* bacterins, or preferably with an immunogenically effective amount of a bacterin selected from the group consisting of: *Treponema medium, Treponema vincentii, Treponema phagedenis, Treponema refringens, Treponema brennaborense, Treponema calligyrum,* and *Treponema maltophilum*, or any combination thereof. In a preferred embodiment, said antigens are isolated antigens from *Treponema* spp. such us but not limited to *T. pedis*, selected from the list consisting of MSP (Major Outer Sheath Protein), PrtP (Serine-protease Complex PrtP-like Protein), TlyC (Hemolysin C), OrfC (Surface Antigen OrfC Lipoprotein), and Hemolysin III. In a more preferred embodiment, said antigens are isolated antigens from *Treponema pedis* and are selected from the list consisting of MSP (Major Outer Sheath Protein), PrtP (Serine-protease Complex PrtP-like Protein), preferably PrtPM (PrtP Mature Protein), TlyC (Hemolysin C), and OrfC (Surface Antigen OrfC Lipoprotein); and/or antigens MSP and Haemolysin III from *Treponema phagedenis*; and/or antigens PrtP, preferably PrtPM, from *Treponema vincentii*; and/or antigens Apr2 (Acidic Extracellular Subtilisin-like Protease Apr2), preferably Apr2BM (Apr2 Benign Mature Protein), Apr5 (Acidic Extracellular Subtilisin-like Protease Apr5), preferably Apr5M (Apr5 Mature Protein), and Bpr (Basic Extracellular Subtilisin-like Protein Bpr), preferably BprM (Bpr Mature Protein), from *Dichelobacter nodosus*; as well as other candidate proteins, polypeptides or antigens useful in the present invention selected from virulence factors such as adhesins, peptidases, proteases, surface antigens, proteins involved in motility, and haemolysins. In yet another preferred embodiment, said polypeptides or antigens useful in the present invention can be selected from the following list:

PcrB (Serine-protease Complex PrcB-like protein);
PcrA (Serine-protease Complex PrcA-like protein);
Cys peptidase;
Hemolysin erythrocyte lysis protein 2;
Surface antigen BspA;
Filament protein;
Flagellar hook protein;
Prolyl endopeptidase;
Oligopeptidase;
Oligopeptidase B; and
Oligopeptidase F;

and use in a variety of applications, including the production of nucleic acids and proteins for diagnostic assays for digital dermatitis and the preparation of immunogenic proteins and compositions for use in digital dermatitis vaccine compositions optionally comprising bacteria pertaining to the *Treponema* spp. Preferably, the above said digital dermatitis vaccine compositions comprising bacteria pertaining to the *Treponema* spp., comprise at least one or more of the following *treponema* species: *T. pedis, T. phagedenis, T. vincentii, T. medium, T. refringens, T. calligyrum, T. maltophilum* and/or *T. brennaborense*.

On the other hand, the present invention identifies *Treponema pedis* as one of the etiologic agents of digital dermatitis (DD) in mammals, in particular ungulate digital dermatitis. The invention therefore further provides isolated cultures of *Treponema pedis* for effectively immunizing susceptible mammals, preferably ungulates, against DD, in particular against bovine digital dermatitis, and methods of diagnosing DD by detecting infection with a series of specific *Treponema* antigens.

The invention thus provides for a, preferably biologically pure, culture of *Treponema* spp. bacterins, preferably *Treponema pedis* bacterins or *T. phagedenis, T. vincentii, T. medium, T. refringens, T. calligyrum, T. maltophilum* and/or *T. brennaborense*, optionally supplemented or in combination with one or more isolated antigens from *Treponema* spp. or with other digital dermatitis causative pathological agents such as *D. nodosus* or *F. necrophorum*, for use as a vaccine.

Such antigens are already listed above.

All of the above identified aspects and embodiments of the invention, are based on the surprising findings that *Treponema* spp. bacterins effectively immunized mammals against digital dermatitis, in particular against bovine digital dermatitis. In this sense, in Example 1, the in vitro immunogenicity of experimental vaccines against an experimental infection of BDD was assessed. The in vivo efficacy against an experimental infection of BDD in calves for these vaccines was also tested. The materials and methods associated to these vaccines, their preparation as well as the qualitative and quantitative composition, the vaccination protocol and animals used are described in the examples section.

As illustrated in the results provided in example 1, vaccines B (4 recombinant proteins alone without *Treponema* bacterins) and D (placebo) were clearly not effective. In contrast, with vaccines A (*Treponema pedis* bacterin+4 recombinant proteins) and C (*Treponema pedis* bacterin alone), the authors of the present invention did not only obtain a strong response against *T. pedis* but also against *T. phagedenis*. Since none of the formulations tested contained *T. phagedenis*, this can only be explained in virtue of a potential cross-reactivity. In addition, there was no difference between using adjuvant A or B. Moreover, there was an increase in the immunological response of the combined vaccine (bacterin+recombinants) in respect of the vaccine comprising the bacterium alone (A vs C), demonstrated with the serum titter at day 47 post-vaccination.

In addition, as shown in example 2, the authors assessed the in vivo efficacy of 2 experimental vaccines against an experimental infection of BDD in calves and confirm the results commented above. From this last experiment it is very interesting to note that when compared any of vaccines A or B with vaccine number C from the previous set of experiments shown in example 1, it is apparent that most of the potential therapeutic effect is attributable to the *Treponema* bacterin, whereas the recombinant antigens used in vaccine A of the previous experiment seem to enhance the immunological reaction of a vaccine comprising inactivated *T. pedis* bacterin.

Figure 10:
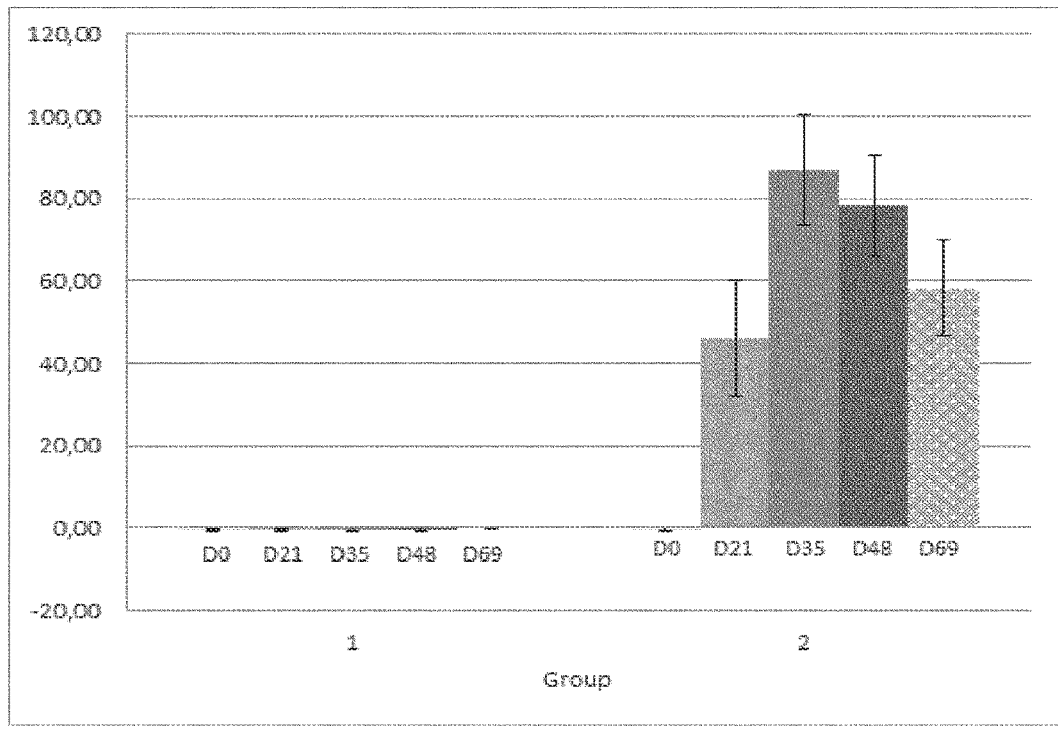
FIG. 10: Serology/ELISA against *T. pedis* (A), *T. phagedenis* (B), and *T. medium* (C) of sera obtained from vaccinated cattle with a *T. phagedenis* bacterin at days 0, 21, 35, 48, and 69. Mean of IRPC (Relative Index Percentage) is shown as the ordinates for the different groups, as the abscissas. Each Group is illustrated in example 4.
Figure 10:
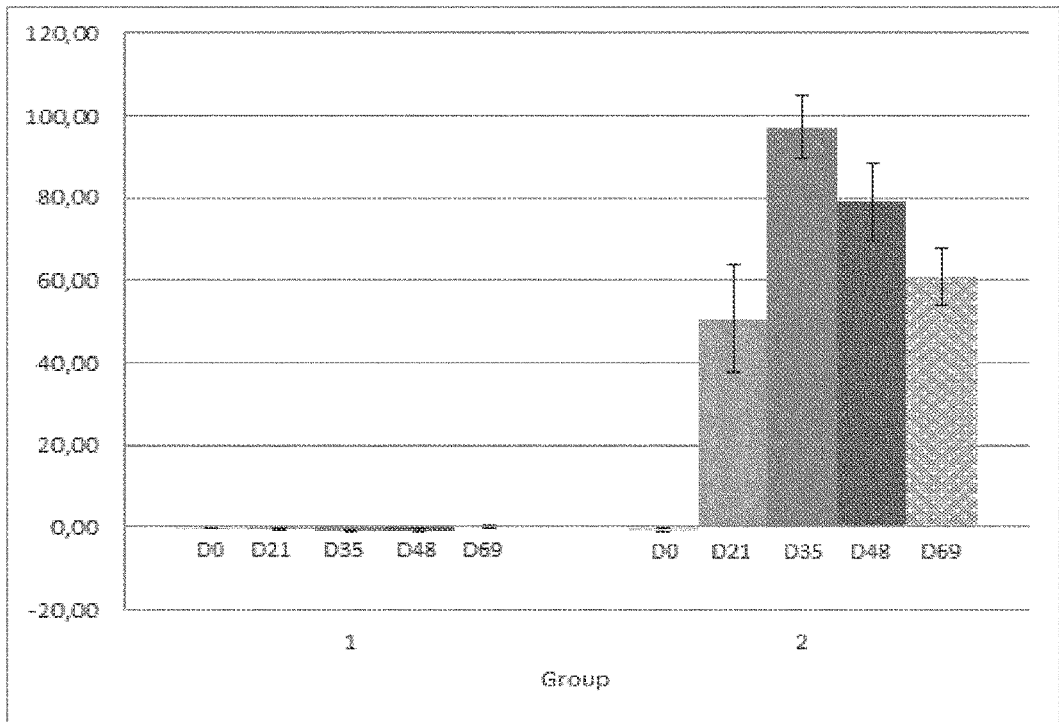
Figure 10:
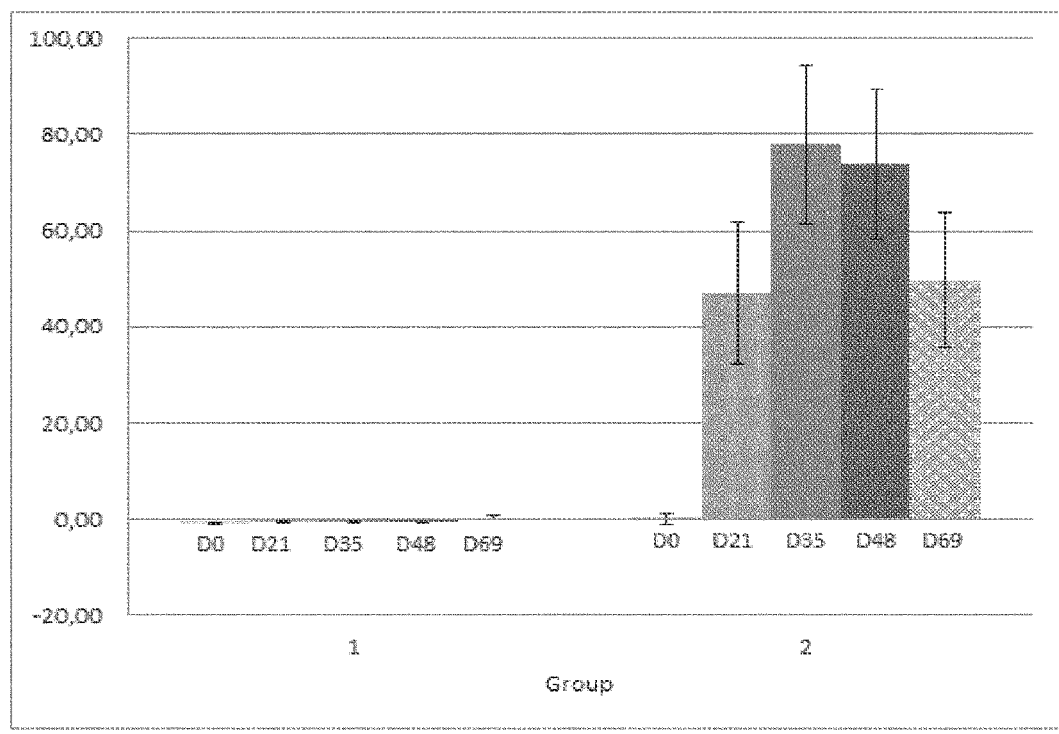

Furthermore, the application additionally discloses, in particular in example 4, the immunogenicity of an experimental *T. phagedenis* vaccine against BDD, wherein an immunological response against the different *Treponema* spp. tested (*T. pedis, T. phagedenis* and *T. medium*) was clearly observed from animal's sera of Group 2. Since the vaccine formulation of Group 2 did not contain *T. pedis* or *T. medium* bacterins, the immunological response observed in vaccinated animals can be attributed to the cross-reactivity between *Treponema* spp. (FIG. 10). Furthermore, a clear inhibitory effect on the in vitro growth of *T. phagedenis* with the sera of calves vaccinated with the *T. phagedenis* bacterin (Group 2) was observed. This inhibitory effect was not observed for the control group.

These results suggest that the immunological response observed in vaccinated animals can be attributed to the cross reactivity between *Treponema* species which share some epitopes which are responsible for that cross reaction.

Moreover, the application further discloses, in particular in example 5, the immunogenicity of an experimental *T. phagedenis* vaccine complemented with antigens against BDD, wherein an immunological response against all the antigens present in the vaccine composition in animal's sera of vaccinated Group 2 was clearly observed. Furthermore, the immunological response against the MSP protein of *T. phagedenis* was increased when the bacterin was complemented with the recombinant proteins (Group 2). Even though, Group 3 (bacterin alone) developed a clear immunological response as well. Contrary, the control group (Group 1) did not develop an immunologically response to any of the tested antigens.

Moreover, a clear inhibitory effect on the in vitro growth of *T. phagedenis* was observed in the sera of vaccinated calves of Group 2 (bacterin+recombinant proteins) and Group 3 (bacterin alone). These results demonstrate the presence of neutralizing antibodies in animals vaccinated in Group 2 and 3.

Consequently, these findings indicate that *Treponema* species share some epitopes, probably outer membranes or flagellar epitopes, which are responsible for the cross reactivity and are conserved between different species of *Treponema* spp. These epitopes are clearly involved in protection in view of the results obtained thus far in an experimental infection in calves by using two different experimental *Treponema* spp. vaccines.

Thus, the results provided herein thus make it feasible to extrapolate the same to any *Treponema* spp. vaccine compositions, in particular the invention provides, in one aspect, a pharmaceutical composition comprising an immunogenically effective amount of *T. pedis, T. phagedenis, T. vincentii, T. medium, T. refringens, T. calligyrum, T. maltophilum* and/or *T. brennaborense*. More particularly, in view of these results, the present invention identifies *Treponema pedis* and *Treponema phagedenis* as two of the etiologic agents of digital dermatitis (DD) in mammals, in particular ungulate digital dermatitis. The invention therefore provides isolated cultures of *Treponema pedis* and *Treponema phagedenis* vaccines for effectively immunizing susceptible mammals, preferably ungulates, against DD, in particular against bovine digital dermatitis, and methods of diagnosing DD by detecting infection with a series of specific *Treponema* antigens. Therefore, in one aspect, the invention provides a pharmaceutical composition comprising an immunogenically effective amount of *Treponema pedis* and/or *Treponema phagedenis* bacterins, preferably of any *T. pedis* strains such as but not limited to T3552B, G819CB, T18B, or T354A, or the *T. pedis* strain deposited by HIPRA SCIENTIFIC S.L.U. (Avda. La Selva, 135-Amer, Girona, Spain) in the Leibnitz-Institut DSMZ-Deutsche Sammlung von Mikroorganismen und Zellkulturen GmbH (InhoffenstraRe 7 B38124 Braunschweig, Germany) under accession number DSM 32663 on Oct. 10, 2017; or preferably any *T. phagedenis* strains such as but not limited to V1, V2, T413, T551B, T603, B-7330, or the *T. phagedenis* strain deposited under the Budapest treaty by HIPRA SCIENTIFIC, S.L.U. (Avda. La Selva, 135-Amer, Girona, Spain) in the Leibnitz-Institut DSMZ-Deutsche Sammlung von Mikroorganismen and Zellkulturen under accession number DSM 32950 on Nov. 7, 2018. Preferably, said pharmaceutical compositions further comprise isolated antigens, preferably recombinant antigens, from *Treponema* spp. or other digital dermatitis causative pathological agents such as *D. nodosus* or *F. necrophorum*. More preferably, said pharmaceutical composition further comprises isolated antigens from *Treponema* spp. selected from the list consisting of MSP (Major Outer Sheath Protein), PrtP (Serine-protease Complex PrtP-like Protein), TlyC (Hemolysin C), OrfC (Surface Antigen OrfC Lipoprotein), and Hemolysin III. Even more preferably, said pharmaceutical composition further comprises isolated antigens from *Treponema pedis* selected from the list consisting of MSP (Major Outer Sheath Protein), PrtP (Serine-protease Complex PrtP-like Protein), preferably PrtPM (PrtP Mature Protein), TlyC (Hemolysin C), and OrfC (Surface Antigen OrfC Lipoprotein); and/or antigens MSP and Haemolysin III from *Treponema phagedenis*; and/or antigens PrtP, preferably PrtPM, from *Treponema vincentii*; and/or antigens Apr2 (Acidic Extracellular Subtilisin-like Protease Apr2), preferably Apr2BM (Apr2 Benign Mature Protein), Apr5 (Acidic Extracellular Subtilisin-like Protease Apr5), preferably Apr5M (Apr5 Mature Protein), and Bpr (Basic Extracellular Subtilisin-like Protein Bpr), preferably BprM (Bpr Mature Protein), from *Dichelobacter nodosus*; as well as other candidate proteins, polypeptides or antigens useful in the present invention selected from adhesins, peptidases, proteases, surface antigens, proteins involved in motility, and haemolysins. Other polypeptides or antigens useful in the present invention are preferably selected from the following list:

PcrB (Serine-protease Complex PrcB-like protein);
PcrA (Serine-protease Complex PrcA-like protein);
Cys peptidase;
Hemolysin erythrocyte lysis protein 2;
Surface antigen BspA;
Filament protein;
Flagellar hook protein;
Prolyl endopeptidase;
Oligopeptidase;
Oligopeptidase B; and
Oligopeptidase F;

or any combination thereof.

In addition, since the recombinant antigens used in the present invention enhanced the immunological response of the exemplified vaccines compositions, the results provided herein thus make it feasible to extrapolate the same to any *Treponema* spp. vaccine compositions. Therefore, in a further aspect the present invention provides a pharmaceutical composition comprising an immunogenically effective amount of *Treponema* spp. bacterins, wherein said *Treponema* spp. bacterins are preferably selected from *T. pedis, T. phagedenis, T. vincentii, T. medium, T. refringens, T. calligyrum, T. maltophylum* and/or *T. brennaborense*, preferably from *T. pedis* or *T. phagedenis*, and one or more isolated antigens from *Treponema* spp. or other digital dermatitis causative pathological agents such as *D. nodosus* or *F. necrophorum*. Such pharmaceutical compositions are useful for effectively immunizing susceptible mammals, preferably ungulates, against DD, in particular against bovine digital dermatitis; wherein such isolated antigens, preferably recombinant antigens, are preferably obtained from *Treponema* spp. or other digital dermatitis causative pathological agents such as *D. nodosus* or *F. necrophorum*. More preferably, said antigens are the *Treponema* antigens selected from the list consisting of: MSP (Major Outer Sheath Protein), PrtP (Serine-protease Complex PrtP-like Protein), TlyC (Hemolysin C), OrfC (Surface Antigen OrfC Lipoprotein), and Hemolysin III. It is noted that all of these antigens can be obtained from *Treponema* spp. such as but not limited to *T. pedis, T. phagedenis,* or *T. vincentii*. Additional antigens useful in the present invention can be selected from other digital dermatitis causative pathological agents such as *D. nodosus* or *F. necrophorum*. All of these antigens can be used in combination in the pharmaceutical composition of the invention and are preferably recombinantly produced. More preferably, said proteins, polypeptides or antigens useful in the present invention are selected from virulence factors such as adhesins, peptidases, proteases, surface antigens, proteins involved in motility and haemolysins. Even more preferably said proteins, polypeptides or antigens useful in the present invention are selected from the following list:

MSP (Major Outer Sheath Protein);
PrtP (Serine-protease Complex PrtP-like Protein) and PrtPM (PrtP Mature Protein);
TylC (Hemolysin C);
OrfC (Surface Antigen OrfC Lipoprotein);
Haemolysin III;
Apr2 (Acidic Extracellular Subtilisin-like Protease Apr2) and Apr2BM (Apr2 Benign Mature Protein);
Apr5 (Acidic Extracellular Subtilisin-like Protease Apr5) and Apr5M (Apr5 Mature Protein);
Bpr (Basic Extracellular Subtilisin-like Protease Bpr) and BprM (Bpr Mature Protein);
PrcB (Serine-protease Complex PrcB-like protein);
PrcA (Serine-protease Complex PrcA-like protein);
Cys peptidase;
Hemolysin erythrocyte lysis protein 2;
Surface antigen BspA;
Filament protein;
Flagellar hook protein;
Prolyl endopeptidase;
Oligopeptidase;
Oligopeptidase B; and
Oligopeptidase F.

Still more preferably, said antigens are antigens selected from the list consisting of MSP, PrtP, preferably PrtPM, TlyC, and OrfC from *Treponema* pedis; or antigens MSP and Haemolysin III from *Treponema phagedenis*; or antigens PrtP, preferably PrtPM, from *Treponema vincentii*; or antigens Apr2, preferably Apr2BM, Apr5, preferably Apr5M, and Bpr, preferably BprM, from *Dichelobacter nodosus*, or any combination thereof, wherein optionally said antigens are recombinantly produced.

The pharmaceutical composition of the invention may further comprise a pharmaceutically acceptable carrier. The carrier suitable for preparing the vaccine in liquid form may include water, or an isotonic saline solution, that is to say, with a salt concentration equal to that of the physiological cellular medium, or an oil, or the culture liquid wherein the bacteria are cultured, or the mixtures thereof.

Additionally, if it is desired, the carrier can include other auxiliary substances or pharmaceutically acceptable excipients such as for example wetting agents, dispersant agents, emulsifying agents, buffer agents (for example phosphate buffer), stabilizing agents such as carbohydrates (for example glucose, sucrose, mannitol, sorbitol, starch or dextrans), or proteins (for example albumin, casein, bovine serum or skimmed milk).

The physical-chemical characteristics of the excipients as well as the name of the commercial products under which they are marketed can be found in the book R. C. Rowe et al., Handbook of Pharmaceutical Excipients, 4$^{th}$ edition, Pharmaceutical Press, London, 2003 [ISBN: 0-85369-472-9].

The pharmaceutical compositions described above, preferably vaccine compositions, can be used in a variety of pharmaceutical preparations for the treatment and/or prevention of digital dermatitis (DD) in mammals, in particular ungulate digital dermatitis. The pharmaceutical compositions of the present invention are typically used to vaccinate hooved animals such as cattle, sheep, goats and other animals infected by *Treponema* spp. including humans.

The immunogenic cell organism, which is employed as the active component of the present vaccines, comprises attenuated or inactivated DD-associated *Treponema* spp., preferably inactivated *Treponema* spp. bacterin, and more preferably an inactivated *Treponema pedis* or *phagedenis* bacterin. Inactivation can be achieved i.e by chemical, molecular or heat treatment. These spirochetes can be isolated from subjects affected with DD. The spirochetes can be maintained in infected subjects, or in suitable nutrient media. The immunogenic spirochetes are typically isolated from skin of affected animals and cultured in defined media. The spirochetes culture may be inactivated either by chemical, molecular or heat treatment. Spirochetes also can be inactivated by exposing the culture under aerobic (oxygen) conditions. The inactivation processes render the culture without toxicity while other properties, typically immunogenicity, is maintained.

To prepare the vaccine, the spirochetes are first separated from the medium by centrifugation or filtration, or with the use of selective media and the like. The spirochetes can be treated by a number of methods, including chemical treatment, to inactivate them as explained above. The spirochetes suspensions can be dried by lyophilization or frozen in an aqueous suspension thereof to yield inactivated whole cells.

The dried or cultured whole cells are then adjusted to an appropriate concentration, optionally combined with a suitable adjuvant, and packaged for use. Suitable adjuvants include but are not limited to: aluminum hydroxide, aluminum phosphate, aluminum oxide, muramyl dipeptides, vitamin E, squalene, squalene, saponins for example Quil A, QS-21, ginseng, zymosan, glucans, non-ionic block polymers, monophosphoryl lipid A, vegetable oils, complete Freund's adjuvant, incomplete Freund's adjuvant, W/O, O/W, W/O/W type emulsions, Ribi adjuvant system (Ribi Inc.), heat-labile enterotoxin from *E. coli* (recombinant or otherwise), cholera toxin, dimethylaminoehtyldextran, dextrans or analogs or mixtures thereof.

Finally, the immunogenic product can be incorporated into liposomes for use in a vaccine formulation, or may be conjugated to polysaccharides or other polymers.

The vaccines of the invention are typically prepared as parenteral vaccines in the form of solutions, emulsions or liquid suspensions. They can also be prepared in a solid form suitable to be dissolved or suspended in a liquid vehicle before injection.

Particularly, the vaccine is
(a) in liquid form; or
(b) in dry powder form, lyophilized, freeze dried, spray dried, or foam dried.

The typical volume of a dose of the vaccine of the invention is between 0.1 ml and 5 ml, particularly between 0.15 ml and 3 ml, and more particularly between 0.2 ml and 2 ml.

Usually, for intramuscular administration it is used between 0.5 ml and 5 ml, particularly between 1 ml and 3 ml, and more particularly between 1 ml and 2 ml.

The liquid vehicles which can be used for preparing the vaccine of the invention include, for example, water (in particular, water for injection), saline solution with a physiological salt concentration, or the culture liquid in which the bacteria are cultured.

The vaccine of the invention can be administered by different routes of administration. Particular routes include but are not limited to oral, transdermal, transmucosal, intradermal, subcutaneous, intramuscular, intraperitoneal or intravenous route. Particularly they are administered by intramuscular route. According to the desired duration and effectiveness of the treatment, the compositions according to the invention may be administered once or several times, also intermittently, for example on a daily basis for several days, weeks or months and in different dosages. Particularly, the immunogenic compositions of the invention are administered several times. More particularly the vaccination plan comprises two doses, the second dose administered 3 weeks after the first one. Said vaccine can be prepared according to the normal process used by the person skilled in the art for the preparation of pharmaceutical formulations suitable for the different forms of administration as is described for example in the manual Remington The Science and Practice of Pharmacy, 20$^{th}$ edition, Lippincott Williams & Wilkins, Philadelphia, 2000 [ISBN: 0-683-306472]. More particularly, the vaccine is for use by intramuscular route.

For parenteral administration, the antigen may be combined with a suitable carrier. For example, it may be administered in water, saline or buffered vehicles with or without various adjuvants or immunomodulating agents such as aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid, *Bordetella pertussis*, and the like. Such adjuvants are available commercially from various sources, for example, Merck Adjuvant 6 (Merck and Company, Inc., Rahway, N.J.). Other suitable adjuvants are MPL+TDM Emulsion (RIBBI Immunochem Research Inc. U.S.A.). Other immuno-stimulants include interleukin 1, interleukin 2 and interferon-gamma. These proteins can be provided with the vaccine or their corresponding genetic sequence provided as a functional operon with a recombinant vaccine system such as vaccinia virus. The proportion of antigen and adjuvant can be varied over a broad range so long as both are present in effective amounts.

As already stated, in addition to the *Treponema* ssp bacterins, preferably *Treponema pedis* or *phagedenis* bacterins, the vaccine can also include an antigen from *Treponema* spp. or other digital dermatitis causative pathological agents such as *D. nodosus* or *F. necrophorum*, as discussed above. Moreover, antigens to other ungulate diseases can also be included in the vaccines. For example, the vaccine can include antigens to ungulate *Fusobacterium necrophorum, Porphyromonas levii,* and *Dichelobacter nodosus* (the organisms that cause interdigital necrobacillosis, commonly known as footrot), leptospiral bacteria, bovine respiratory syncytial virus, bovine herpes virus, bovine diarhhea virus, bovine parainfluenza virus, vesicular stomatitis virus, malignant catarrhal fever virus, blue tongue virus, pseudorabies virus, rabies virus, rinderpest virus,

*Guggenheimella, Porphyromonas, Bacteroides, Prevotella, Peptosteptococcus, Campylobacter, Mycoplasma, Corynebacterium/Actinomyces, Cryptosporidium*, Rotavirus, Coronavirus and *Clostridia* spp. antigen.

Furthermore, in case the vaccine comprises at least *Treponema pedis* or *phagedenis*, said vaccine might further comprise an immunogenically effective amount of a bacterin selected from the group consisting of: *Treponema medium, Treponema vincentii, Treponema phagedenis, Treponema pedis, Treponema refringens, Treponema calligyrum, Treponema maltophilum* and *Treponema brennaborense*. Preferably, *Treopnema medium, Treponema vincentii, Treponema pedis* and *Treponema phagedenis*. As shown in the examples, these bacterins improved the therapeutic effect of the vaccines of the present invention comprising *Treponema pedis*.

In addition, it is further noted that the vaccine compositions of the invention are administered to a cattle, sheep, horses, or goats susceptible to or otherwise at risk of infection to induce an immune response against the antigen and thus enhance the patient's own immune response capabilities. Such an amount, as already stated throughout the present specification, is defined to be an "immunogenically effective amount." In this use, the precise amounts depend on the judgement of the vaccine manufacturer and prescribing veterinarian and would include consideration of the patient's state of health and weight, the mode of administration, the nature of the formulation, and the like.

A variety of vaccination regimens may be effective in immunizing cattle and other animals. For example, ungulate young and adults can both be vaccinated, preferably calves. A second immunization will be given 2-4 weeks after initial immunization. Animals that have been previously exposed to *Treponema* may require booster injections. The booster injection is preferably timed to coincide with times of maximal challenge and/or risk of abortion. Different immunization regimes may be adopted depending on the judgement of the veterinarian. Generally, on a per-dose basis, the concentration of the *Treponema* spp. bacterins, typically the whole cell, can range from about 10 to about $10^9$ cells per dose, or 1 µg to about 100 mg antigen per dose. For administration to cattle, a preferable range is from about $10^3$ to $10^9$ cells or 1 µg to 1 mg antigen per unit dose, preferably from 10 µg to 1 mg, more preferably from 30 µg to 1 mg, and even more preferably from 50 µg to 1 mg antigen per unit dose. A suitable dose volume range is 0.5 to 2.0 ml, preferably about 2 ml. Accordingly, a typical dose for intramuscular injection, for example, would comprise 2 ml containing $10^9$ cells or 50 µg of antigen.

Vaccines of the invention may comprise a crude extract of *Treponema* spp., preferably *Treponema pedis* or *phagedenis* or any other *Treponema* spp. as exemplified throughout the present specification. Chemically fixed cells can also be used. As noted above, preferred vaccines comprise partially or completely purified *Treponema* protein preparations. The antigen produced by recombinant DNA technology is preferred because it is more economical than the other sources and is more readily purified in large quantities (Standard recombinant techniques can be carried out as described in well-known manuals to the skilled person in the art such as, for example, J. Sambrook and D. W. Russell, Molecular Cloning: A laboratory manual, $4^{th}$ edition, Cold Spring Harbor Laboratory Press, New York, 2012). In addition to use in recombinant expression systems, the isolated *Treponema* gene sequences can also be used to transform viruses that transfect host cells in animals. Live attenuated viruses, such as vaccinia or adenovirus, are convenient alternatives for vaccines because they are inexpensive to produce and are easily transported and administered. Other protein expression systems such as bacteria (for example *E. coli*) or yeast cells such as *Pichia, Saccharomyces* are also useful to express recombinant antigens of the invention.

Suitable viruses for use in the present invention include, but are not limited to baculovirus, pox viruses, such as canarypox and cowpox viruses, and vaccinia viruses, alpha viruses, adenoviruses, herpesvirus, and other animal viruses. The recombinant viruses can be produced by methods well known in the art, for example, using homologous recombination or ligating two plasmids. A recombinant canarypox or cowpox virus can be made, for example, by inserting the DNA encoding the *Treponema* protein or fragments thereof into plasmids so that they are flanked by viral sequences on both sides. The DNA encoding *Treponema* polypeptides are then inserted into the virus genome through homologous recombination.

The vaccine of the invention is for use in a method of prevention and/or treatment of diseases in a mammal, preferably ungulates. More in particular for preventing and/or treating digital dermatitis or associated diseases caused by *Treponema* spirochete bacteria in a subject. Thus, it can be administered in a subject in need thereof in an immunologically effective amount in a method for preventing and/or treating digital dermatitis, in particular bovine digital dermatitis, contagious ovine digital dermatitis and/or footrot; and more particularly in bovine digital dermatitis. That is, the immunogenic composition or the vaccine as defined above are for the manufacture of a medicament for the treatment and/or prevention of digital dermatitis or associated diseases caused by *Treponema* spp.

Furthermore, as already stated above, the present invention provides isolated antigens, preferably recombinant antigens, from *Treponema* spp. or from any other digital dermatitis causative pathological agents such as *D. nodosus* or *F. necrophorum*, preferably from *Treponema pedis* or *Treponema phagedenis*, selected from at least one, preferably at least 2 or 3, of the antigens already identified above, in the preparation of immunogenic proteins and compositions for use in digital dermatitis vaccine compositions. It is noted that such isolated antigens will enhance the immunological effect of any vaccine which comprises an immunogenically effective amount of a *Treponema* spp. bacterin, preferably selected from the group consisting of: *T. pedis, T. phagedenis, T. vincentii, T. medium, T. refringens, T. calligyrum, T. maltophylum* and/or *T. brennaborense*, preferably from *T. pedis* or *T. phagedenis*. Such vaccines are for use in a method of treatment of diseases in a mammal, preferably ungulates. More in particular for preventing and/or treating digital dermatitis or associated diseases caused by *Treponema* spirochete bacteria in a subject. Thus, these can be administered in a subject in need thereof in an immunologically effective amount in a method for preventing and/or treating digital dermatitis, and in particular bovine digital dermatitis. That is, these immunogenic compositions or vaccines are also for the manufacture of a medicament for the treatment and/or prevention of digital dermatitis or associated diseases caused by *Treponema* spp.

Moreover, the invention also provides a vaccination kit characterized in that it comprises a container comprising the pharmaceutical composition or the vaccine of the invention.

In another aspect, the invention provides a vaccination kit characterized in that it comprises an informative manual or leaflet which contains the information on administering said pharmaceutical composition or vaccine of the invention.

In addition, the present invention also provides methods for detecting the presence or absence of *Treponema* spp., or of any other digital dermatitis causative pathological agents such as *D. nodosus* or *F. necrophorum*, in a biological sample. For instance, antibodies specifically reactive with any *Treponema* spp., or with any other digital dermatitis causative pathological agents such as *D. nodosus* or *F. necrophorum*, can be detected using either *Treponema* or any other antigens from digital dermatitis causative pathological agents such as *D. nodosus* or *F. necrophorum*. Such antigens or proteins have been described throughtout the present invention. Such proteins or antigens and isolates can be used to raise specific antibodies (either monoclonal or polyclonal) to detect the antigen in a sample. Each of these assays is described below.

For a review of immunological and immunoassay procedures in general, see Antibodies: A Laboratory Manual (Greenfield E. A., 2nd ed. 2014). The immunoassays of the present invention can be performed in any of several configurations, which are reviewed extensively in Enzyme Immunoassay (Maggio, ed., 1980); Tijssen, Laboratory Techniques in Biochemistry and Molecular Biology (1985)). For instance, the proteins and antibodies disclosed here are conveniently used in ELISA, immunoblot analysis and agglutination assays. In brief, immunoassays to measure anti-*Treponema* antibodies or antibodies against any other digital dermatitis causative pathological agents such as *D. nodosus* or *F. necrophorum*, or antigens can be either competitive or non-competitive binding assays. In competitive binding assays, the sample analyte (e.g., anti-*Treponema* antibodies) competes with a labelled analyte (e.g., anti-*Treponema* monoclonal antibody) for specific binding sites on a capture agent (e.g., isolated *Treponema* protein) bound to a solid surface. The concentration of labelled analyte bound to the capture agent is inversely proportional to the amount of free analyte present in the sample.

Non-competitive assays are typically sandwich assays, in which the sample analyte is bound between two analyte-specific binding reagents. One of the binding agents is used as a capture agent and is bound to a solid surface. The second binding agent is labelled and is used to measure or detect the resultant complex by visual or instrument means.

A number of combinations of capture agent and labelled binding agent can be used. For instance, an isolated *Treponema* antigen, preferably from *Treponema pedis* selected from the list consisting of MSP, PrtP, OrfC and TlyC or any combinations thereof, can be used as the capture agent and labelled anti-bovine antibodies specific for the constant region of bovine antibodies can be used as the labelled binding agent. Goat, sheep and other non-bovine antibodies specific for bovine immunoglobulin constant regions (e.g., .gamma. or mu.) are well known in the art. Alternatively, the anti-bovine antibodies can be the capture agent and the antigen can be labelled.

Various components of the assay, including the antigen, anti-*Treponema* antibody, or anti-bovine antibody, may be bound to a solid surface. Many methods for immobilizing biomolecules to a variety of solid surfaces are known in the art. For instance, the solid surface may be a membrane (e.g., nitrocellulose), a microtiter dish (e.g., PVC or polystyrene) or a bead. The desired component may be covalently bound or noncovalently attached through nonspecific bonding.

Alternatively, the immunoassay may be carried out in liquid phase and a variety of separation methods may be employed to separate the bound labelled component from the unbound labelled components. These methods are known to those of skill in the art and include immunoprecipitation, column chromatography, adsorption, addition of magnetizable particles coated with a binding agent and other similar procedures.

An immunoassay may also be carried out in liquid phase without a separation procedure. Various homogeneous immunoassay methods are now being applied to immunoassays for protein analytes. In these methods, the binding of the binding agent to the analyte causes a change in the signal emitted by the label, so that binding may be measured without separating the bound from the unbound labelled component.

Western blot (immunoblot) analysis can also be used to detect the presence of antibodies to *Treponema* in the sample. This technique is a reliable method for confirming the presence of antibodies against a particular protein in the sample. The technique generally comprises separating proteins by gel electrophoresis on the basis of molecular weight, transferring the separated proteins to a suitable solid support, (such as a nitrocellulose filter, a nylon filter, or derivatized nylon filter), and incubating the sample with the separated proteins. This causes specific target antibodies present in the sample to bind their respective proteins. Target antibodies are then detected using labelled anti-bovine antibodies.

The immunoassay formats described above employ labelled assay components. The label can be in a variety of forms. The label may be coupled directly or indirectly to the desired component of the assay according to methods well known in the art. A wide variety of labels may be used. The component may be labelled by any one of several methods. Traditionally a radioactive label incorporating $^3$H, $^{125}$I, $^{35}$S, $^{14}$C, or $^{32}$P was used. Non-radioactive labels include ligands which bind to labelled antibodies, fluorophores, chemiluminescent agents, enzymes, and antibodies which can serve as specific binding pair members for a labelled ligand. The choice of label depends on sensitivity required, ease of conjugation with the compound, stability requirements, and available instrumentation.

Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labelling or signal producing systems which may be used, see U.S. Pat. No. 4,391,904, which is incorporated herein by reference.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labelled, naturally occurring anti-ligands. Alternatively, any haptenic or antigenic compound can be used in combination with an antibody.

Some assay formats do not require the use of labelled components. For instance, agglutination assays can be used to detect the presence of the target antibodies. In this case, antigen-coated particles are agglutinated by samples comprising the target antibodies. In this format, none of the components need to be labelled and the presence of the target antibody is detected by simple visual inspection.

Finally, the present invention is further directed to a *T. pedis* strain deposited by HIPRA SCIENTIFIC S.L.U. (Avda. La Selva, 135-Amer, Girona, Spain) in the Leibnitz-Institut DSMZ-Deutsche Sammlung von Mikroorganismen und Zellkulturen GmbH (Inhoffenstraf3e 7 B38124 Braunschweig, Germany) under accession number DSM 32663 on Oct. 10, 2017; or to a *T. phagedenis* strain deposited under the Budapest treaty by HIPRA SCIENTIFIC, S.L.U. (Avda. La Selva, 135-Amer, Girona, Spain) in the Leibnitz-Institut DSMZ-Deutsche Sammlung von Mikroorganismen und Zellkulturen under accession number DSM 32950 on Nov. 7, 2018. Pharmaceutical compositions and vaccines of the invention also encompasses both deposited strains and their use in a method of treatment or prevention of digital dermatitis in a mammal, wherein the digital dermatitis is preferably bovine digital dermatitis, contagious ovine digital dermatitis and/or footrot.

The present invention is further shown in light of the following examples which merely illustrate the invention but do not limit the same. Furthermore, the present invention covers all possible combinations of particular and preferred embodiments described herein.

EXAMPLES

Example 1: In Vitro Immunogenicity and In Vivo Efficacy of Experimental Vaccines Against BDD in Calves 35 calves between 2 and 4 months of age, free of antibodies against *T. pedis* and *T. phagedenis* and without clinical signs of BDD were chosen for this study. The animals were randomly assigned into 7 groups of 5 calves each one (A to G). On Day 0 calves received a first dose of an experimental vaccine according to the group assignment. Three weeks later (Day 21) calves received a second dose of the vaccine. Vaccines were administered at the neck by subcutaneous route at 2 mL for each administration.

At Day 48 calves were challenged with a macerated culture obtained from naturally occurring BDD lesions. The challenge inoculum was obtained by homogenizing 23 samples of active BDD lesions from different cows. The macerated culture consisted of *T. phagedenis, T. medium/T. vincentii* and *T. pedis* (92% of BDD lesion samples positive to *T. phagedenis*, 85% positive to *T. medium/T. vincentii*-like and 13% positive to *T. pedis*). Furthemore 56% and 65% of BDD lesion samples were positive to *D. nodosus* and *T. praeacuta*, respectively.

Group A received Vaccine A which comprised $10^9$ bacteria/dose of inactivated *T. pedis* isolate (reference number B-8308, HIPRA SCIENTIFIC, S.L.U.) and 70 µg/dose of each purified recombinant proteins MSP (SEQ ID NO: 4), PrtPM (SEQ ID NO: 2) and OrfC (SEQ ID NO: 5) of *T. pedis* and Apr2BM (SEQ ID NO: 10) of *D. nodosus*. The vaccine was formulated at 50% w/w with the adjuvant Montanide A. An adjuvant based on a combination of a mineral oil and a product obtained from fatty acid and a sugar alcohol such as for example those marketed by the company SEPPIC under the commercial designation Montanide™. Emulsions of the W/O/W type can be prepared with said adjuvant.

Group B received Vaccine B which comprised 70 µg/dose of each purified recombinant proteins MSP (SEQ ID NO: 4), PrtPM (SEQ ID NO: 2) and OrfC (SEQ ID NO: 5) of *T. pedis* and Apr2BM (SEQ ID NO: 10) of *D. nodosus*. The vaccine was formulated at 50% w/w with the same adjuvant Montanide A.

Group C received Vaccine C which comprised $10^9$ bacteria/dose of the same inactivated *T. pedis* isolate of Group A. The vaccine was formulated at 50% w/w with the same adjuvant Montanide A.

Group D corresponded to the control group which received Vaccine D which comprised PBS without antigens and 50% v/v of the same Montanide A adjuvant.

Group E received Vaccine E which comprised $10^9$ bacteria/dose of the same inactivated *T. pedis* isolate as Group A and 70 µg/dose of each purified recombinant proteins MSP (SEQ ID NO: 4), PrtPM (SEQ ID NO: 2) and OrfC (SEQ ID NO: 5) of *T. pedis* and Apr2BM (SEQ ID NO: 10) of *D. nodosus*. The vaccine was formulated with 25% v/v of adjuvant B based on $AlOH_3/AlPO_4$ and 2% w/v of DEAE dextran.

Group F received Vaccine F which comprised 70 µg/dose of each purified recombinant proteins MSP (SEQ ID NO: 4), PrtPM (SEQ ID NO: 2) and OrfC (SEQ ID NO: 5) of *T. pedis* and Apr2BM (SEQ ID NO: 10) of *D. nodosus*. The vaccine was formulated with 25% v/v of adjuvant B based on $AlOH_3/AlPO_4$ and 2% w/v of DEAE dextran.

Group G received Vaccine G which comprised $10^9$ cells/dose of the same inactivated *T. pedis* isolate as Groups A, C and E. The vaccine was formulated with 25% v/v of adjuvant B based on $AlOH_3/AlPO_4$ and 2% w/v of DEAE dextran.

A summary of the different groups and vaccines is illustrated in the following table.

TABLE 1

Summary of the Groups and Vaccines used in the example 1.

| Groups | Vaccine | Antigens | Adjuvant |
|---|---|---|---|
| A (n = 5) | A | *T. pedis* inactivated bacterin + 4 recombinant proteins (MSP, PrtPM, OrfC, Apr2BM) | A |
| B (n = 5) | B | 4 recombinant proteins (MSP, PrtPM, OrfC, Apr2BM) | A |
| C (n = 5) | C | *T. pedis* inactivated bacterin | A |
| D (n = 5) | D | Placebo (PBS) | A |
| E (n = 5) | E | *T. pedis* inactivated bacterin + 4 recombinant proteins (MSP, PrtPM, OrfC, Apr2BM) | B |
| F (n = 5) | F | 4 recombinant proteins (MSP, PrtPM, OrfC, Apr2BM) | B |
| G (n = 5) | G | *T. pedis* inactivated bacterin | B |

Blood samples were collected from all calves on Days 0, 21, 35, 47, 59, 80, 97 to obtain sera.

In Vitro Results

The in vitro immunogenicity of the experimental vaccines was carried out by analyzing the neutralizing effect of sera from vaccinated animals at day 47 in the growth of *T. pedis*, and by indirect ELISA against *T. pedis* in order to detect the presence antibodies in the animals' sera (FIG. 1).

Inhibitory effect of the sera corresponded to the experimental vaccines containing *T. pedis* bacterin, with and without the recombinant proteins (Vaccines A, C, E and G). Similar results were obtained when using both adjuvants A and B.

Figure 2:
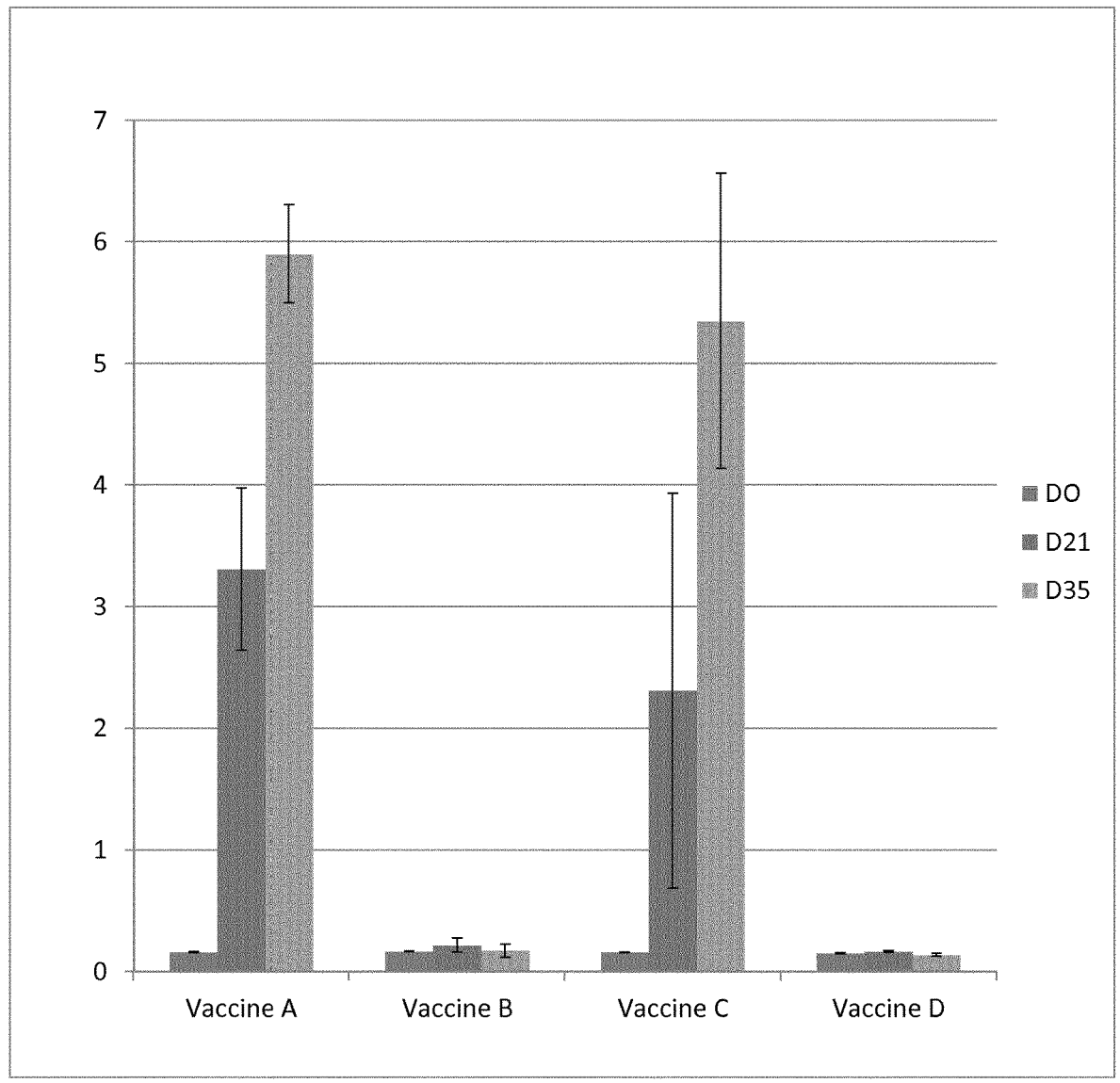
FIG. 2. ELISA against *T. pedis* isolate of sera obtained from cattle at days 0, 21 and 35 post-vaccination. Mean of the optical density (OD) at 405 nm is shown, as the ordinates, for different tested vaccines, as the abscissas. Each vaccine is illustrated in example 1.
Figure 3:
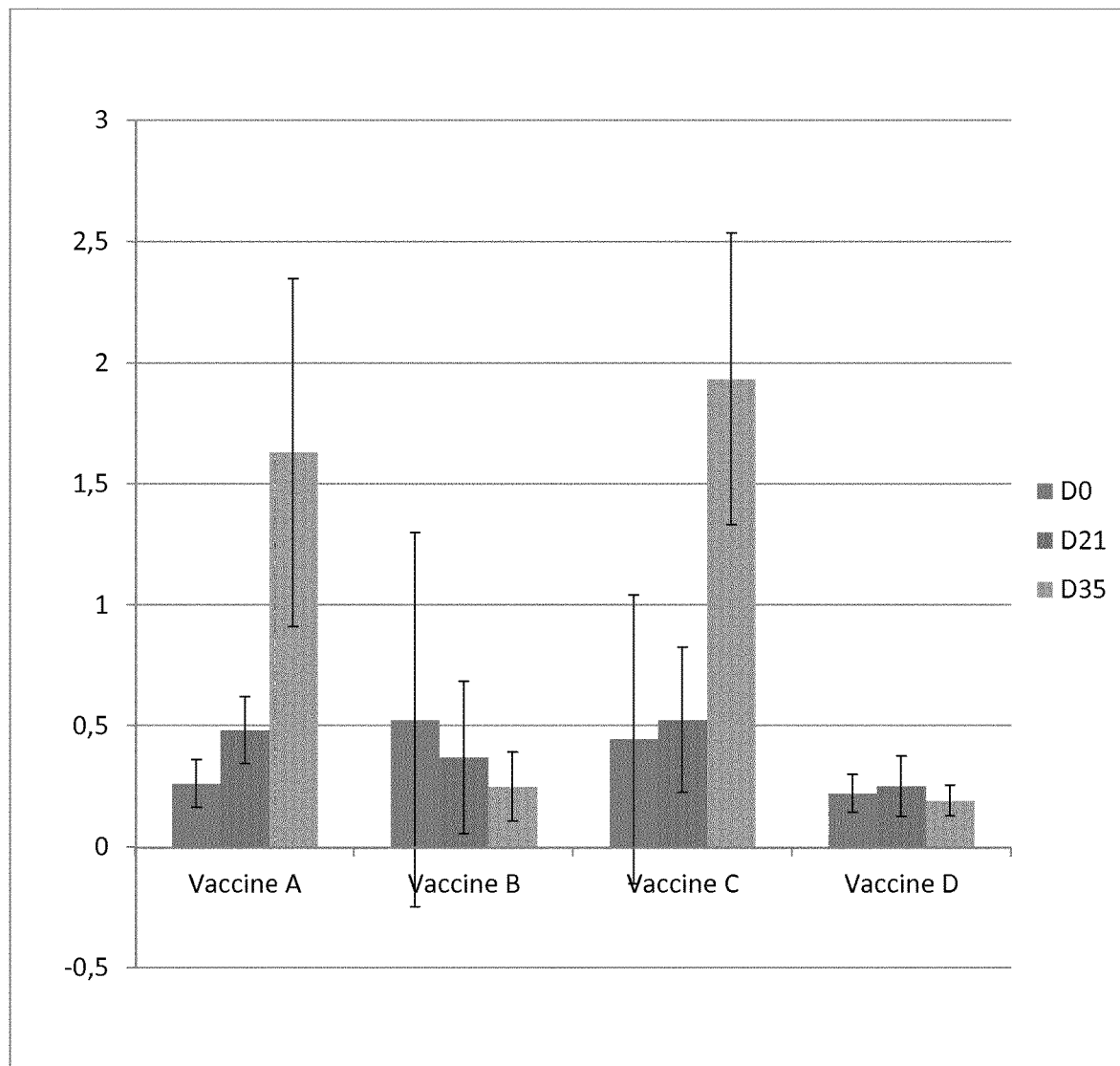
FIG. 3. ELISA against *T. phagedenis* isolate of sera obtained from cattle at days 0, 21 and 35 post-vaccination. Mean of the optical density (OD) at 405 nm is shown, as the ordinates, for different tested vaccines, as the abscissas. Each vaccine is illustrated in example 1.

Serology post-vaccination was analyzed by ELISA (IgG2) against whole bacterium *T. pedis* and *T. phagedenis* at different days post-vaccination (FIGS. 2 and 3), in order to assess the antibody humoral response.

No immunological response of the recombinant proteins when administered alone (vaccine B) and in the control group (vaccine D) was observed. A better immunological response was observed when the combined vaccine (bacterin+recombinant proteins; vaccine A) was administered to the animals. The immunological response to the combined vaccine was also better when compared to the bacterin-based vaccine administered alone (vaccine C).

There was a similar response with both adjuvants A and B.

A lower immunological response than *T. pedis* was observed for *T. phagedenis*. Since the vaccine formulations did not contain *T. phagedenis* antigens, a cross-reactivity was assumed.

In Vivo Efficacy Results Post-Infection

In order to assess the in vivo efficacy of the experimental vaccines a challenge was carried out at day 48 post-vaccination to groups A, C and D. As no in vitro efficacy was observed for the group B, which received the experimental vaccine containing only recombinant proteins alone, this group were left without challenge.

Figure 4:
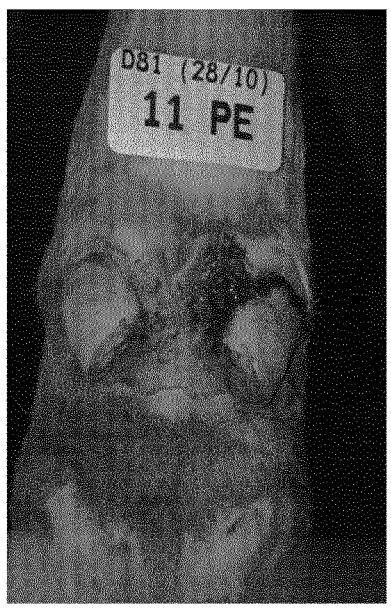
FIG. 4. Images showing different lesion severity and their corresponding score. A) Score DD=10 and D32 pi; B) Score DD=5 and D32 pi; C) Score DD=0 and D32 pi. Example 1.
Figure 4:
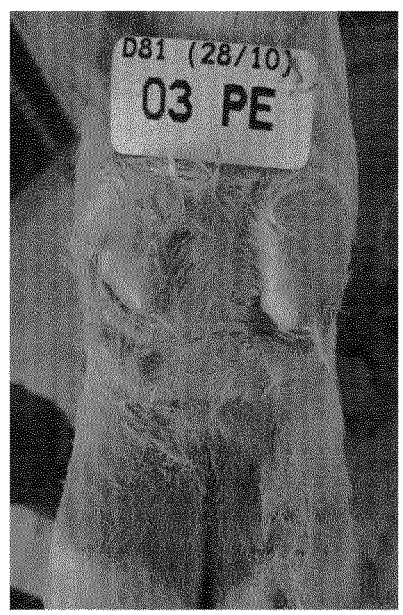
Figure 4:
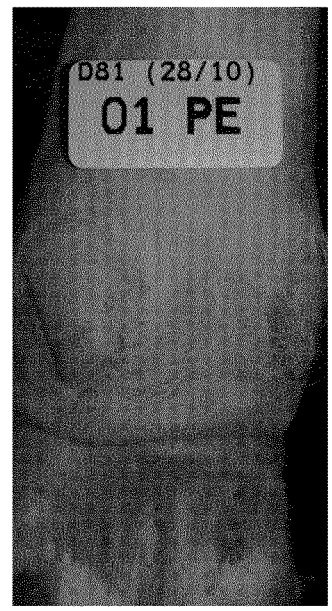

To assess the post-infection efficacy of the experimental vaccines, evaluation of the severity of the clinical macroscopic lesions was performed. The assessment was performed at day 32 post-infection. Different methods were used. The methods were based on assigning a score to each animal by evaluating pre-established parameters of the disease. Two different scores were used: Iowa score (Krull, A. C., Cooper, V. L., Coatney, J. W., Shearer, J. K., Gorden, P. J., & Plummer, P. J. A highly effective protocol for the rapid and consistent induction of digital dermatitis in Holstein calves. PloS one, 2016, 11.4: e0154481) and Wisconsin score (Gomez, A., Cook, N. B., Bernardoni, N. D., Rieman, J., Dusick, A. F., Hartshorn, R., Socha M. T., Read D. H., Döpfer D. An experimental infection model to induce digital dermatitis infection in cattle. *Journal of dairy science*, 2012, 95.4: 1821-1830). Table 2 shows how the Iowa score was obtained (see FIG. 4 as well).

TABLE 2

Assessment of the macroscopic lesions of BDD according to Iowa score.

| | Size of the lesion | | | |
|---|---|---|---|---|
| | Absence of lesion | Less than the initial abrasion area | No changes respect the abrasion area | Expands beyond initial abrasion area |
| Score | 0 | 1 | 3 | 5 |
| | Color of the lesion | | | |
| | Normal color, no lesion | Whitish | Pink | Red or bright red |
| Score | 0 | 1 | 2 | 3 |
| | Edges of the lesion | | | |
| | Absence of lesion | Edges well defined | No border defined | |
| Score | 0 | 1 | 2 | |

\* It was considered a digital dermatitis lesion when the final score was ≥7.

Figure 5:
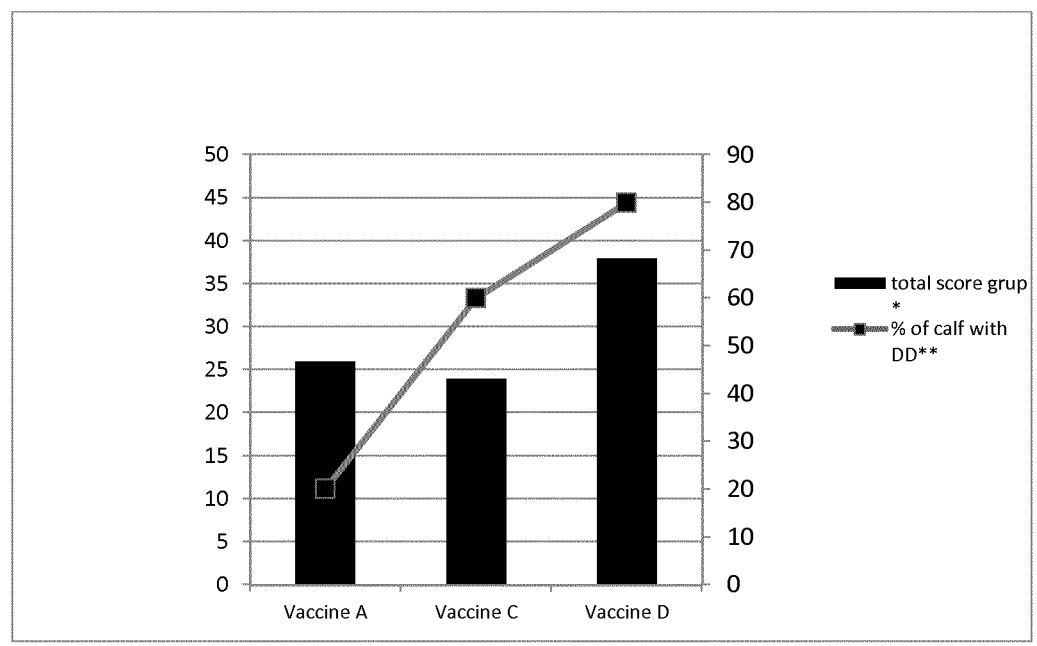
FIG. 5. Figures representing score lesions and percentages of animals with BDD lesion, according to Iowa and Wisconsin score at 32 days post-infection. A) Assessment of final macroscopic lesions at 32 days pi (Iowa score). Total Iowa score group (0 to 50) and percentage of calf with digital dermatitis are depicted in the left and right ordinates, respectively, for different assayed vaccines shown as the abscissas; B) Total lesion percentage at day 32 pi (Wisconsin score). Percentage of total lesion score is depicted, as the ordinates, for the different tested vaccines, as the abscissas. Each vaccine is illustrated in example 1.
Figure 5:
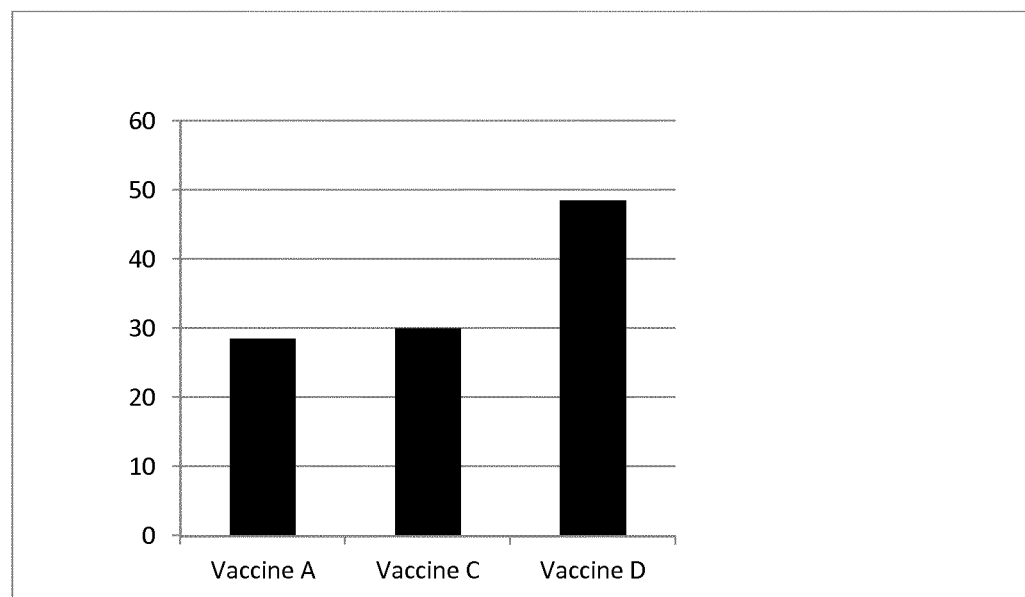

In groups A and C, 1/5 and 2/5 calves respectively did not develop clinical lesions, while 5/5 animals of the group D (control) developed lesions. Furthermore, when assessing the severity of the lesions, for both scores (Iowa and Wisconsin) groups A and C showed less lesion scores and percentage of calves with bovine digital dermatitis lesions with respect to the control group (D). There was also a major reduction in the percentage of animals presenting DD lesions (Iowa score ≥7) in the group vaccinated with the vaccine A (bacterin+recombinant proteins) (FIG. 5).

Conclusions of Example 1

A clear inhibitory effect on in vitro growth of *T. pedis* in the sera of calves vaccinated with *T. pedis* bacterin or the bacterin combined with recombinant proteins was observed. This effect was not seen in sera from animals which were vaccinated with the recombinant proteins alone.

A higher humoral response against *T. pedis* was observed when *T. pedis* bacterin vaccine was combined with recombinant proteins.

After the experimental infection with the inoculum containing *T. phagedenis*, *T. medium-vincentii*-like and *T. pedis*, it was observed that the vaccines with *T. pedis* alone or combined with the recombinant proteins reduced the incidence and the severity of the DD lesions compared to the control group. It was also observed that the group vaccinated with the combined vaccine (bacterin+recombinant proteins) showed less percentage of animals with DD lesions.

Example 2: Assessing the In Vivo Efficacy of Experimental Vaccines Against an Experimental Infection of BDD in Calves 30 calves between 2 and 3 months of age, free of antibodies against *T. pedis* and *T. phagedenis* and without clinical signs of BDD were chosen for this study. The animals were randomly assigned into 3 groups of 10 calves each one (groups A to C). On Day 0 calves received one dose of the vaccine according to their group assignment. Three weeks later (Day 21) calves received a second dose of the vaccine. Vaccines were administered at the neck by intramuscular route at 2 mL for each administration.

At Day 49 calves were challenged with a macerated culture obtained from naturally occurring BDD lesion as in Example 1. The macerated consisted of a homogenized of 13 samples of BDD active lesions from 10 different cows. In this case the 100% of samples were positive to *T. phagedenis* and *T. medium/T. vincentii*-like, and 69% were positive to *T. pedis*. Therefore, the macerated consisted of *T. phagedenis*, *T. medium/vincentii*-like and *T. pedis*. Furthermore 23% of BDD samples were also positive to *D. nodosus*.

Group A received vaccine 1, which comprised inactivated *T. pedis* (same isolate used in Example 1), inactivated *T. phagedenis* (isolate reference number B-7330, HIPRA SCIENTIFIC, S.L.U.), inactivated *T. medium* (isolate reference number B-8307, HIPRA SCIENTIFIC, S.L.U.) combined with the recombinant proteins MSP (SEQ ID NO: 4), PrtPM (SEQ ID NO: 2) and TlyC (SEQ ID NO: 3) of *T. pedis* and Apr2BM (SEQ ID NO: 10) from *D. nodosus*. Vaccine 1 contained adjuvant Montanide A as described in Example 1 at 50% w/w. The titer was $10^9$ total bacteria per dose of 2 ml and 50 µg of each recombinant protein per dose of 2 ml.

Group B received vaccine 2, which comprised inactivated *T. pedis* isolate, inactivated *T. phagedenis* isolate, and inactivated *T. medium* isolate (same isolates as Group A), this vaccine did not contain recombinant proteins. The vaccine contained the adjuvant Montanide A as described in Example 1 at 50% w/w. The titer was $10^9$ total bacteria per dose of 2 ml.

Group C corresponded to the control group which received vaccine 3 consisting of a PBS solution without antigens formulated with the adjuvant Montanide A as described in Example 1 at 50% w/w.

TABLE 3

Summary of the treatments groups of Example 2.

| Groups | Vaccine | Antigen | Adjuvant |
|---|---|---|---|
| A (n = 10) | 1 | *T. pedis*, *T. medium*, and *T. phagedenis* inactivated bacterins + 4 recombinants proteins (MSP, PrtPM, TlyC, Apr2BM) | A |
| B (n = 10) | 2 | *T. pedis*, *T. medium*, and *T. Phagedenis* inactivated bacterins | A |
| C (n = 10) | 3 | Placebo (PBS) | A |

At days 0, 21, 35, 46, 57, 64, 70, 81 and 95 blood was extracted from all the animals in order to obtain sera.

Figure 6:
FIG. 6. Growth and morphology inhibition assay of *T. pedis* in vitro from sera at day 35 post-vaccination, using dark field microscopy. A) Serum 1 (1/16) day 0 pv (vaccine 1); B) Serum 1 (1/16) day 35 pv (vaccine 1). Example 2.
Figure 6:
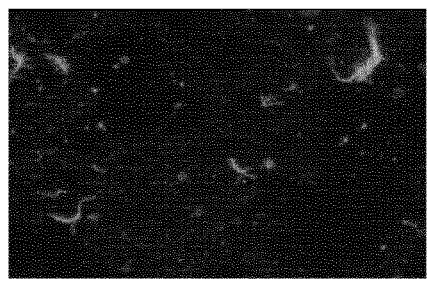

In Vitro Assay of *Treponema* spp. Growth Inhibition From the Sera Obtained Post-Vaccination The inhibition assay was performed using sera obtained on day 35 post-vaccination from vaccinated animals. The growth inhibition assay was carried out for *T. pedis* and *T. phagedenis*. This assay demonstrated that only calves belonging to the vaccinated groups A and B inhibited the growth of both bacteria. No effect on the growth inhibition was observed from sera belonging to the control group (FIG. 6).

Serology Results Post-Vaccination

To assess the humoral response upon vaccination different ELISA assays were performed. ELISA assays were performed with sera from days 0, 21, and 35 post-vaccination to detect antibodies against *T. pedis*, *T. phagedenis*, *T. medium*, *D. nodosus* and against the recombinant proteins MSP, PrtPM, TlyC from *T. pedis* and Apr2BM from *D. nodosus*. The sera obtained from the different animals was diluted 1/400 in order to perform the ELISA assay.

Figure 7:
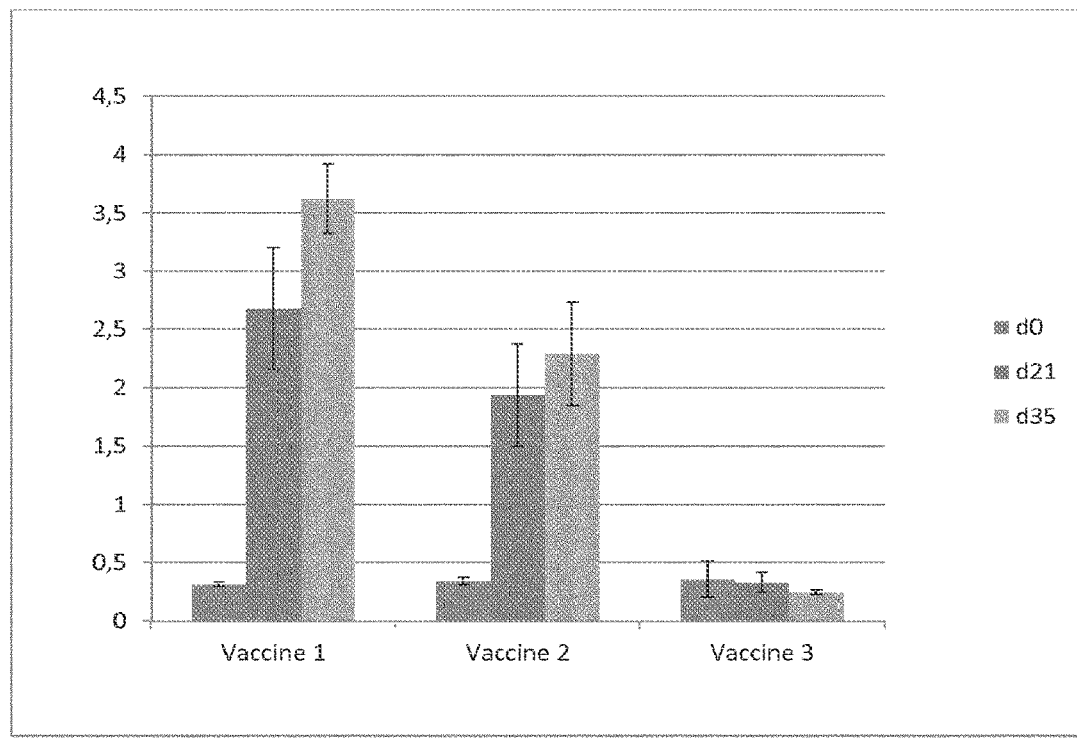
FIG. 7. Serology/ELISA (IgG2) against *T. pedis* (A), *T. phagedenis* (B) and *T. medium* (C) of sera obtained from cattle at days 0, 21 and 35 post-vaccination. Mean of the optical density (OD) at 405 nm is shown, as the ordinates, for different tested vaccines, as the abscissas. Each vaccine is illustrated in example 2.
Figure 7:
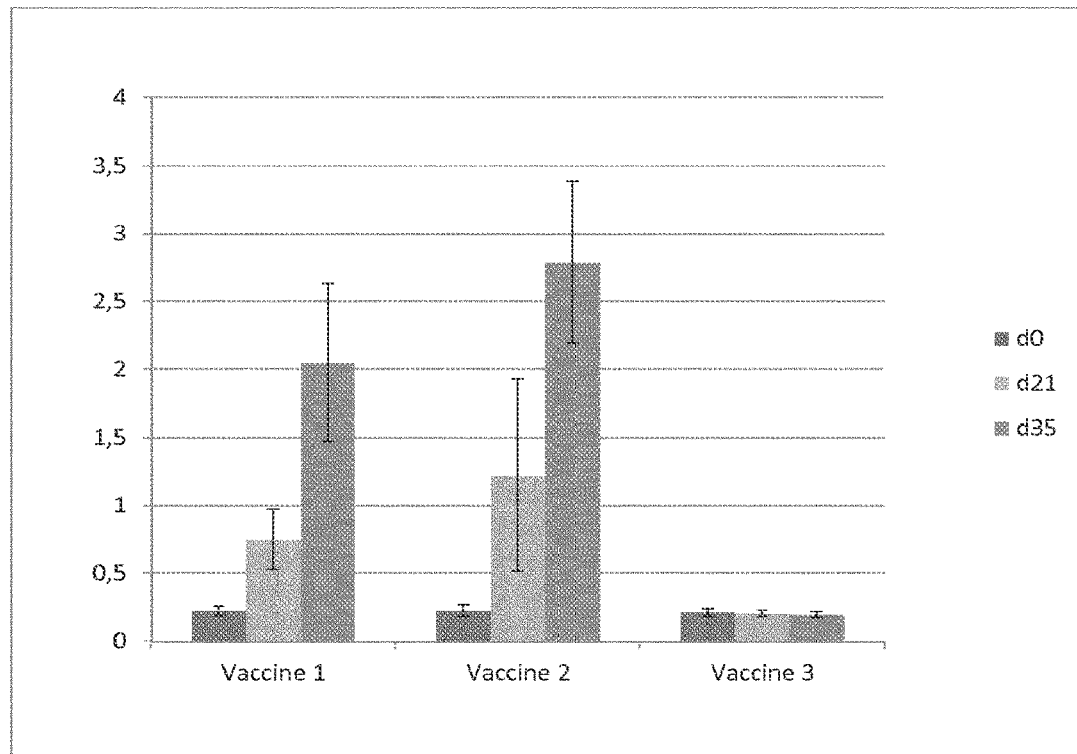
Figure 7:
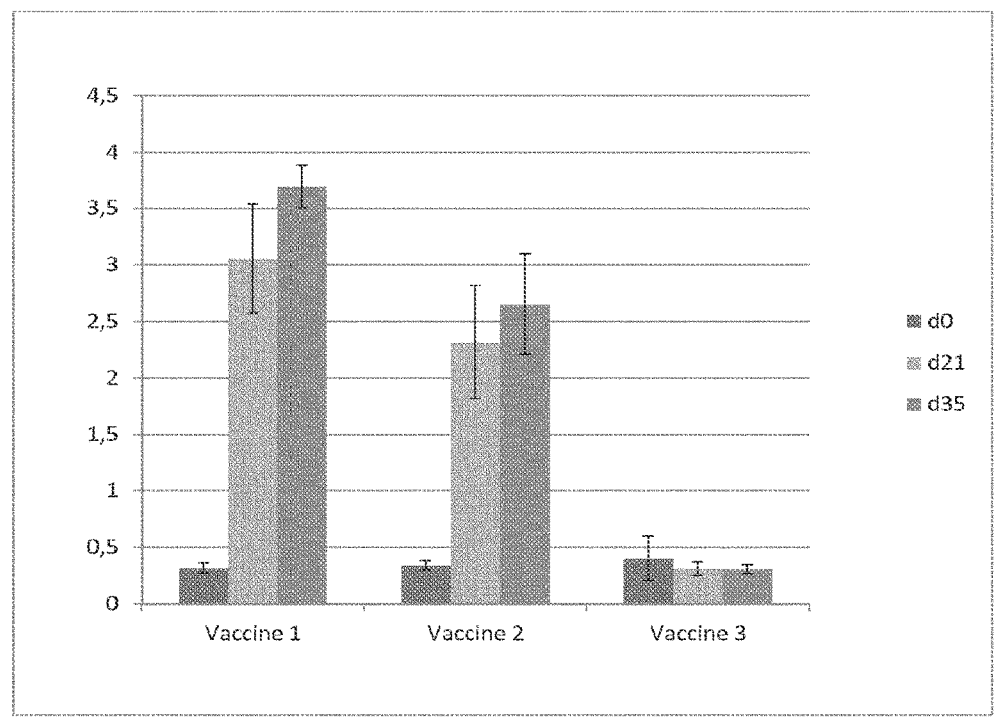

A good seroconversion of IgG2 antibodies against all antigens present in the study was observed (FIG. 7). Significant differences for seroconversion between the vaccinated groups and the control group were shown. Animals which were vaccinated with the *Treponema* spp. bacterins combined with recombinant proteins (vaccine 1) obtained higher humoral response against *T. pedis* and *T. medium* in comparison to vaccine 2 (bacterins-based vaccine).

In Vivo Efficacy Results Post-Infection

A final evaluation of the BDD lesions at day 32 post-infection (Day 81 of the study) was performed. The assessment was realized using the Iowa score as explained in the Example 1.

TABLE 4

Summary of the clinical assessment of the BDD macroscopic lesions at day 32 post-infection.

| Group, Vaccine | Proportion of calves with lameness | Proportion of calves with lesions of DD (score ≥7) | Proportion of calves with major spirochetes per MCP |
|---|---|---|---|
| A, 1 | 2/10 (20%) | 4/10 (40%) | 5/10 (50%) |
| B, 2 | 3/10 (30%) | 6/10 (60%) | 6/10 (60%) |
| C, 3 (placebo) | 5/9 (55%)** | 8/10 (80%) | 8/10 (80%) |

Regarding lesion severity scores, in groups A (vaccine 1) and B (vaccine 2) the severity was lower and even 1/10 and 3/10 of the groups A and B respectively did not reveal signs of lesion, while all the animals in the control group developed digital lesions.

Regarding the Iowa score, the percentage of calves that achieved a minimum of 7 score (Iowa score establishes a score of at least 7 to consider a BDD lesion) was 40%, 60% and 80% for the groups A (vaccine 1), B (vaccine 2) and C (vaccine 3) respectively. Significant differences were observed between group A and group C (vaccine 3, placebo) (p value=0.04 using the Mann-Whitney test).

Figure 8:
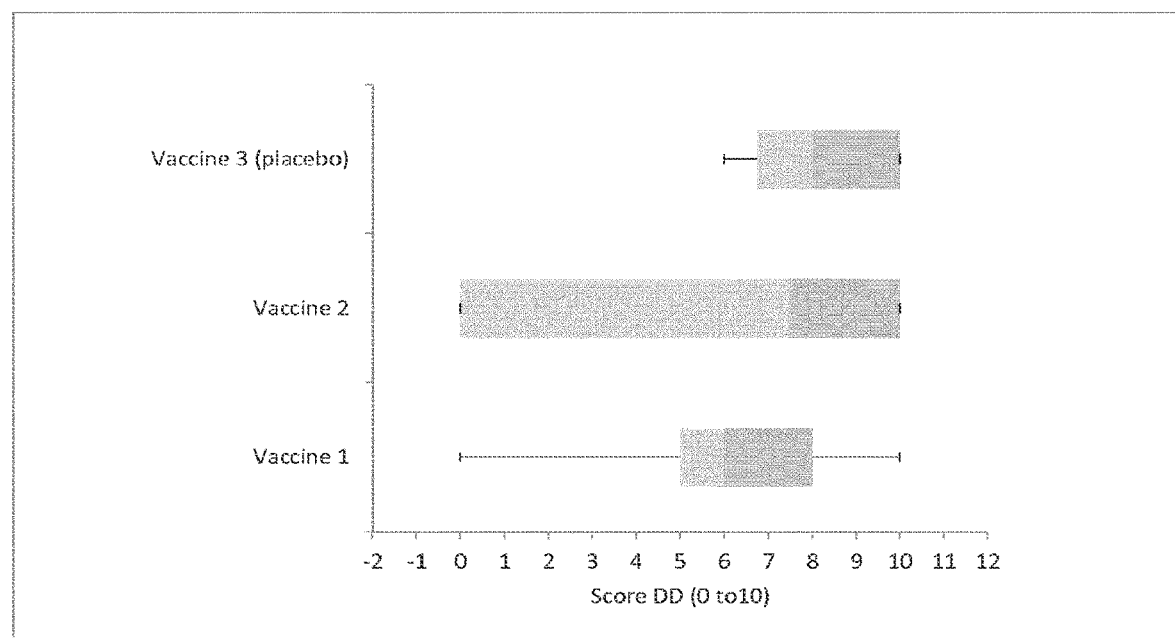
FIG. 8. Boxplot of the lesions score at day 32 post-infection for each group of calves. Digital dermatitis score lesion (0 to 10) is shown, as the abscissas, for different tested vaccines, as the ordinates. Example 2.

To sum up, it was observed that both vaccinated groups reduced the incidence and severity of the lesion respect to the control group. Furthermore, it was observed a higher protection in the group A (vaccine comprising a combination of bacterins plus recombinant proteins), as the differences respect the control group were significant (FIG. 8).

Summary

A clear in vitro growth inhibition effect of *T. pedis* and *T. phagedenis* was observed in the sera of vaccinated animals. Therefore, the antibodies raised against these *Treponema* spp. showed a clear inhibitory effect.

A high humoral response post-vaccination was observed against three genus of *Treponema* spp., i.e. *T. pedis*, *T. phagedenis* and *T. medium*. Significant differences with respect to the control group were also observed.

A higher humoral response against *T. pedis* was observed for the vaccine which combines *Treponema* spp. bacterins and recombinant proteins.

The assessment of the severity lesions at day 32 post-infection demonstrated that all the animals in the control group developed digital lesions, while several vaccinated animals did not develop any lesion. Furthermore, the vaccination reduced the severity of the lesions.

In the final assessment at day 32 post-infection, both the proportion of animals with BDD lesions (grade ≥7 according to the Iowa score) and the final lesion score showed statistical significance between the vaccinated group 1 (bacterins combined with recombinant proteins) and the control group.

Example 3: Demonstration of the Equivalence of the Immune Response Between Different *T. pedis* Strains In this study, 6 New Zealand rabbits of at least 3 weeks of age were immunized with 2 different formulations based on bacterins from two different *Treponema pedis* strains, 3 animals per each formulation. Group 1 was vaccinated with the same *T. pedis* strain as disclosed in the Examples 1 and 2, and Group 2 was vaccinated with *T. pedis* strain deposited by HIPRA SCIENTIFIC, S.L.U. (Avda. La Selva, 135-Amer, Girona, Spain) in the Leibnitz-Institut DSMZ-Deutsche Sammlung von Mikroorganismen und Zellkulturen under accession number DSM 32663 (Oct. 10, 2017)

The vaccine compositions were formulated with Freund adjuvant, and both contained $10^9$ bacteria/dose. Animals received two doses of 1 ml subcutaneously, the first one at day 0 of the study adjuvanted in FCA (Freunds Complete Adjuvant) and the second one 2 weeks later, at day 14 of the study and adjuvanted in IFA (Incomplete Freund's Adjuvant). The 1 ml-volume was administered in the neck and split in two points of 0.5 ml each for ethical reasons.

Blood samples were collected at day 0, 14 and 35 of study. The serological response was then analyzed by ELISA/Western-Blot from the blood extractions performed during the study.

Figure 9:
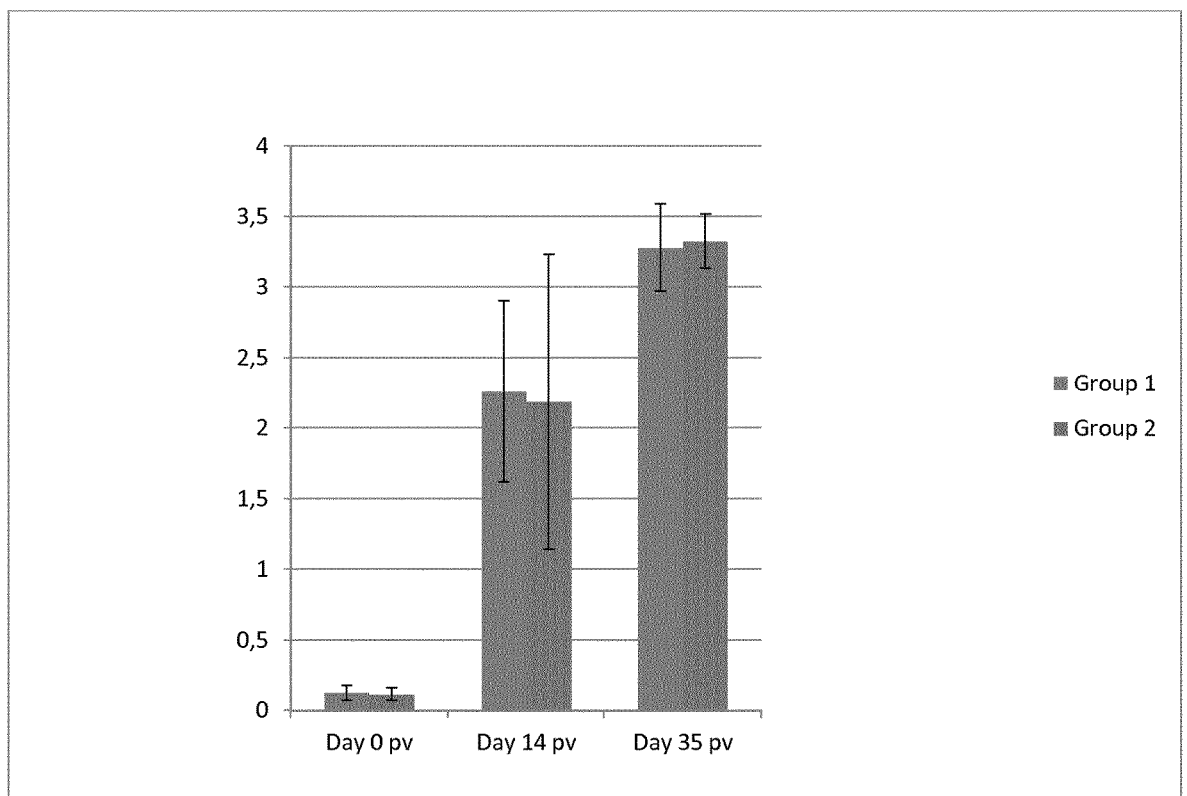
FIG. 9. Immunogenicity assay against two different *T. pedis* strains in rabbits (ELISA of sera obtained at days 0, 14 and 35 post-vaccination). Mean of the optical density at 405 nm (OD) is shown, as the ordinates, at different days post-vaccination as the abscissas, for Group 1 and Group 2. Each Group is illustrated in example 3.

The results showed seroconversion for both groups against the homologous *Treponema* species. Seroconversion at days 14 and 35 post-vaccination was significant when compared to day 0 post-vaccination for both vaccines. The response was equivalent for both groups, either at one or at two doses (FIG. 9).

The serological response against heterologous *Treponema* species, such as *T. phagedenis* and *T. medium* was also analyzed. Equivalent response was seen for both groups. It was observed seroconversion for both *T. phagedenis* and *T. medium*, demonstrating cross-protection of the *T. pedis* strain.

From the results, it can be concluded that the protection of a vaccine containing *T. pedis* bacterin does not depend of a specific strain, as different strains had an equivalent serological response. In addition, cross-protection of *T. pedis* strain was seen against heterologous *Treponema* spp., such as *T. phagedenis* and *T. medium*.

Example 4: Immunogenicity of Experimental *T. phagedenis* vaccine Against BDD 20 calves between 2 and 3 months of age, with low levels or free of antibodies against *T. pedis*, *T. phagedenis* and *T. medium* and without clinical signs of BDD were chosen for this study. The animals were randomly assigned into 2 treatment groups of 10 calves each one (Group 1 and Group 2).

Group 1 received a vaccine comprising a PBS sterile solution without antigens formulated with the adjuvant Montanide A as described in Example 1 at 50% w/w. This group corresponded to the control group.

Group 2 received a vaccine based on a *T. phagedenis* bacterin, which comprised $10^9$ total bacteria per dose of inactivated *T. phagedenis* isolate (reference number B-7330, HIPRA SCIENTIFIC, S.L.U.). The vaccine of Group 2 was formulated at 50% w/w with the adjuvant Montanide A, as described in Example 1.

The vaccines were administered at the neck region by intramuscular route at 2 ml each administration. Both groups, received a first dose of the vaccine at Day 0. Three weeks later (Day 21) calves received a second dose of the vaccine at the opposite side of the neck.

The immunogenicity of the experimental vaccine was carried out analyzing the sera from vaccinated animals at days 0, 21, 35, 48, and 69 post-vaccination by indirect ELISA assay, in order to detect the presence of antibodies in the animals' sera.

Serology post-vaccination was analyzed by ELISA (IgG2) against whole bacterium *T. pedis*, *T. phagedenis* and *T. medium* in order to assess the antibody humoral response to that *Treponema* spp.

An immunological response against the different *Treponema* spp. tested (*T. pedis*, *T. pahgedenis* and *T. medium*) was clearly observed from animal's sera of Group 2. Since the vaccine formulation of Group 2 did not contain *T. pedis* or *T. medium* bacterins, the immunological response observed in vaccinated animals can be attributed to the cross-reactivity between *Treponema* spp. (FIG. 10).

Furthermore a clear inhibitory effect on the in vitro growth of *T. phagedenis* with the sera of calves vaccinated with the *T. phagedenis* bacterin (Group 2) was observed. This inhibitory effect was not observed for the control group.

Once again, these results suggest that the immunological response observed in vaccinated animals can be attributed to the cross reactivity between *Treponema* species which share some epitopes which are responsible for that cross reaction.

Example 5 Immunogenicity of Experimental Vaccines Against BDD 30 calves between 2 and 3 months of age, with low levels or free of antibodies against *T. pedis*, *T. phagedenis* and *T. medium* and without clinical signs of BDD were chosen for this study. The animals were randomly assigned into 3 treatment groups of 10 calves each one (Group 1, Group 2 and Group 3).

Group 1 received a vaccine comprising a PBS sterile solution without antigens formulated with the adjuvant Montanide A as described in Example 1 at 50% w/w. This group corresponded to the control group.

Group 2 received a vaccine based on a *T. phagedenis* bacterin, which comprised $10^9$ total bacteria per dose of inactivated *T. phagedenis* isolate (reference number B-7330, HIPRA SCIENTIFIC, S.L.U.) combined with the following recombinant proteins: MSP protein (SEQ ID NO: 15) of *T. phagedenis*, PrtPM protein (SEQ ID NO: 2) of *T. pedis* and Apr2BM protein (SEQ ID NO: 10) of *D. nodosus* at 50 µg of each recombinant protein per dose. The vaccine was formulated with the adjuvant Montanide A as described in Example 1 at 50% w/w.

Group 3 received a vaccine based on a *T. phagedenis* bacterin, which comprised $10^9$ total bacteria per dose of inactivated *T. phagedenis* isolate (reference number B-7330, HIPRA SCIENTIFIC, S.L.U.). The vaccine was formulated at 50% w/w with the adjuvant Montanide A, as described in Example 1.

| Groups | Antigen |
| --- | --- |
| 1 (n = 10) | Placebo (PBS solution) |
| 2 (n = 10) | *T. phagedenis* inactivated bacterin + 3 recombinant proteins (MSP from *T. phagedenis*, PrtPM from *T. pedis*, Apr2BM from *D. nodosus*) |
| 3 (n = 10) | *T. phagedenis* inactivated bacterin |

Calves in all groups received a first dose of the vaccine at Day 0 at the neck region. Three weeks later (Day 21) calves received a second dose of the vaccine at the opposite side of the neck. The vaccines were administered at neck region by intramuscular route at 2 ml each administration.

The immunogenicity of the experimental vaccine was carried out analyzing the sera from vaccinated animals at days 0, 21, 35, 48, and 69 post-vaccination by indirect ELISA assay, in order to detect the presence of antibodies in the animals' sera.

Figure 11:
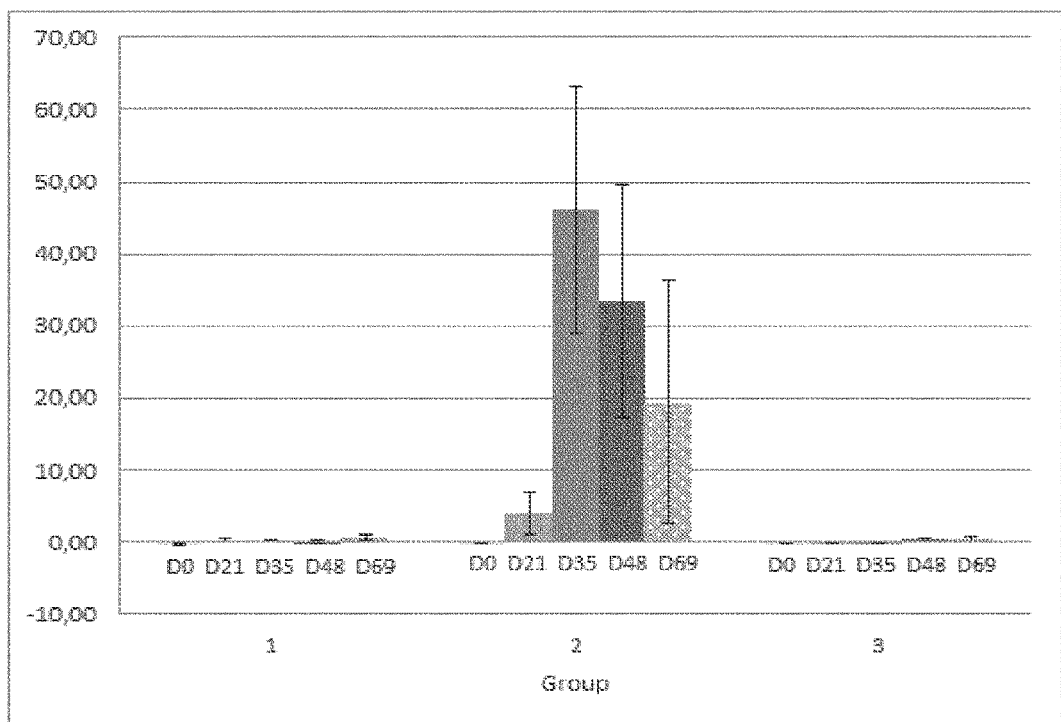
FIG. 11: Serology/ELISA against *T. pedis* PrtPM protein (A), *D. nodosus* Apr2 protein (B), and *T. phagedenis* MSP protein (C) of sera obtained from vaccinated cattle at days 0, 21, 35, 48, and 69. Mean of IRPC (Relative Index Percentage) is shown as the ordinates for the different groups, as the abscissas. Each Group is illustrated in example 5.

Serology post-vaccination was analyzed by ELISA (IgG2) against *T. pedis* PrtPM protein, *D. nodosus* Apr2 protein and *T. phagedenis* MSP protein (FIG. 11) in order to assess the antibody humoral response conferred by the vaccines to that proteins.

An immunological response against all the antigens present in the vaccine composition in animal's sera of vaccinated Group 2 was clearly observed. Furthermore, the immunological response against the MSP protein of *T. phagedenis* was increased when the bacterin was complemented with the recombinant proteins (Group 2). Even though, Group 3 (bacterin alone) developed a clear immunological response as well.

Contrary, the control group (Group 1) did not develop an immunologically response to any of the tested antigens.

Moreover, a clear inhibitory effect on the in vitro growth of *T. phagedenis* was observed in the sera of vaccinated calves of Group 2 (bacterin+recombinant proteins) and 3 (bacterin alone). These results demonstrate the presence of neutralizing antibodies in animals vaccinated of Group2 and 3.

The invention claimed is:

1. A method for inducing an immune response against digital dermatitis in a mammal, the method comprising:
administering an effective amount of a pharmaceutical composition comprising an immunogenically effective amount of a *Treponema pedis* bacterin to the mammal, wherein the mammal is an ungulate, and wherein the digital dermatitis is bovine digital dermatitis, contagious ovine digital dermatitis, footrot or combinations thereof.

2. The method of claim 1, wherein the pharmaceutical composition comprises *Treponema pedis* bacterin in the form of a suspension of killed bacteria.

3. The method of claim 1, wherein the pharmaceutical composition further comprises one or more isolated antigens from *Treponema* spp. or other digital dermatitis causative pathological agents.

4. The method of claim 3, wherein said one or more isolated antigens are selected from the group consisting of adhesins, proteases, peptidases, surface antigens, proteins involved in motility and hemolysins.

5. The method of claim 3, wherein said one or more isolated antigens are selected from the group consisting of MSP and PrtP from *Treponema pedis*; MSP and Haemolysin III from *Treponema phagedenis*; PrtP from *Treponema vincentii*; and Apr2, Apr5 and Bpr from *Dichelobacter nodosus*, and any combinations thereof, wherein said antigens are optionally recombinantly produced.

6. The method of claim 3, wherein said one or more isolated antigens are selected from the group consisting of PrtPM, TlyC and OrfC from *Treponema pedis*; PrtPM from *Treponema vincentii*; and Apr2BM, Apr5M and BprM from *Dichelobacter nodosus*, and any combinations thereof, wherein said antigens are optionally recombinantly produced.

7. The method of claim 3, wherein said one or more isolated antigens are selected from the group consisting of MSP and PrtP from *Treponema pedis*; and Apr2, Apr5 and Bpr from *Dichelobacter nodosus*, wherein said antigens are optionally recombinantly produced.

8. The method of claim 3, wherein said one or more isolated antigens are selected from the group consisting of PrtPM, TlyC and OrfC from *Treponema pedis*; and Apr2BM, Apr5M and BprM from *Dichelobacter nodosus*, wherein said antigens are optionally recombinantly produced.

9. The method of claim 1, wherein the pharmaceutical composition further comprises an immunogenically effective amount of a bacterin selected from the group consisting of *Treponema medium*, *Treponema vincentii*, *Treponema phagedenis*, *Treponema refringens*, *Treponema calligyrum*, *Treponema maltophilum* and *Treponema brennaborense*, and any combination thereof.

10. The method of claim 1, wherein the pharmaceutical composition is a vaccine.

11. The method of claim 1, wherein the pharmaceutical composition further comprises a bovine respiratory syncytial virus antigen, a bovine herpes virus antigen, a leptospiral antigen, a bovine diarrhoea virus antigen, a bovine parainfluenza virus antigen, a vesicular stomatitis virus antigen, a malignant catarrhal fever virus antigen, a blue tongue virus antigen, a pseudorabies virus antigen, a rabies virus antigen, a rinderpest virus antigen, a *Guggenheimella* antigen, a *Porphyromonas* antigen, a *Bacteroides* antigen, a *Prevotella* antigen, a Peptosteptococcus antigen, a *Campylobacter* antigen, a *Mycoplasma* antigen, a *Corynebacterium/Actinomyces* antigen, a *Cryptosporidium* antigen, a rotavirus antigen, a coronvavirus antigen a *Fusobacterium necrophorum* antigen, a *Dichelobacter nodosus* antigen, or a *Clostridia* spp. antigen.

12. The method of claim 1, wherein the pharmaceutical composition further comprises a pharmaceutically acceptable carrier.

13. The method of claim 1, wherein the immune response prevents digital dermatitis.

14. The method of claim 1, wherein the immune response treats digital dermatitis.

15. The method of claim 1, wherein the immune response reduces the incidence of infection or incident of disease in the ungulate for either the treatment or prevention of digital dermatitis disease.

16. The method of claim 1, wherein the immune response lessens the severity of infection or incident of disease in the ungulate for either the treatment or prevention of digital dermatitis disease.

17. The method of claim 1, wherein the ungulate is selected from the group consisting of cows, horses, pigs, sheep, goats or cattle.

* * * * *